(12) United States Patent
Schmitt et al.

(10) Patent No.: US 9,803,253 B2
(45) Date of Patent: Oct. 31, 2017

(54) DIAGNOSTIC TRANSCRIPT AND SPLICE PATTERNS OF HPV16 IN DIFFERENT CERVICAL LESIONS

(75) Inventors: Markus Schmitt, Heidelberg (DE); Lutz Gissmann, Wiesloch (DE); Michael Pawlita, Eschelbronn (DE)

(73) Assignee: Deutsches Krebsforschungszentrum (DE)

( * ) Notice: Subject to any disclaimer, the term of this patent is extended or adjusted under 35 U.S.C. 154(b) by 625 days.

(21) Appl. No.: 13/128,201

(22) PCT Filed: Nov. 9, 2009

(86) PCT No.: PCT/EP2009/064811
§ 371 (c)(1),
(2), (4) Date: Sep. 27, 2011

(87) PCT Pub. No.: WO2010/052317
PCT Pub. Date: May 14, 2010

(65) Prior Publication Data
US 2012/0040334 A1     Feb. 16, 2012

(30) Foreign Application Priority Data

Nov. 7, 2008  (EP) .................................... 08168608
Nov. 9, 2009  (WO) .................. PCTEP2009064811

(51) Int. Cl.
*C12Q 1/68* (2006.01)
*C12P 19/34* (2006.01)
*C12Q 1/70* (2006.01)

(52) U.S. Cl.
CPC .................................. *C12Q 1/708* (2013.01)

(58) Field of Classification Search
CPC ............. C12C 1/708; C12C 2545/113; C12Q 2545/113
See application file for complete search history.

(56) References Cited

U.S. PATENT DOCUMENTS 5,876,937 A     3/1999 Sillekens
2013/0029319 A1*  1/2013 Schmitt et al. .................. 435/5

FOREIGN PATENT DOCUMENTS

| EP | 2184368 A1 | 5/2010 |
|---|---|---|
| WO | PCTEP2009064811 | 2/2010 |
| WO | PCTEP2009064811 | 4/2011 |

OTHER PUBLICATIONS

McNicol P et al. Expression of human papillomavirus type 16 E6-E7 open reading frame varies quantitatively in biopsy tissue from different grades of cervical intraepithelial neoplasia. J Clin Microbiol. May 1995;33(5):1169-73.*
Soeda et al. Repression of HPV16 early region transcription by the E2 protein. Virology 2006;351: 29-41.*
Höfler D. HPV16 RNA patterns as diagnostic marker for cervical cancer precursor lesions: Validation by newly developed high-throughput RT-qPCR [dissertation]. Heidelberg (Germany): Ruperto-Carola University, 2013.*
Myers, G. et al. Part I. HPV and Anmal PV Nucleotide Sequences in GenBank style: Groups A1 through A9, 1995 [retrieved on-line: https://pave.niaid.nih.gov/lanl-archives/HPVcompintro4.html, retrieval date: Sep. 19, 2017].*
Alloul, Nathalie, et al., 1999, "Transcription-modulatory activities of differentially spliced cDNAs encoding the E2 protein of human papillomavirus type 16", Journal of General Virology, 80:2461-2470.
Greijer, Astrid E., et al., 2000, "Human Cytomegalovirus Virions Differentially Incorporate Viral and Host Cell RNA during the Assembly Process", Journal of Virology, 74(19):9078-9082.
Hoyer, Heike, et al., 2005, "Cumulative 5-year diagnoses of CIN2, CIN3 or cervical cancer after concurrent high-risk HPV and cytology testing in a primary screening setting", International Journal of Cancer, 116:136-143.
Kraus, I, et al., 2004, "Human papillomavirus oncogenic expression in the dysplasic portio; an investigation of biopsies from 190 cervical cones", British Journal of Cancer, 90:1407-1413.
Molden, Tor, et al., 2007, "PreTect HPV-Proofer: Real-time detection and typing of E6/E7 mRNA from carcinogenic human papillomaviruses", Journal of Virological Methods, 142:204-212.
Pim, David, et al., 1997, "Alternatively spliced HPV-18 E6* protein inhibits E6 mediated degradation of p53 and suppresses transformed cell growth", Oncogene, 15:257-264.
Sherman, L., et al., 1992, "Human Papillomavirus Type 16 Expresses a Variety of Alternatively Spliced mRNAs Putatively Encoding the E2 Protein", Virology, 191:953-959.
Sotlar, Karl, et al., 2004, "Detection of High-Risk Human Papillomavirus E6 and E7 Oncogene Transcripts in Cervical Scrapes by Nested RT-Polymerase Chain Reaction", Journal of Medical Virology, 74:107-116. Wang-Johanning, Feng, et al., 2002, "Quantitation of Human Papillomavirus 16 E6 and E7 DNA and RNA in Residual Material from ThinPrep Papanicolaou Tests Using Real-Time Polymerase Chain Reaction Analysis", Cancer, 94:2199-2210.
Zerbini, M., et al., 2006, "Analysis of HPV16 E6*I-II transcripts in cervical samples", Journal of Clinical Virology, 36 (S2):S8.
Zheng, Zhi-Ming, et al., 2006, "Papillomavirus genome structure, expression, and post-transcriptional regulations", Frontiers in Bioscience, 11:2286-2302.
Compton, J. 1991. Nucleic acid sequence-based amplification. Nature 350:91-92.

(Continued)

*Primary Examiner* — Young J Kim
(74) *Attorney, Agent, or Firm* — J.A. Lindeman & Co., PLLC

(57) ABSTRACT

A method is described for differentiating in a subject with HPV16 between (i) a severe form of HPV16 infection and (ii) a mild form of HPV16 infection based on determining the amount of a first gene product and a second gene product in a sample of a subject and calculating a ratio of the amount of the first gene product and the amount of the second gene product. A composition is also described, including an oligonucleotide mixture, and also a kit and a device adapted to carry out the described method.

6 Claims, 8 Drawing Sheets

(56) References Cited

OTHER PUBLICATIONS

Meyers C, Mayer TJ, Ozbun MA. Synthesis of infectious human papillomavirus type 18 in differentiating epithelium transfected with viral DNA. J. Virol. 1997;71:7381-7386.

Snijders PJ, van den Brule AJ, Schrijnemakers HF, Raaphorst PM, Meijer CJ, Walboomers JM. Human papillomavirus type 33 in a tonsillar carcinoma generates its putative E7 mRNA via two E6* transcript species which are terminated at different early region poly(A) sites. J. Virol. 1992;66:3172-3178.

Baker, Carl, et al., 1997, "Maps of Papillomavirus mRNA Transcripts", Los Alamos National Laboratories, Los Alamos, NM, USA.

Baldwin, Peter, et al., 2003, "Translational approaches to improving cervical screening", Nature Reviews, 3:217-226.

Birner, Peter, et al., 2001, "Signal-Amplified Colorimetric in Situ Hybridization for Assessment of Human Papillomavirus Infection in Cervical Lesions", Modern Pathology 14(7):702-709.

Bulkmans, N. W. J., et al, 2007, "Human papillomavirus DNA testing for the detection of cervical intraepithelial neoplasia grade 3 and cancer: 5-year follow-up of a randomized controlled implementation trial", Lancet, 370:1764-1772.

Castle, Philip, et al. 2008, "Human Papillomavirus Genotype Specificity of Hybrid Capture 2", Journal of Clinical Microbiology, 46(8):2595-2604.

Cuschieri, Kate S., et al., 2004, "Human Papillomavirus Type Specific DNA and RNA Persistence—Implications for Cervical Disease Progression and Monitoring", Journal of Medical Virology, 73:65-70.

De Villiers, Ethel-Michele, 2004, "Classification of papillomaviruses", Virology, 324:17-27.

Dallenbach-Hellweg, Gisela, et al. 2004, "Traditional and New Molecular Methods for Early Detection of Cervical Cancer", Ark. Pathology, 66(5):35-39.

Gheit, Tarik, et al., 2009, "Prevalence of human papillomavirus types in cervical and oral cancers in central India", Vaccine, 27:636-639.

Molijn, Anco, et al. 2005, "Molecular diagnosis of human papillomavirus (HPV) infections", Journal of Clinical Virology, 32S:S43-S51.

Pett, M. et al.., 2007, "Integration of high-risk human papillomavirus: a key event in cervical carcinogenisis?", Journal of Pathology, 212:356-367.

Sabol, Ivan, et al., 2008, "Evaluation of Different Techniques for Identification of Human Papillomavirus Types of Low Prevalence", Journal of Clinical Microbiology, 46(5): 1606-1613.

Schmitt, Markus, et al., 2006, "Bead-Based Multiplex Genotyping of Human Papillomaviruses", Journal of Clinical Microbiology, 44(2): 504-512.

Schmitt, Markus, et al., 2010, "Diagnosing Cervical Cancer and High-Grade Precursors by HPV16 Transcription Patterns", 70:249-256, Cancer Res.

Schmitt, Markus, et al., 2010, "Abundance of Multiple High-Risk Human Papillomavirus (HPV) Infections Found in Cervical Cells Analyzed by Use of an Ultrasensitive HPV Genotyping Assay", Journal of Clinical Microbiology, 48 (1):143-149.

Smith, J. H. F. 2002, "Bethesda 2001", Cytopathology, 13:4-10.

Van Gemen, Bob, et al, 1993, "Quantification of HIV-1 RNA in plasma using NASBA during HIV-1 primary infection", Journal of Virological Methods, 43:177-188.

Vinokurova, Svetlana, et al., 2008, "Type-Dependent Integration Frequency of Human Papillomavirus Genomes in Cervical Lesions.", 68:307-313.

Köhler and Milstein, Continuous cultures of fused cells secreting antibody of predefined specificity, Nature 256 (1975), 495-497.

Malmborg, BIAcore as a tool in antibody engineering, J. Immunol. Methods, 183 (1995), 7-13).

de Boer, High Human Papillomavirus Oncogene mRNA Expression and Not Viral DNA Load Is Associated with Poor Prognosis in Cervical Cancer Patients, Clin. Cancer Res., 2007, 13, 132-138.

Kraus, The Majority of Viral-Cellular Fusion Transcripts in Cervical Carcinomas Cotranscribe Cellular Sequences of Known or Predicted Genes, Cancer Res., 2008, 68, 2514-2522.

Klaes,Detection of High-Risk Cervical Intraepithelial Neoplasia and Cervical Cancer by Amplification of Transcripts Derived from Integrated Papillomavirus Oncogenes, Cancer Res., 1999, 59, 6132-6136.

Galfré, Preparation of Monoclonal Antibodies: Strategies and Procedures, Meth. Enzymol. 73 (1981) 3-46.

\* cited by examiner

Fig.: 3

Fig. 6
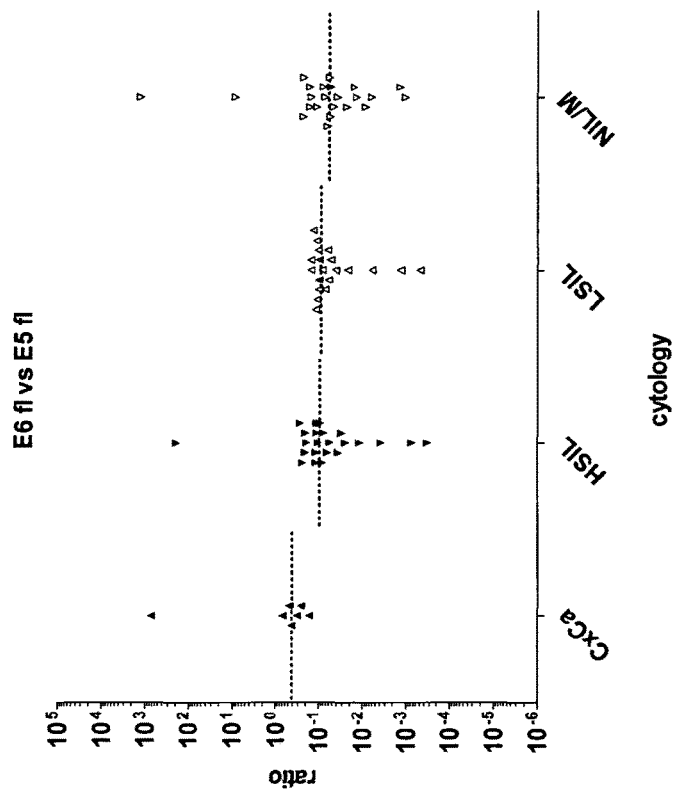
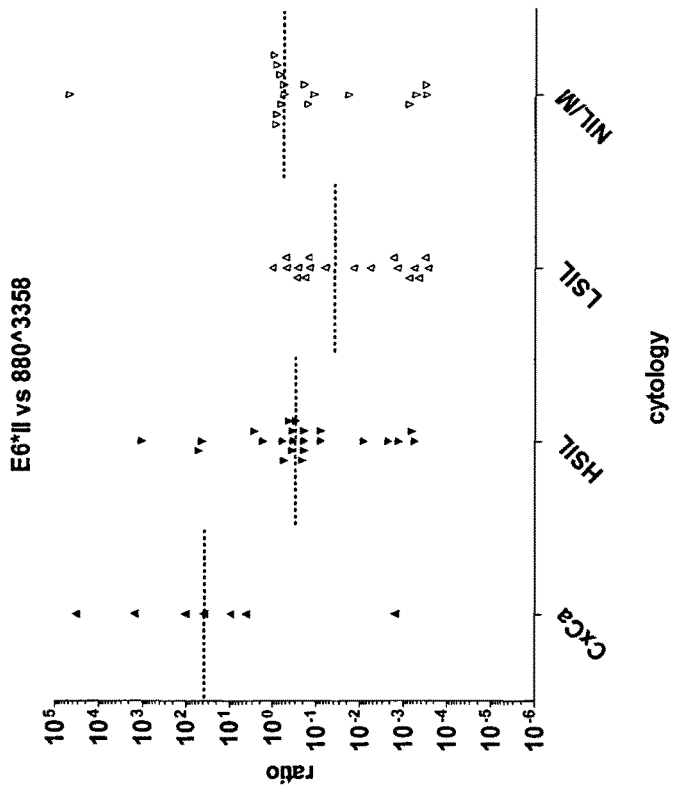

Fig. 7

Biomérieux

| | Cytology | | n |
|---|---|---|---|
| | + | − | |
| + | 27 | 36 | 63 |
| − | 1 | 11 | 12 |
| | 28 | 47 | |
| | CxCa+HSIL | LSIL+NIL/M | |

DKFZ

| | Cytology | | n |
|---|---|---|---|
| | + | − | |
| + | 20 | 8 | 28 |
| − | 8 | 39 | 47 |
| | 28 | 47 | |
| | CxCa+HSIL | LSIL+NIL/M | |

SEQUENCE LISTING

<160> NUMBER OF SEQ ID NOS: 83

<210> SEQ ID NO 1
<211> LENGTH: 7906
<212> TYPE: DNA
<213> ORGANISM: Human papillomavirus type 16

<400> SEQUENCE: 1

| | | | | | |
|---|---|---|---|---|---|
| actacaataa | ttcatgtata | aaactaaggg | cgtaaccgaa | atcggttgaa | ccgaaaccgg | 60 |
| ttagtataaa | agcagacatt | ttatgcacca | aaagagaact | gcaatgtttc | aggacccaca | 120 |
| ggagcgaccc | agaaagttac | cacagttatg | cacagagctg | caaacaacta | tacatgatat | 180 |
| aatattagaa | tgtgtgtact | gcaagcaaca | gttactgcga | cgtgaggtat | atgactttgc | 240 |
| ttttcgggat | ttatgcatag | tatatagaga | tgggaatcca | tatgctgtat | gtgataaatg | 300 |
| tttaaagttt | tattctaaaa | ttagtgagta | tagacattat | tgttatagtt | tgtatggaac | 360 |
| aacattagaa | cagcaataca | acaaaccgtt | gtgtgatttg | ttaattaggt | gtattaactg | 420 |
| tcaaaagcca | ctgtgtcctg | aagaaaagca | aagacatctg | gacaaaaagc | aaagattcca | 480 |
| taatataagg | ggtcggtgga | ccggtcgatg | tatgtcttgt | tgcagatcat | caagaacacg | 540 |
| tagagaaacc | cagctgtaat | catgcatgga | gatacaccta | cattgcatga | atatatgtta | 600 |
| gatttgcaac | cagagacaac | tgatctctac | tgttatgagc | aattaaatga | cagctcagag | 660 |
| gaggaggatg | aaatagatgg | tccagctgga | caagcagaac | cggacagagc | ccattacaat | 720 |
| attgtaacct | tttgttgcaa | gtgtgactct | acgcttcggt | tgtgcgtaca | aagcacacac | 780 |
| gtagacattc | gtactttgga | agacctgtta | atgggcacac | taggaattgt | gtgccccatc | 840 |
| tgttctcaga | aaccataatc | taccatggct | gatcctgcag | gtaccaatgg | ggaagagggt | 900 |
| acgggatgta | atggatggtt | ttatgtagag | gctgtagtgg | aaaaaaaaac | aggggatgct | 960 |
| atatcagatg | acgagaacga | aaatgacagt | gatacaggtg | aagatttggt | agattttata | 1020 |
| gtaaatgata | atgattattt | aacacaggca | gaaacagaga | cagcacatgc | gttgtttact | 1080 |
| gcacaggaag | caaacaaca | tagagatgca | gtacaggttc | taaaacgaaa | gtatttgggt | 1140 |
| agtccactta | gtgatattag | tggatgtgta | gacaataata | ttagtcctag | attaaaagct | 1200 |
| atatgtatag | aaaacaaag | tagagctgca | aaaaggagat | tatttgaaag | cgaagacagc | 1260 |
| gggtatggca | atactgaagt | ggaaactcag | cagatgttac | aggtagaagg | gcgccatgag | 1320 |
| actgaaacac | catgtagtca | gtatagtggt | ggaagtgggg | gtggttgcag | tcagtacagt | 1380 |
| agtggaagtg | ggggagaggg | tgttagtgaa | agacacacta | tatgccaaac | accacttaca | 1440 |
| aatattttaa | atgtactaaa | aactagtaat | gcaaaggcag | caatgttagc | aaaatttaaa | 1500 |
| gagttatacg | gggtgagttt | ttcagaatta | gtaagaccat | ttaaaagtaa | taaatcaacg | 1560 |
| tgttgcgatt | ggtgtattgc | tgcatttgga | cttacaccca | gtagctga | cagtataaaa | 1620 |
| acactattac | aacaatattg | tttatattta | cacattcaaa | gtttagcatg | ttcatgggga | 1680 |
| atggttgtgt | tactattagt | aagatataaa | tgtggaaaaa | atagagaaac | aattgaaaaa | 1740 |
| ttgctgtctca | aactattatg | tgtgtctcca | atgtgtatga | tgatagagcc | tccaaaattg | 1800 |
| cgtagtacag | cagcagcatt | atattggtat | aaaacaggta | tatcaaatat | tagtgaagtg | 1860 |
| tatggagaca | cgccagaatg | gatacaaaga | caaacagtat | tacaacatag | ttttaatgat | 1920 |
| tgtacatttg | aattatcaca | gatggtacaa | tgggcctacg | ataatgacat | agtagacgat | 1980 |
| agtgaaattg | catataaata | tgcacaattg | gcagacacta | atagtaatgc | aagtgccttt | 2040 |
| ctaaaaagta | attcacaggc | aaaaattgta | aaggattgtg | caacaatgtg | tagacattat | 2100 |

```
aaacgagcag aaaaaaaaca aatgagtatg agtcaatgga taaaatatag atgtgatagg    2160
gtagatgatg gaggtgattg gaagcaaatt gttatgtttt taaggtatca aggtgtagag    2220
tttatgtcat ttttaactgc attaaaaaga tttttgcaag gcatacctaa aaaaaattgc    2280
atattactat atggtgcagc taacacaggt aaatcattat ttggtatgag tttaatgaaa    2340
tttctgcaag ggtctgtaat atgttttgta aattctaaaa gccatttttg gttacaacca    2400
ttagcagatg ccaaaatagg tatgttagat gatgctacag tgccctgttg gaactacata    2460
gatgacaatt taagaaatgc attggatgga aatttagttt ctatggatgt aaagcataga    2520
ccattggtac aactaaaatg ccctccatta ttaattacat ctaacattaa tgctggtaca    2580
gattctaggt ggccttattt acataataga ttggtggtgt ttacatttcc taatgagttt    2640
ccatttgacg aaaacggaaa tccagtgtat gagcttaatg ataagaactg gaaatccttt    2700
ttctcaagga cgtggtccag attaagtttg cacgaggacg aggacaagga aaacgatgga    2760
gactctttgc caacgtttaa atgtgtgtca ggacaaaata ctaacacatt atgaaaatga    2820
tagtacagac ctacgtgacc atatagacta ttggaaacac atgcgcctag aatgtgctat    2880
ttattacaag gccagagaaa tgggatttaa acatattaac caccaagtgg tgccaacact    2940
ggctgtatca aagaataaag cattacaagc aattgaactg caactaacgt tagaaacaat    3000
atataactca caatatagta atgaaaagtg gacattacaa gacgttagcc ttgaagtgta    3060
tttaactgca ccaacaggat gtataaaaaa acatggatat acagtggaag tgcagtttga    3120
tggagacata tgcaatacaa tgcattatac aaactggaca catatatata tttgtgaaga    3180
agcatcagta actgtggtag agggtcaagt tgactattat ggtttatatt atgttcatga    3240
aggaatacga acatattttg tgcagtttaa agatgatgca gaaaaatata gtaaaaataa    3300
agtatgggaa gttcatgcgg gtggtcaggt aatattatgt cctacatctg tgtttagcag    3360
caacgaagta tcctctcctg aaattattag gcagcacttg gccaaccacc ccgccgcgac    3420
ccataccaaa gccgtcgcct tgggcaccga agaaacacag acgactatcc agcgaccaag    3480
atcagagcca gacaccggaa acccctgcca caccactaag ttgttgcaca gagactcagt    3540
ggacagtgct ccaatcctca ctgcatttaa cagctcacac aaaggacgga ttaactgtaa    3600
tagtaacact acacccatag tacatttaaa aggtgatgct aatactttaa aatgtttaag    3660
atatagattt aaaaagcatt gtacattgta tactgcagtg tcgtctacat ggcattggac    3720
aggacataat gtaaaacata aaagtgcaat tgttacactt acatatgata gtgaatggca    3780
acgtgaccaa ttttgtctc aagttaaaat accaaaaact attacagtgt ctactggatt    3840
tatgtctata tgacaaatct tgatactgca tccacaacat tactggcgtg ctttttgctt    3900
tgcttttgtg tgcttttgtg tgtctgccta ttaatacgtc cgctgctttt gtctgtgtct    3960
acatacacat cattaataat attggtatta ctattgtgga taacagcagc ctctgcgttt    4020
aggtgtttta ttgtatatat tatatttgtt tatataccat tatttttaat acatacacat    4080
gcacgctttt taattacata atgtatatgt acataatgta attgttacat ataattgttg    4140
tataccataa cttactattt tttctttttt attttcatat ataatttttt ttttgtttg    4200 tttgtttgtt ttaataaa ctgttattac ttaacaatgc gacacaaacg ttctgcaaaa    4260
cgcacaaaac gtgcatcggc tacccaactt tataaacat gcaaacaggc aggtacatgt    4320
ccacctgaca ttatacctaa ggttgaaggc aaaactattg ctgatcaaat attacaatat    4380
ggaagtatgg gtgtattttt tggtgggtta ggaattggaa cagggtcggg tacaggcgga    4440
```

-continued

```
cgcactgggt atattccatt gggaacaagg cctcccacag ctacagatac acttgctcct    4500
gtaagacccc ctttaacagt agatcctgtg ggcccttctg atccttctat agtttcttta    4560
gtggaagaaa ctagttttat tgatgctggt gcaccaacat ctgtaccttc cattccccca    4620
gatgtatcag gatttagtat tactacttca actgatacca cacctgctat attagatatt    4680
aataatactg ttactactgt tactacacat aataatccca ctttcactga cccatctgta    4740
ttgcagcctc caacacctgc agaaactgga gggcattttta cactttcatc atccactatt    4800
agtacacata attatgaaga aattcctatg gatacattta ttgttagcac aaaccctaac    4860
acagtaacta gtagcacacc cataccaggg tctcgcccag tggcacgcct aggattatat    4920
agtcgcacaa cacaacaggt taaagttgta gaccctgctt ttgtaaccac tcccactaaa    4980
cttattacat atgataatcc tgcatatgaa ggtatagatg tggataatac attatatttt    5040
tctagtaatg ataatagtat taatatagct ccagatcctg acttttttgga tatagttgct    5100 ttacataggc cagcattaac ctctaggcgt actggcatta ggtacagtag aattggtaat    5160
aaacaaacac tacgtactcg tagtggaaaa tctataggtg ctaaggtaca ttattattat    5220
gatttaagta ctattgatcc tgcagaagaa atagaattac aaactataac accttctaca    5280
tatactacca cttcacatgc agcctcacct acttctatta ataatggatt atatgatatt    5340
tatgcagatg actttattac agatacttct acaaccccgg taccatctgt accctctaca    5400
tctttatcag gttatattcc tgcaaataca acaattcctt ttggtggtgc atacaatatt    5460
cctttagtat caggtcctga tatacccatt aatataactg accaagctcc ttcattaatt    5520
cctatagttc cagggtctcc acaatataca attattgctg atgcaggtga cttttattta    5580
catcctagtt attacatgtt acgaaaacga cgtaaacgtt taccatatttt tttttcagat    5640 gtctctttgg ctgcctagtg aggccactgt ctacttgcct cctgtcccag tatctaaggt    5700
tgtaagcacg gatgaatatg ttgcacgcac aaacatatat tatcatgcag gaacatccag    5760
actacttgca gttggacatc cctatttttcc tattaaaaaa cctaacaata caaaatatt    5820 agttcctaaa gtatcaggat tacaatacag ggtatttaga atacatttac ctgaccccaa    5880
taagtttggt tttcctgaca cctcatttta taatccagat acacagcggc tggtttgggc    5940
ctgtgtaggt gttgaggtag gtcgtggtca gccattaggt gtgggcatta gtggccatcc    6000
tttattaaat aaattggatg acacagaaaa tgctagtgct tatgcagcaa atgcaggtgt    6060
ggataataga gaatgtatat ctatggatta caaacaaaca caattgtgtt taattggttg    6120
caaaccacct ataggggaac actggggcaa aggatccca tgtaccaatg ttgcagtaaa    6180
tccaggtgat tgtccaccat tagagttaat aaacacagtt attcaggatg gtgatatggt    6240
tgatactggc tttggtgcta tggactttac tacattacag gctaacaaaa gtgaagttcc    6300
actggatatt tgtacatcta tttgcaaata tccagattat attaaaatgg tgtcagaacc    6360 atatgcgac agcttatttt tttatttacg aagggaacaa atgtttgtta gacatttatt    6420
taatagggct ggtactgttg gtgaaaatgt accagacgat ttatacatta aaggctctgg    6480
gtctactgca aatttagcca gttcaaatta ttttcctaca cctagtggtt ctatggttac    6540
ctctgatgcc caaatattca ataaaccctta ttggttacaa cgagcacagg ccacaataa    6600 tggcatttgt tggggtaacc aactatttgt tactgttgtt gatactacac gcagtacaaa    6660
tatgtcatta tgtgctgcca tatctacttc agaaactaca tataaaaata ctaactttaa    6720
ggagtaccta cgcatggggg aggaatatga tttacagttt atttttcaac tgtgcaaaat    6780
aaccttaact gcagacgtta tgacatacat acattctatg aattccacta ttttggagga    6840
```

```
ctggaatttt ggtctacaac ctcccccagg aggcacacta gaagatactt ataggtttgt      6900
aacatcccag gcaattgctt gtcaaaaaca tacacctcca gcacctaaag aagatcccct      6960
taaaaaatac acttttttggg aagtaaattt aaaggaaaag ttttctgcag acctagatca     7020
gtttccttta ggacgcaaat ttttactaca agcaggattg aaggccaaac caaaatttac      7080
attaggaaaa cgaaaagcta cacccaccac ctcatctacc tctacaactg ctaaacgcaa      7140
aaaacgtaag ctgtaagtat tgtatgtatg ttgaattagt gttgtttgtt gtgtatatgt      7200
ttgtatgtgc ttgtatgtgc ttgtaaatat taagttgtat gtgtgtttgt atgtatggta      7260
taataaacac gtgtgtatgt gttttttaaat gcttgtgtaa ctattgtgtc atgcaacata     7320
aataaactta tgtttcaac acctactaat tgtgttgtgg ttattcattg tatataaact       7380
atatttgcta catcctgttt ttgttttata tatactatat tttgtagcgc cagcggccat      7440
tttgtagctt caaccgaatt cggttgcatg cttttttggca caaaatgtgt tttttttaaat   7500 agttctatgt cagcaactat ggtttaaact tgtacgtttc ctgcttgcca tgcgtgccaa     7560
atccctgttt tcctgacctg cactgcttgc caaccattcc attgtttttt acactgcact    7620
atgtgcaact actgaatcac tatgtacatt gtgtcatata aaataaatca ctatgcgcca    7680
acgccttaca taccgctgtt aggcacatat ttttggcttg ttttaactaa cctaattgca    7740
tatttggcat aaggtttaaa cttctaaggc caactaaatg tcaccctagt tcatacatga   7800
actgtgtaaa ggttagtcat acattgttca tttgtaaaac tgcacatggg tgtgtgcaaa   7860
ccgtttgggg ttacacattt acaagcaact tatataataa tactaa                  7906

<210> SEQ ID NO 2
<211> LENGTH: 82
<212> TYPE: PRT
<213> ORGANISM: Human papillomavirus type 16

<400> SEQUENCE: 2

Met Ala Asp Pro Ala Asp Ser Arg Trp Pro Tyr Leu His Asn Arg Leu
1               5                   10                  15

Val Val Phe Thr Phe Pro Asn Glu Phe Pro Phe Asp Glu Asn Gly Asn
            20                  25                  30

Pro Val Tyr Glu Leu Asn Asp Lys Asn Trp Lys Ser Phe Phe Ser Arg
        35                  40                  45

Thr Trp Ser Arg Leu Ser Leu His Glu Asp Glu Asp Lys Glu Asn Asp
    50                  55                  60

Gly Asp Ser Leu Pro Thr Phe Lys Cys Val Ser Gly Gln Asn Thr Asn
65                  70                  75                  80

Thr Leu

<210> SEQ ID NO 3
<211> LENGTH: 249
<212> TYPE: DNA
<213> ORGANISM: Human papillomavirus type 16

<400> SEQUENCE: 3
atggctgatc ctgcagattc yaggtggcct tatttacata atagattggt ggtgtttaca        60
tttcctaatg agtttccatt tgacgaaaac ggaaatccag tgtatgagct taatgataag       120
aactggaaat ccttttttctc aaggacgtgg tccagattaa gtttgcacga ggacgaggac      180
aaggaaaacg atggagactc tttgccaacg tttaaatgtg tgtcaggaca aaatactaac       240
acattatga                                                              249
```

```
<210> SEQ ID NO 4
<211> LENGTH: 12
<212> TYPE: DNA
<213> ORGANISM: Human papillomavirus type 16

<400> SEQUENCE: 4
ctgcagattc ya                                                             12

<210> SEQ ID NO 5
<211> LENGTH: 7
<212> TYPE: PRT
<213> ORGANISM: Human papillomavirus type 16

<400> SEQUENCE: 5

Asp Pro Ala Asp Ser Arg Trp
1               5

<210> SEQ ID NO 6
<211> LENGTH: 1518
<212> TYPE: DNA
<213> ORGANISM: Human papillomavirus type 16

<400> SEQUENCE: 6
atgtctcttt ggctgcctag tgaggccact gtctacttgc ctcctgtccc agtatctaag     60
gttgtaagca cggatgaata tgttgcacgc acaaacatat attatcatgc aggaacatcc    120
agactacttg cagttggaca tcccctatttt cctattaaaa aacctaacaa taacaaaata    180
ttagttccta aagtatcagg attacaatac agggtattta aatacatttt acctgacccc    240
aataagtttg gttttcctga cacctcattt tataatccag atacacagcg ctggtttgg     300 gcctgtgtag gtgttgaggt aggtcgtggt cagccattag tgtgggcat tagtggccat     360 cctttattaa ataaattgga tgacacagaa atgctagtg cttatgcagc aaatgcaggt    420
gtggataata gagaatgtat atctatggat acaaacaaa cacaattgtg tttaattggt    480
tgcaaaccac ctataggga acactggggc aaaggatccc catgtaccaa tgttgcagta    540
aatccaggtg attgtccacc attagagtta ataaacacag ttattcagga tggtgatatg    600
gttgatactg gctttggtgc tatggactttt actacattac aggctaacaa agtgaagtt    660 ccactggata tttgtacatc tatttgcaaa tatccagatt atattaaat ggtgtcagaa    720 ccatatggcg acagcttatt ttttatttat cgaagggaac aaatgtttgt tagacattta    780
tttaataggg ctggtactgt tggtgaaaat gtaccagacg atttatacat taaaggctct    840
gggtctactg caaatttagc cagttcaaat tattttccta cacctagtgg ttctatggtt    900
acctctgatg cccaaatatt caataaacct tattggttac aacgagcaca gggccacaat    960
aatggcattt gttggggtaa ccaactattt gttactgttg ttgatactac acgcagtaca   1020
aatatgtcat tatgtgctgc catatctact tcagaaacta catataaaaa tactaacttt   1080
aaggagtacc tacgacatgg ggaggaatat gatttacagt ttatttttca actgtgcaaa   1140
ataaccttaa ctgcagacgt tatgacatac atacattcta tgaattccac tatttggag    1200 gactggaatt ttggtctaca acctcccca ggaggcacac tagaagatac ttataggttt   1260
gtaacatccc aggcaattgc ttgtcaaaaa catacacctc cagcacctaa agaagatccc   1320
cttaaaaaat actttttttg ggaagtaaat ttaaaggaaa gtttctgc agacctagat    1380 cagtttcctt aggacgcaa atttttacta caagcaggat gaaggccaa accaaaattt    1440 acattaggaa aacgaaaagc tacacccacc acctcatcta cctctacaac tgctaaacgc   1500
```
aaaaaacgta agctgtaa                                                     1518

<210> SEQ ID NO 7
<211> LENGTH: 505
<212> TYPE: PRT
<213> ORGANISM: Human papillomavirus type 16

<400> SEQUENCE: 7

Met Ser Leu Trp Leu Pro Ser Glu Ala Thr Val Tyr Leu Pro Pro Val
1               5                   10                  15

Pro Val Ser Lys Val Val Ser Thr Asp Glu Tyr Val Ala Arg Thr Asn
            20                  25                  30

Ile Tyr Tyr His Ala Gly Thr Ser Arg Leu Leu Ala Val Gly His Pro
        35                  40                  45

Tyr Phe Pro Ile Lys Lys Pro Asn Asn Asn Lys Ile Leu Val Pro Lys
    50                  55                  60

Val Ser Gly Leu Gln Tyr Arg Val Phe Arg Ile His Leu Pro Asp Pro
65                  70                  75                  80

Asn Lys Phe Gly Phe Pro Asp Thr Ser Phe Tyr Asn Pro Asp Thr Gln
                85                  90                  95

Arg Leu Val Trp Ala Cys Val Gly Val Glu Val Gly Arg Gly Gln Pro
            100                 105                 110

Leu Gly Val Gly Ile Ser Gly His Pro Leu Leu Asn Lys Leu Asp Asp
        115                 120                 125

Thr Glu Asn Ala Ser Ala Tyr Ala Ala Asn Ala Gly Val Asp Asn Arg
    130                 135                 140

Glu Cys Ile Ser Met Asp Tyr Lys Gln Thr Gln Leu Cys Leu Ile Gly
145                 150                 155                 160

Cys Lys Pro Pro Ile Gly Glu His Trp Gly Lys Gly Ser Pro Cys Thr
                165                 170                 175

Asn Val Ala Val Asn Pro Gly Asp Cys Pro Pro Leu Glu Leu Ile Asn
            180                 185                 190

Thr Val Ile Gln Asp Gly Asp Met Val Asp Thr Gly Phe Gly Ala Met
        195                 200                 205

Asp Phe Thr Thr Leu Gln Ala Asn Lys Ser Glu Val Pro Leu Asp Ile
    210                 215                 220

Cys Thr Ser Ile Cys Lys Tyr Pro Asp Tyr Ile Lys Met Val Ser Glu
225                 230                 235                 240

Pro Tyr Gly Asp Ser Leu Phe Phe Tyr Leu Arg Arg Glu Gln Met Phe
                245                 250                 255

Val Arg His Leu Phe Asn Arg Ala Gly Thr Val Gly Glu Asn Val Pro
            260                 265                 270

Asp Asp Leu Tyr Ile Lys Gly Ser Gly Ser Thr Ala Asn Leu Ala Ser
        275                 280                 285

Ser Asn Tyr Phe Pro Thr Pro Ser Gly Ser Met Val Thr Ser Asp Ala
    290                 295                 300

Gln Ile Phe Asn Lys Pro Tyr Trp Leu Gln Arg Ala Gln Gly His Asn
305                 310                 315                 320

Asn Gly Ile Cys Trp Gly Asn Gln Leu Phe Val Thr Val Val Asp Thr
                325                 330                 335

Thr Arg Ser Thr Asn Met Ser Leu Cys Ala Ala Ile Ser Thr Ser Glu
            340                 345                 350

Thr Thr Tyr Lys Asn Thr Asn Phe Lys Glu Tyr Leu Arg His Gly Glu
        355                 360                 365

```
Glu Tyr Asp Leu Gln Phe Ile Phe Gln Leu Cys Lys Ile Thr Leu Thr
    370                 375                 380

Ala Asp Val Met Thr Tyr Ile His Ser Met Asn Ser Thr Ile Leu Glu
385                 390                 395                 400

Asp Trp Asn Phe Gly Leu Gln Pro Pro Gly Gly Thr Leu Glu Asp
                405                 410                 415

Thr Tyr Arg Phe Val Thr Ser Gln Ala Ile Ala Cys Gln Lys His Thr
                420                 425                 430

Pro Pro Ala Pro Lys Glu Asp Pro Leu Lys Lys Tyr Thr Phe Trp Glu
                435                 440                 445

Val Asn Leu Lys Glu Lys Phe Ser Ala Asp Leu Asp Gln Phe Pro Leu
    450                 455                 460

Gly Arg Lys Phe Leu Leu Gln Ala Gly Leu Lys Ala Lys Pro Lys Phe
465                 470                 475                 480

Thr Leu Gly Lys Arg Lys Ala Thr Pro Thr Thr Ser Ser Thr Ser Thr
                485                 490                 495

Thr Ala Lys Arg Lys Lys Arg Lys Leu
                500                 505

<210> SEQ ID NO 8
<211> LENGTH: 12
<212> TYPE: DNA
<213> ORGANISM: Human papillomavirus type 16

<400> SEQUENCE: 8
taaaagatgt ct                                                         12

<210> SEQ ID NO 9
<211> LENGTH: 92
<212> TYPE: PRT
<213> ORGANISM: Human papillomavirus type 16

<400> SEQUENCE: 9

Met Ala Asp Pro Ala Ala Ala Thr Lys Tyr Pro Leu Leu Lys Leu Leu
1               5                   10                  15

Gly Ser Thr Trp Pro Thr Thr Pro Pro Arg Pro Ile Pro Lys Pro Ser
                20                  25                  30

Pro Trp Ala Pro Lys Lys His Arg Arg Leu Ser Ser Asp Gln Asp Gln
                35                  40                  45

Ser Gln Thr Pro Glu Thr Pro Ala Thr Pro Leu Ser Cys Cys Thr Glu
            50                  55                  60

Thr Gln Trp Thr Val Leu Gln Ser Ser Leu His Leu Thr Ala His Thr
65                  70                  75                  80

Lys Asp Gly Leu Thr Val Ile Val Thr Leu His Pro
                85                  90

<210> SEQ ID NO 10
<211> LENGTH: 279
<212> TYPE: DNA
<213> ORGANISM: Human papillomavirus type 16

<400> SEQUENCE: 10
atggctgatc ctgcagcagc aacgaagtat cctctcctga aattattagg cagcacttgg      60
ccaaccaccc cgccgcgacc cataccaaag ccgtcgcctt gggcaccgaa gaaacacaga     120
cgactatcca gcgaccaaga tcagagccag acaccggaaa cccctgccac accactaagt     180
tgttgcacag agactcagtg gacagtgctc caatcctcac tgcatttaac agctcacaca     240
```

```
aaggacggat taactgtaat agtaacacta cacccatag                              279
```

<210> SEQ ID NO 11
<211> LENGTH: 12
<212> TYPE: DNA
<213> ORGANISM: Human papillomavirus type 16

<400> SEQUENCE: 11

```
ctrcagcagc ra                                                           12
```

<210> SEQ ID NO 12
<211> LENGTH: 7
<212> TYPE: PRT
<213> ORGANISM: Human papillomavirus type 16

<400> SEQUENCE: 12

```
Asp Pro Ala Ala Ala Thr Lys
1               5
```

<210> SEQ ID NO 13
<211> LENGTH: 50
<212> TYPE: PRT
<213> ORGANISM: Human papillomavirus type 16

<400> SEQUENCE: 13

```
Met His Gln Lys Arg Thr Ala Met Phe Gln Asp Pro Gln Glu Arg Pro
1               5                   10                  15

Arg Lys Leu Pro Gln Leu Cys Thr Glu Leu Gln Thr Thr Ile His Asp
            20                  25                  30

Ile Ile Leu Glu Cys Val Tyr Cys Lys Gln Gln Leu Leu Arg Arg Glu
        35                  40                  45

Val Tyr
    50
```

<210> SEQ ID NO 14
<211> LENGTH: 153
<212> TYPE: DNA
<213> ORGANISM: Human papillomavirus type 16

<400> SEQUENCE: 14

```
atgcaccaaa agagaactgc aatgtttcag gacccacagg agcgacccag aaagttacca      60
cagttatgca cagagctgca acaactata catgatataa tattagaatg tgtgtactgc      120
aagcaacagt tactgcgacg tgaggtgtat taa                                   153
```

<210> SEQ ID NO 15
<211> LENGTH: 12
<212> TYPE: DNA
<213> ORGANISM: Human papillomavirus type 16

<400> SEQUENCE: 15

```
cgtgaggtgt at                                                           12
```

<210> SEQ ID NO 16
<211> LENGTH: 7
<212> TYPE: PRT
<213> ORGANISM: Human papillomavirus type 16

<400> SEQUENCE: 16

```
Leu Leu Arg Arg Glu Val Tyr
1               5
```

<210> SEQ ID NO 17
<211> LENGTH: 2602
<212> TYPE: DNA
<213> ORGANISM: Human papillomavirus type 16

<400> SEQUENCE: 17

| | | | | | |
|---|---|---|---|---|---|
| gagccgcggc | taaggaacgc | gggccgccca | cccgctcccg | gtgcagcggc | ctccgcgccg | 60 |
| ggttttggcg | cctcccgcgg | gcgcccccct | cctcacggcg | agcgctgcca | cgtcagacga | 120 |
| agggcgcagc | gagcgtcctg | atccttccgc | ccggacgctc | aggacagcgg | cccgctgctc | 180 |
| ataagactcg | gccttagaac | cccagtatca | gcagaaggac | attttaggac | gggacttggg | 240 |
| tgactctagg | gcactggttt | tctttccaga | gagcggaaca | ggcgaggaaa | agtagtccct | 300 |
| tctcggcgat | tctgcggagg | gatctccgtg | gggcggtgaa | cgccgatgat | tatataagga | 360 |
| cgcgccgggt | gtggcacagc | tagttccgtc | gcagccggga | tttgggtcgc | agttcttgtt | 420 |
| tgtggatcgc | tgtgatcgtc | acttgacaat | gcagatcttc | gtgaagactc | tgactggtaa | 480 |
| gaccatcacc | ctcgaggttg | agcccagtga | caccatcgag | aatgtcaagg | caaagatcca | 540 |
| agataaggaa | ggcatccctc | ctgaccagca | gaggctgatc | tttgctggaa | acagctgga | 600 |
| agatgggcgc | accctgtctg | actacaacat | ccagaaagag | tccaccctgc | acctggtgct | 660 |
| ccgtctcaga | ggtgggatgc | aaatcttcgt | gaagacactc | actggcaaga | ccatcaccct | 720 |
| tgaggtcgag | cccagtgaca | ccatcgagaa | cgtcaaagca | aagatccagg | acaaggaagg | 780 |
| cattcctcct | gaccagcaga | ggttgatctt | tgccggaaag | cagctggaag | atgggcgcac | 840 |
| cctgtctgac | tacaacatcc | agaaagagtc | taccctgcac | ctggtgctcc | gtctcagagg | 900 |
| tgggatgcag | atcttcgtga | agaccctgac | tggtaagacc | atcaccctcg | aggtggagcc | 960 |
| cagtgacacc | atcgagaatg | tcaaggcaaa | gatccaagat | aaggaaggca | ttccttctga | 1020 |
| tcagcagagg | ttgatctttg | ccggaaaaca | gctggaagat | ggtcgtaccc | tgtctgacta | 1080 |
| caacatccag | aaagagtcca | ccttgcacct | ggtactccgt | ctcagaggtg | ggatgcaaat | 1140 |
| cttcgtgaag | acactcactg | gcaagaccat | cacccttgag | gtcgagccca | gtgacactat | 1200 |
| cgagaacgtc | aaagcaaaga | tccaagacaa | ggaaggcatt | cctcctgacc | agcagaggtt | 1260 |
| gatctttgcc | ggaaagcagc | tggaagatgg | gcgcacccctg | tctgactaca | acatccagaa | 1320 |
| agagtctacc | ctgcacctgg | tgctccgtct | caggtgggg | atgcagatct | tcgtgaagac | 1380 |
| cctgactggt | aagaccatca | ctctcgaagt | ggagccgagt | gacaccattg | agaatgtcaa | 1440 |
| ggcaaagatc | caagacaagg | aaggcatccc | tcctgaccag | cagaggttga | tctttgccgg | 1500 |
| aaaacagctg | gaagatggtc | gtaccctgtc | tgactacaac | atccagaaag | agtccacctt | 1560 |
| gcacctggtg | ctccgtctca | gaggtgggat | gcagatcttc | gtgaagaccc | tgactggtaa | 1620 |
| gaccatcact | ctcgaggtgg | agccgagtga | caccattgag | aatgtcaagg | caaagatcca | 1680 |
| agacaaggaa | ggcatccctc | ctgaccagca | gaggttgatc | tttgctggga | aacagctgga | 1740 |
| agatggacgc | accctgtctg | actacaacat | ccagaaagag | tccaccctgc | acctggtgct | 1800 |
| ccgtcttaga | ggtgggatgc | agatcttcgt | gaagaccctg | actggtaaga | ccatcactct | 1860 |
| cgaagtggag | ccgagtgaca | ccattgagaa | tgtcaaggca | aagatccaag | acaaggaagg | 1920 |
| catccctcct | gaccagcaga | ggttgatctt | tgctgggaaa | cagctggaag | atggacgcac | 1980 |
| cctgtctgac | tacaacatcc | agaaagagtc | caccctgcac | ctggtgctcc | gtcttagagg | 2040 |
| tgggatgcag | atcttcgtga | agaccctgac | tggtaagacc | atcactctcg | aagtggagcc | 2100 |
| gagtgacacc | attgagaatg | tcaaggcaaa | gatccaagac | aaggaaggca | tccctcctga | 2160 |

-continued

```
ccagcagagg ttgatctttg ctgggaaaca gctggaagat ggacgcaccc tgtctgacta    2220
caacatccag aaagagtcca ccctgcacct ggtgctccgt ctcagaggtg ggatgcaaat    2280
cttcgtgaag accctgactg gtaagaccat caccctcgag gtggagccca gtgacaccat    2340
cgagaatgtc aaggcaaaga tccaagataa ggaaggcatc cctcctgatc agcagaggtt    2400
gatctttgct gggaaacagc tggaagatgg acgcaccctg tctgactaca acatccagaa    2460
agagtccact ctgcacttgg tcctgcgctt gagggggggt gtctaagttt ccccttttaa    2520
ggtttcaaca aatttcattg cactttcctt tcaataaagt tgttgcattc ccaaaaaaaa    2580
aaaaaaaaaa aaaaaaaaaa aa                                             2602
```

<210> SEQ ID NO 18
<211> LENGTH: 685
<212> TYPE: PRT
<213> ORGANISM: Homo sapiens

<400> SEQUENCE: 18

```
Met Gln Ile Phe Val Lys Thr Leu Thr Gly Lys Thr Ile Thr Leu Glu
1               5                   10                  15

Val Glu Pro Ser Asp Thr Ile Glu Asn Val Lys Ala Lys Ile Gln Asp
            20                  25                  30

Lys Glu Gly Ile Pro Pro Asp Gln Gln Arg Leu Ile Phe Ala Gly Lys
        35                  40                  45

Gln Leu Glu Asp Gly Arg Thr Leu Ser Asp Tyr Asn Ile Gln Lys Glu
    50                  55                  60

Ser Thr Leu His Leu Val Leu Arg Leu Arg Gly Gly Met Gln Ile Phe
65                  70                  75                  80

Val Lys Thr Leu Thr Gly Lys Thr Ile Thr Leu Glu Val Glu Pro Ser
                85                  90                  95

Asp Thr Ile Glu Asn Val Lys Ala Lys Ile Gln Asp Lys Glu Gly Ile
            100                 105                 110

Pro Pro Asp Gln Gln Arg Leu Ile Phe Ala Gly Lys Gln Leu Glu Asp
        115                 120                 125

Gly Arg Thr Leu Ser Asp Tyr Asn Ile Gln Lys Glu Ser Thr Leu His
    130                 135                 140

Leu Val Leu Arg Leu Arg Gly Gly Met Gln Ile Phe Val Lys Thr Leu
145                 150                 155                 160

Thr Gly Lys Thr Ile Thr Leu Glu Val Glu Pro Ser Asp Thr Ile Glu
                165                 170                 175

Asn Val Lys Ala Lys Ile Gln Asp Lys Glu Gly Ile Pro Ser Asp Gln
            180                 185                 190

Gln Arg Leu Ile Phe Ala Gly Lys Gln Leu Glu Asp Gly Arg Thr Leu
        195                 200                 205

Ser Asp Tyr Asn Ile Gln Lys Glu Ser Thr Leu His Leu Val Leu Arg
    210                 215                 220

Leu Arg Gly Gly Met Gln Ile Phe Val Lys Thr Leu Thr Gly Lys Thr
225                 230                 235                 240

Ile Thr Leu Glu Val Glu Pro Ser Asp Thr Ile Glu Asn Val Lys Ala
                245                 250                 255

Lys Ile Gln Asp Lys Glu Gly Ile Pro Pro Asp Gln Gln Arg Leu Ile
            260                 265                 270

Phe Ala Gly Lys Gln Leu Glu Asp Gly Arg Thr Leu Ser Asp Tyr Asn
        275                 280                 285
```

```
Ile Gln Lys Glu Ser Thr Leu His Leu Val Leu Arg Leu Arg Gly Gly
        290                 295                 300

Met Gln Ile Phe Val Lys Thr Leu Thr Gly Lys Thr Ile Thr Leu Glu
305                 310                 315                 320

Val Glu Pro Ser Asp Thr Ile Glu Asn Val Lys Ala Lys Ile Gln Asp
                325                 330                 335

Lys Glu Gly Ile Pro Pro Asp Gln Gln Arg Leu Ile Phe Ala Gly Lys
            340                 345                 350

Gln Leu Glu Asp Gly Arg Thr Leu Ser Asp Tyr Asn Ile Gln Lys Glu
        355                 360                 365

Ser Thr Leu His Leu Val Leu Arg Leu Arg Gly Gly Met Gln Ile Phe
370                 375                 380

Val Lys Thr Leu Thr Gly Lys Thr Ile Thr Leu Glu Val Glu Pro Ser
385                 390                 395                 400

Asp Thr Ile Glu Asn Val Lys Ala Lys Ile Gln Asp Lys Glu Gly Ile
                405                 410                 415

Pro Pro Asp Gln Gln Arg Leu Ile Phe Ala Gly Lys Gln Leu Glu Asp
            420                 425                 430

Gly Arg Thr Leu Ser Asp Tyr Asn Ile Gln Lys Glu Ser Thr Leu His
        435                 440                 445

Leu Val Leu Arg Leu Arg Gly Gly Met Gln Ile Phe Val Lys Thr Leu
450                 455                 460

Thr Gly Lys Thr Ile Thr Leu Glu Val Glu Pro Ser Asp Thr Ile Glu
465                 470                 475                 480

Asn Val Lys Ala Lys Ile Gln Asp Lys Glu Gly Ile Pro Pro Asp Gln
                485                 490                 495

Gln Arg Leu Ile Phe Ala Gly Lys Gln Leu Glu Asp Gly Arg Thr Leu
            500                 505                 510

Ser Asp Tyr Asn Ile Gln Lys Glu Ser Thr Leu His Leu Val Leu Arg
        515                 520                 525

Leu Arg Gly Gly Met Gln Ile Phe Val Lys Thr Leu Thr Gly Lys Thr
530                 535                 540

Ile Thr Leu Glu Val Glu Pro Ser Asp Thr Ile Glu Asn Val Lys Ala
545                 550                 555                 560

Lys Ile Gln Asp Lys Glu Gly Ile Pro Pro Asp Gln Gln Arg Leu Ile
                565                 570                 575

Phe Ala Gly Lys Gln Leu Glu Asp Gly Arg Thr Leu Ser Asp Tyr Asn
            580                 585                 590

Ile Gln Lys Glu Ser Thr Leu His Leu Val Leu Arg Leu Arg Gly Gly
        595                 600                 605

Met Gln Ile Phe Val Lys Thr Leu Thr Gly Lys Thr Ile Thr Leu Glu
610                 615                 620

Val Glu Pro Ser Asp Thr Ile Glu Asn Val Lys Ala Lys Ile Gln Asp
625                 630                 635                 640

Lys Glu Gly Ile Pro Pro Asp Gln Gln Arg Leu Ile Phe Ala Gly Lys
                645                 650                 655

Gln Leu Glu Asp Gly Arg Thr Leu Ser Asp Tyr Asn Ile Gln Lys Glu
            660                 665                 670

Ser Thr Leu His Leu Val Leu Arg Leu Arg Gly Gly Val
        675                 680                 685

<210> SEQ ID NO 19
<211> LENGTH: 1626
<212> TYPE: DNA
```

<213> ORGANISM: Homo sapiens

<400> SEQUENCE: 19

```
ctttgtggtt tggtctcagg gaagtagcag gcgccggttg agagaactac ggccctgtcg      60
gaaggtaacc tccggtgcaa acgaccatcg gcggcaggcg agcggtacgc ttggcgtccg     120
ggccttcctg ggcccgtctg aggaaacttg ctgctcgagg ccaggctgcc taggacctgt     180
cccttttttc tatactggct cccacatccg gttttttct ccgggacggc ccttcggatg      240
cttgggccaa tgggaatcgc catttagggt gctccgccca ccgggtcgcg tagagcatcc     300
tggaagtcgt agtaaatctc tcgagagttc tctccgcacg cgggctggag aagcgggtcc     360
tacgcacgct ttgttgtcgc gctttgcctc cgtccttccc cctactcccg ccttacctga     420
cttccttttc ggaggaagat ccttgagcag ccgacgttgg gacaaaggat ttggagaaac     480
ccagggctaa agtcacgttt ttcctccttt aagacttacc tcaacacttc actccatggc     540
agttcccgag acccgcccta accacactat ttatatcaac aacctcaatg agaagatcaa     600
gaaggatgag ctaaaaaagt ccctgtacgc catcttctcc cagtttggcc agatcctgga     660
tatcctggta tcacggagcc tgaagatgag gggccaggcc tttgtcatct tcaaggaggt     720
cagcagcgcc accaacgccc tgcgctccat gcagggtttc cctttctatg acaaacctat     780
gcgtatccag tatgccaaga ccgactcaga tatcattgcc aagatgaaag gcaccttcgt     840
ggagcgggac cgcaagcggg agaagaggaa gcccaagagc caggagaccc cggccaccaa     900
gaaggctgtg caaggcgggg agccaccccc cgtggtgggg gctgtccagg ggcctgtccc     960
gggcatgccg ccgatgactc aggcgccccg cattatgcac acatgccggg ccagccgcc    1020
ctacatgccg cccctggta tgatcccccc gccaggcctt gcacctggcc agatcccacc    1080
aggggccatg ccccgcagc agcttatgcc aggacagatg ccccctgccc agcctctttc    1140
tgagaatcca ccgaatcaca tcttgttcct caccaacctg ccagaggaga ccaacgagct    1200
catgctgtcc atgcttttca tcagttccc tggcttcaag gaggtccgtc tggtacccgg    1260
gcggcatgac atcgccttcg tggagtttga caatgaggta caggcagggg cagctcgcga    1320
tgccctgcag ggctttaaga tcacgcagaa caacgccatg aagatctcct ttgccaagaa    1380
gtagcaccctt ttcccccat gcctgcccct tccctgttc tggggccacc ccttccccc     1440
ttggctcagc cccctgaagg taagtccccc cttgggggcc ttcttggagc cgtgtgtgag    1500
tgagtggtcg ccacacagca ttgtacccag agtctgtccc cagacattgc acctggcgct    1560
gttaggccgg aattaaagtg gcttttgag gtttggtttt tcacaaaaaa aaaaaaaaa     1620
aaaaaa                                                               1626
```

<210> SEQ ID NO 20
<211> LENGTH: 282
<212> TYPE: PRT
<213> ORGANISM: Homo sapiens

<400> SEQUENCE: 20

```
Met Ala Val Pro Glu Thr Arg Pro Asn His Thr Ile Tyr Ile Asn Asn
1               5                   10                  15

Leu Asn Glu Lys Ile Lys Lys Asp Glu Leu Lys Lys Ser Leu Tyr Ala
            20                  25                  30

Ile Phe Ser Gln Phe Gly Gln Ile Leu Asp Ile Leu Val Ser Arg Ser
        35                  40                  45

Leu Lys Met Arg Gly Gln Ala Phe Val Ile Phe Lys Glu Val Ser Ser
    50                  55                  60
```

Ala Thr Asn Ala Leu Arg Ser Met Gln Gly Phe Pro Phe Tyr Asp Lys
65                  70                  75                  80

Pro Met Arg Ile Gln Tyr Ala Lys Thr Asp Ser Asp Ile Ile Ala Lys
            85                  90                  95

Met Lys Gly Thr Phe Val Glu Arg Asp Arg Lys Arg Glu Lys Arg Lys
        100                 105                 110

Pro Lys Ser Gln Glu Thr Pro Ala Thr Lys Lys Ala Val Gln Gly Gly
            115                 120                 125

Gly Ala Thr Pro Val Val Gly Ala Val Gln Gly Pro Val Pro Gly Met
130                 135                 140

Pro Pro Met Thr Gln Ala Pro Arg Ile Met His His Met Pro Gly Gln
145                 150                 155                 160

Pro Pro Tyr Met Pro Pro Gly Met Ile Pro Pro Gly Leu Ala
                165                 170                 175

Pro Gly Gln Ile Pro Pro Gly Ala Met Pro Pro Gln Gln Leu Met Pro
            180                 185                 190

Gly Gln Met Pro Pro Ala Gln Pro Leu Ser Glu Asn Pro Pro Asn His
        195                 200                 205

Ile Leu Phe Leu Thr Asn Leu Pro Glu Glu Thr Asn Glu Leu Met Leu
210                 215                 220

Ser Met Leu Phe Asn Gln Phe Pro Gly Phe Lys Glu Val Arg Leu Val
225                 230                 235                 240

Pro Gly Arg His Asp Ile Ala Phe Val Glu Phe Asp Asn Glu Val Gln
                245                 250                 255

Ala Gly Ala Ala Arg Asp Ala Leu Gln Gly Phe Lys Ile Thr Gln Asn
            260                 265                 270

Asn Ala Met Lys Ile Ser Phe Ala Lys Lys
        275                 280

<210> SEQ ID NO 21
<211> LENGTH: 3774
<212> TYPE: DNA
<213> ORGANISM: Homo sapiens

<400> SEQUENCE: 21
ggctctggct gagaacatgg ccaatgacat tgatgagctc attggcattc ccttccccaa      60
ccacagcagt gaggtcctgt gcagcctcaa tgagcaacgg cacgatggcc tgctgtgtga     120
cgtgctcctg gtggtgcagg agcaggagta tcggacccac cgctccgtcc tggctgcctg     180
cagcaagtac ttcaagaagc ttttcacagc cggcacccta gccagccagc cctacgtcta     240
tgagatcgac tttgtccagc ctgaggctct ggctgctatc ctggagttcg cctacacctc     300
cacgctcacc atcaccgctg gcaatgtcaa gcacatcctc aacgcagcca ggatgctgga     360
gatccagtgc atcgtgaacg tgtgcctgga tcatggagag cctggggggg acgggggggg     420
ggaggatgac aaggaggacg atgacgacga cgaagatgat gatgatgagg aggacgaaga     480
ggaggaggag gaagaggagg aggatgacga tgatgacacg gaggactttg ctgaccaaga     540
aaacttgcct gaccccccag gacatcagct gccaccaaag cccttccaag acagaccatc     600
tcacagagaag gcctattcag acaccccccag ggacttccct gactccttcc aggctggcag     660
tcctggccat ctgggggtga tccgggactt ctccatcgaa tctctgctaa gggagaacct     720
gtaccccaag gccaacatcc ccgacaggag accctcctgt ctccattcg ccccggactt     780
ctttccacac ctctggccag gggacttcgg tgcctttgcc cagctgcctg agcagcccat     840

```
ggacagtggg ccactggatc tggtcatcaa gaatcggaag atcaaggagg aggagaagga    900
ggagctgccc ccaccccac cgccacccct ccctaatgac ttcttcaagg acatgttccc    960
tgacctgccg gggggcctc tgggacccat caaggcggag aacgactacg gtgcctatct    1020
caacttcctg agtgccaccc acctgggagg cctcttccca ccctggcccc tggtagaaga    1080
gcgcaagctg aagcccaagg cctctcagca gtgcccatc tgccacaaag tcatcatggg    1140
ggccgggaag ctgccgcggc acatgaggac ccataccggg gagaagccat acatgtgcac    1200
catctgcgag gtccgcttca ccaggcagga caagctgaaa atccacatgc ggaagcacac    1260
aggggagcgg ccctacctgt gcatccactg caacgccaag ttcgtgcaca actacgacct    1320
caagaaccac atgcgcatcc acacgggcgt gcggccctac cagtgcgagt tctgctacaa    1380
gagcttcacg cgctctgacc acctgcaccc ccacatcaag cgccagagct gccgcatggc    1440
acggccccga cgcggccgca agcctgctgc gtggagggcc gccagcctgc tcttcgggcc    1500
cggcggcccg gccccccgaca aggcggcctt cgtgatgccc cctgcgctgg gcgaggtggg    1560
cggccacctg ggcggcgcag ctgtgtgcct cccgggcccc agccccgcca agcacttcct    1620
ggcagcgccc aagggcgccc tgagcctgca agagctggag cggcagttcg aggagacaca    1680
gatgaagctg ttcgggcgcg cgcagctgga ggctgagagg aacgcggggg gcctcctggc    1740
cttcgcgctg gccgagaacg tggcggcggc gcggccctac ttcccgctgc ccgacccttg    1800
ggccgccggc ctggccggcc tccctgggct cgccggcctc aaccacgtgg cctccatgtc    1860
cgaagccaac aactaggctg gtccctgtcg gctccagccc accagccctc cagtccttct    1920
ccctccaggc ccactctacc ctaccccatg gatctgaact tttcatttta aaaacacaaa    1980
gggaaaatgg gaaaataata ataatactat cagtgatggc attttcccgg gctcctaaag    2040
cagctgcctc cttttgctgg tctgagacgg gcatcttttc ccaaaaggcc aggagcccgg    2100
gcctccctcc ctgtctctct ggctctcata tagaaacttg caccggccca tgccacaaag    2160
aactgggtgc ccaggggcac ttaggagctg ggtgagtcat gagggtcag ggggtggttg    2220 gcctggtgcc cagccagcca cagcaggagg aggtaggggc tgggcatgca ccttggttaa    2280
gccccacccc ctatggcaaa gtctctgcca acactcctct gagggctcat tttccagtct    2340
ccagtggccc cggggtcttt ttgagaacta cccacctgcc acatagaaag aaatgctctg    2400
ttggcaggga ggcctcctgg aaccagtcag gaaccaggct ctggaaggcc cgggccattt    2460
cttccctgac ctgtcctgtg accttgacag gtcagccctc tgtagctcag tgtcacctgg    2520
ctatggaagg ggctggtaac tgaggtttcc gccctccacc tctaaacaca tacacaccta    2580 tcccccaga gaatcacaga gatggtagaa gctttgtact ccccaagtcc atggggaaac    2640
agtttatctt tctggactta gttttatcac atccagctct atattagcat attagcatag    2700
gtgagaaata tggccagact agacagagat caggtcatca ggggagcttc cgagcttcag    2760
caaagcccac aggtagctct gcgaactcag aatgctaccc taccttccct gcaggccgct    2820
gttcatgtct ggactcctgg gggcgctatt taatgtttac cccatctccc agtgcccct    2880 ccaaggctgt gcagtgtctt ggggctctca gggccaacat cgaagagatg ggggccacct    2940
cttaacacct ggcaacagtc tcccctcatc ctgattcctg acaacagaca aaacaccggt    3000
ttctagggtt tatctgtttg ttttttgagt tgagggttcc tcagggcctt ggcattgcta    3060
gtgatggtcc cctttgctgt gtgagaaccc cctcaacccc ttcctcctcc ctctggggat    3120
gaagtgggag tatttggctc cccatttttg acaaaagggc tcagtgcagg gaggtggagg    3180
cctctgaggt ttgaagggct ctgtgagtta gagttgtcac atgttctcct ggttcttgaa    3240
```

```
tttgcagcag gtcctgaaaa ggaaggctct gctggccccg tgccttcctg accttctctc    3300
tccttccctc ccctctcttt tcttgccaag tttgctttgg tttctgagca gcccagagag    3360
gaggagggtt cgtccccagg gagagcccag ggctggagtc cccaatccct gtgctatggg    3420
cacaaagaga cttcagctct tcctgttgcc ttggctttt cctgagcaaa aacacaacaa     3480
acaaaaaggc cagagaagag cacagactct gtccctctca caactctcca gaagagaccc    3540
cctgattctt cacaccaccg gatgccactc cagccagcag gattgctaca cacccctct     3600 gttctcagaa gtcatctgcc tgggcagccg cctctcagat tcctgtcttc gtttcagaca    3660
cttttctctg aagcatgccc atgtccacca gccaacgtgc ccccgtgttc ccccccatca    3720
gccaagtgat tggggctgaa ccagacttta aagagagga aaaaaaaaaa aaaa            3774
```

<210> SEQ ID NO 22
<211> LENGTH: 619
<212> TYPE: PRT
<213> ORGANISM: Homo sapiens

<400> SEQUENCE: 22

```
Met Ala Asn Asp Ile Asp Glu Leu Ile Gly Ile Pro Phe Pro Asn His
1               5                   10                  15

Ser Ser Glu Val Leu Cys Ser Leu Asn Glu Gln Arg His Asp Gly Leu
            20                  25                  30

Leu Cys Asp Val Leu Leu Val Val Gln Glu Gln Glu Tyr Arg Thr His
        35                  40                  45

Arg Ser Val Leu Ala Ala Cys Ser Lys Tyr Phe Lys Lys Leu Phe Thr
    50                  55                  60

Ala Gly Thr Leu Ala Ser Gln Pro Tyr Val Tyr Glu Ile Asp Phe Val
65                  70                  75                  80

Gln Pro Glu Ala Leu Ala Ala Ile Leu Glu Phe Ala Tyr Thr Ser Thr
                85                  90                  95

Leu Thr Ile Thr Ala Gly Asn Val Lys His Ile Leu Asn Ala Ala Arg
            100                 105                 110

Met Leu Glu Ile Gln Cys Ile Val Asn Val Cys Leu Glu Ile Met Glu
        115                 120                 125

Pro Gly Gly Asp Gly Glu Glu Asp Lys Glu Asp Asp Asp
    130                 135                 140

Asp Glu Asp Asp Asp Asp Glu Glu Asp Glu Glu Glu Glu Glu Glu
145                 150                 155                 160

Glu Glu Asp Asp Asp Asp Thr Glu Asp Phe Ala Ser Gln Glu Asn
                165                 170                 175

Leu Pro Asp Pro Gln Asp Ile Ser Cys His Gln Ser Pro Ser Lys Thr
            180                 185                 190

Asp His Leu Thr Glu Lys Ala Tyr Ser Asp Thr Pro Arg Asp Phe Pro
        195                 200                 205

Asp Ser Phe Gln Ala Gly Ser Pro Gly His Leu Gly Val Ile Arg Asp
    210                 215                 220

Phe Ser Ile Glu Ser Leu Leu Arg Glu Asn Leu Tyr Pro Lys Ala Asn
225                 230                 235                 240

Ile Pro Asp Arg Arg Pro Ser Leu Ser Pro Phe Ala Pro Asp Phe Phe
                245                 250                 255

Pro His Leu Trp Pro Gly Asp Phe Gly Ala Phe Ala Gln Leu Pro Glu
            260                 265                 270

Gln Pro Met Asp Ser Gly Pro Leu Asp Leu Val Ile Lys Asn Arg Lys
```

```
                275                 280                 285
Ile Lys Glu Glu Lys Glu Glu Leu Pro Pro Pro Pro Pro Pro
        290                 295                 300

Phe Pro Asn Asp Phe Phe Lys Asp Met Phe Pro Asp Leu Pro Gly Gly
305                 310                 315                 320

Pro Leu Gly Pro Ile Lys Ala Glu Asn Asp Tyr Gly Ala Tyr Leu Asn
                325                 330                 335

Phe Leu Ser Ala Thr His Leu Gly Gly Leu Phe Pro Pro Trp Pro Leu
            340                 345                 350

Val Glu Glu Arg Lys Leu Lys Pro Lys Ala Ser Gln Gln Cys Pro Ile
                355                 360                 365

Cys His Lys Val Ile Met Gly Ala Gly Lys Leu Pro Arg His Met Arg
        370                 375                 380

Thr His Thr Gly Glu Lys Pro Tyr Met Cys Thr Ile Cys Glu Val Arg
385                 390                 395                 400

Phe Thr Arg Gln Asp Lys Leu Lys Ile His Met Arg Lys His Thr Gly
                405                 410                 415

Glu Arg Pro Tyr Leu Cys Ile His Cys Asn Ala Lys Phe Val His Asn
            420                 425                 430

Tyr Asp Leu Lys Asn His Met Arg Ile His Thr Gly Val Arg Pro Tyr
                435                 440                 445

Gln Cys Glu Phe Cys Tyr Lys Ser Phe Thr Arg Ser Asp His Leu His
        450                 455                 460

Arg His Ile Lys Arg Gln Ser Cys Arg Met Ala Arg Pro Arg Arg Gly
465                 470                 475                 480

Arg Lys Pro Ala Ala Trp Arg Ala Ala Ser Leu Leu Phe Gly Pro Gly
                485                 490                 495

Gly Pro Ala Pro Asp Lys Ala Ala Phe Val Met Pro Ala Leu Gly
            500                 505                 510

Glu Val Gly Gly His Leu Gly Gly Ala Ala Val Cys Leu Pro Gly Pro
                515                 520                 525

Ser Pro Ala Lys His Phe Leu Ala Ala Pro Lys Gly Ala Leu Ser Leu
        530                 535                 540

Gln Glu Leu Glu Arg Gln Phe Glu Glu Thr Gln Met Lys Leu Phe Gly
545                 550                 555                 560

Arg Ala Gln Leu Glu Ala Glu Arg Asn Ala Gly Gly Leu Leu Ala Phe
                565                 570                 575

Ala Leu Ala Glu Asn Val Ala Ala Arg Pro Tyr Phe Pro Leu Pro
            580                 585                 590

Asp Pro Trp Ala Ala Gly Leu Ala Gly Leu Pro Gly Leu Ala Gly Leu
        595                 600                 605

Asn His Val Ala Ser Met Ser Glu Ala Asn Asn
        610                 615

<210> SEQ ID NO 23
<211> LENGTH: 1950
<212> TYPE: DNA
<213> ORGANISM: Human papillomavirus type 16

<400> SEQUENCE: 23
atggctgatc ctgcaggtac caatgggaa gagggtacgg gatgtaatgg atggttttat       60
gtagaggctg tagtggaaaa aaaaacaggg gatgctatat cagatgacga gaacgaaaat      120
gacagtgata caggtgaaga tttggtagat tttatagtaa atgataatga ttatttaaca      180
```

```
caggcagaaa cagagacagc acatgcgttg tttactgcac aggaagcaaa acaacataga    240
gatgcagtac aggttctaaa acgaaagtat ttgggtagtc cacttagtga tattagtgga    300
tgtgtagaca ataatattag tcctagatta aaagctatat gtatagaaaa acaaagtaga    360
gctgcaaaaa ggagattatt tgaaagcgaa gacagcgggt atggcaatac tgaagtggaa    420
actcagcaga tgttacaggt agaagggcgc catgagactg aaacaccatg tagtcagtat    480
agtggtggaa gtgggggtgg ttgcagtcag tacagtagtg gaagtggggg agagggtgtt    540
agtgaaagac acactatatg ccaaacacca cttacaaata tttaaatgt actaaaaact     600
agtaatgcaa aggcagcaat gttagcaaaa tttaaagagt tatacggggt gagttttca     660
gaattagtaa gaccatttaa agtaataaaa tcaacgtgtt gcgattggtg tattgctgca    720
tttggactta cacccagtat agctgacagt ataaaaacac tattacaaca atattgttta    780
tatttacaca ttcaaagttt agcatgttca tggggaatgg ttgtgttact attagtaaga    840
tataaatgtg aaaaaatag agaaacaatt gaaaaattgc tgtctaaaact attatgtgtg    900
tctccaatgt gtatgatgat agagcctcca aaattgcgta gtacagcagc agcattatat    960
tggtataaaa caggtatatc aaatattagt gaagtgtatg agacacgcc agaatggata   1020
caaagacaaa cagtattaca acatagtttt aatgattgta catttgaatt atcacagatg   1080
gtacaatggg cctacgataa tgacatagta gacgatagtg aaattgcata taaatatgca   1140
caattggcag acactaatag taatgcaagt gcctttctaa aaagtaattc acaggcaaaa   1200
attgtaaagg attgtgcaac aatgtgtaga cattataaac gagcagaaaa aaaacaaatg   1260
agtatgagtc aatggataaa atatagatgt gataggtag atgatggagg tgattggaag   1320
caaattgtta tgttttaag gtatcaaggt gtagagttta tgtcattttt aactgcatta   1380
aaaagatttt tgcaaggcat acctaaaaaa aattgcatat tactatatgg tgcagctaac   1440
acaggtaaat cattatttgg tatgagttta atgaaatttc tgcaagggtc tgtaatatgt   1500
tttgtaaatt ctaaaagcca ttttttggtta caaccattag cagatgccaa ataggtatg   1560
ttagatgatg ctacagtgcc ctgttggaac tacatagatg acaatttaag aaatgcattg   1620
gatggaaatt tagtttctat ggatgtaaag catagaccat tggtacaact aaaatgccct   1680
ccattattaa ttacatctaa cattaatgct ggtacagatt ctaggtggcc ttatttacat   1740
aatagattgg tggtgtttac atttcctaat gagtttccat ttgacgaaaa cggaaatcca   1800
gtgtatgagc ttaatgataa gaactggaaa tcctttttct caaggacgtg gtccagatta   1860
agtttgcacg aggacgagga caaggaaaac gatggagact ctttgccaac gtttaaatgt   1920
gtgtcaggac aaaatactaa cacattatga                                      1950

<210> SEQ ID NO 24
<211> LENGTH: 649
<212> TYPE: PRT
<213> ORGANISM: Human papillomavirus type 16

<400> SEQUENCE: 24

Met Ala Asp Pro Ala Gly Thr Asn Gly Glu Glu Gly Thr Gly Cys Asn
1               5                   10                  15

Gly Trp Phe Tyr Val Glu Ala Val Val Glu Lys Lys Thr Gly Asp Ala
            20                  25                  30

Ile Ser Asp Asp Glu Asn Glu Asn Asp Ser Asp Thr Gly Glu Asp Leu
        35                  40                  45

Val Asp Phe Ile Val Asn Asp Asn Asp Tyr Leu Thr Gln Ala Glu Thr
    50                  55                  60
```

```
Glu Thr Ala His Ala Leu Phe Thr Ala Gln Glu Ala Lys Gln His Arg
 65                  70                  75                  80

Asp Ala Val Gln Val Leu Lys Arg Lys Tyr Leu Gly Ser Pro Leu Ser
             85                  90                  95

Asp Ile Ser Gly Cys Val Asp Asn Ile Ser Pro Arg Leu Lys Ala
            100                 105                 110

Ile Cys Ile Glu Lys Gln Ser Arg Ala Ala Lys Arg Arg Leu Phe Glu
        115                 120                 125

Ser Glu Asp Ser Gly Tyr Gly Asn Thr Glu Val Glu Thr Gln Gln Met
    130                 135                 140

Leu Gln Val Glu Gly Arg His Glu Thr Glu Thr Pro Cys Ser Gln Tyr
145                 150                 155                 160

Ser Gly Gly Ser Gly Gly Cys Ser Gln Tyr Ser Ser Gly Ser Gly
                165                 170                 175

Gly Glu Gly Val Ser Glu Arg His Thr Ile Cys Gln Thr Pro Leu Thr
            180                 185                 190

Asn Ile Leu Asn Val Leu Lys Thr Ser Asn Ala Lys Ala Ala Met Leu
        195                 200                 205

Ala Lys Phe Lys Glu Leu Tyr Gly Val Ser Phe Ser Glu Leu Val Arg
210                 215                 220

Pro Phe Lys Ser Asn Lys Ser Thr Cys Cys Asp Trp Cys Ile Ala Ala
225                 230                 235                 240

Phe Gly Leu Thr Pro Ser Ile Ala Asp Ser Ile Lys Thr Leu Leu Gln
                245                 250                 255

Gln Tyr Cys Leu Tyr Leu His Ile Gln Ser Leu Ala Cys Ser Trp Gly
            260                 265                 270

Met Val Val Leu Leu Leu Val Arg Tyr Lys Cys Gly Lys Asn Arg Glu
            275                 280                 285

Thr Ile Glu Lys Leu Leu Ser Lys Leu Leu Cys Val Ser Pro Met Cys
        290                 295                 300

Met Met Ile Glu Pro Pro Lys Leu Arg Ser Thr Ala Ala Ala Leu Tyr
305                 310                 315                 320

Trp Tyr Lys Thr Gly Ile Ser Asn Ile Ser Glu Val Tyr Gly Asp Thr
                325                 330                 335

Pro Glu Trp Ile Gln Arg Gln Thr Val Leu Gln His Ser Phe Asn Asp
            340                 345                 350

Cys Thr Phe Glu Leu Ser Gln Met Val Gln Trp Ala Tyr Asp Asn Asp
        355                 360                 365

Ile Val Asp Asp Ser Glu Ile Ala Tyr Lys Tyr Ala Gln Leu Ala Asp
        370                 375                 380

Thr Asn Ser Asn Ala Ser Ala Phe Leu Lys Ser Asn Ser Gln Ala Lys
385                 390                 395                 400

Ile Val Lys Asp Cys Ala Thr Met Cys Arg His Tyr Lys Arg Ala Glu
                405                 410                 415

Lys Lys Gln Met Ser Met Ser Gln Trp Ile Lys Tyr Arg Cys Asp Arg
            420                 425                 430

Val Asp Asp Gly Gly Asp Trp Lys Gln Ile Val Met Phe Leu Arg Tyr
        435                 440                 445

Gln Gly Val Glu Phe Met Ser Phe Leu Thr Ala Leu Lys Arg Phe Leu
    450                 455                 460

Gln Gly Ile Pro Lys Lys Asn Cys Ile Leu Leu Tyr Gly Ala Ala Asn
465                 470                 475                 480
```

```
Thr Gly Lys Ser Leu Phe Gly Met Ser Leu Met Lys Phe Leu Gln Gly
                485                 490                 495

Ser Val Ile Cys Phe Val Asn Ser Lys Ser His Phe Trp Leu Gln Pro
            500                 505                 510

Leu Ala Asp Ala Lys Ile Gly Met Leu Asp Asp Ala Thr Val Pro Cys
        515                 520                 525

Trp Asn Tyr Ile Asp Asp Asn Leu Arg Asn Ala Leu Asp Gly Asn Leu
    530                 535                 540

Val Ser Met Asp Val Lys His Arg Pro Leu Val Gln Leu Lys Cys Pro
545                 550                 555                 560

Pro Leu Leu Ile Thr Ser Asn Ile Asn Ala Gly Thr Asp Ser Arg Trp
                565                 570                 575

Pro Tyr Leu His Asn Arg Leu Val Val Phe Thr Phe Pro Asn Glu Phe
            580                 585                 590

Pro Phe Asp Glu Asn Gly Asn Pro Val Tyr Glu Leu Asn Asp Lys Asn
        595                 600                 605

Trp Lys Ser Phe Phe Ser Arg Thr Trp Ser Arg Leu Ser Leu His Glu
    610                 615                 620

Asp Glu Asp Lys Glu Asn Asp Gly Asp Ser Leu Pro Thr Phe Lys Cys
625                 630                 635                 640

Val Ser Gly Gln Asn Thr Asn Thr Leu
                645

<210> SEQ ID NO 25
<211> LENGTH: 252
<212> TYPE: DNA
<213> ORGANISM: Human papillomavirus type 16

<400> SEQUENCE: 25
atgacaaatc ttgatactgc atccacaaca ttactggcgt gcttttttgct ttgcttttgt     60 gtgcttttgt gtgtctgcct attaatacgt ccgctgcttt tgtctgtgtc tacatacaca    120
tcattaataa tattggtatt actattgtgg ataacagcag cctctgcgtt taggtgtttt    180
attgtatata ttatatttgt ttatatacca ttattttaa tacatacaca tgcacgcttt    240
ttaattacat aa                                                        252

<210> SEQ ID NO 26
<211> LENGTH: 83
<212> TYPE: PRT
<213> ORGANISM: Human papillomavirus type 16

<400> SEQUENCE: 26

Met Thr Asn Leu Asp Thr Ala Ser Thr Thr Leu Leu Ala Cys Phe Leu
1               5                   10                  15

Leu Cys Phe Cys Val Leu Leu Cys Val Cys Leu Leu Ile Arg Pro Leu
            20                  25                  30

Leu Leu Ser Val Ser Thr Tyr Thr Ser Leu Ile Ile Leu Val Leu Leu
        35                  40                  45

Leu Trp Ile Thr Ala Ala Ser Ala Phe Arg Cys Phe Ile Val Tyr Ile
    50                  55                  60

Ile Phe Val Tyr Ile Pro Leu Phe Leu Ile His Thr His Ala Arg Phe
65                  70                  75                  80

Leu Ile Thr

<210> SEQ ID NO 27
<211> LENGTH: 1596
```

```
<212> TYPE: DNA
<213> ORGANISM: Human papillomavirus type 16

<400> SEQUENCE: 27
atgcaggtga cttttatta catcctagtt attacatgtt acgaaaacga cgtaaacgtt      60
taccatattt ttttcagat gtctctttgg ctgcctagtg aggccactgt ctacttgcct     120
cctgtcccag tatctaaggt tgtaagcacg gatgaatatg ttgcacgcac aaacatatat    180
tatcatgcag aacatccag actacttgca gttggacatc cctatttttcc tattaaaaaa    240
cctaacaata acaaaatatt agttcctaaa gtatcaggat tacaatacag ggtatttaga   300
atacatttac ctgaccccaa taagtttggt tttcctgaca cctcatttta taatccagat   360
acacagcggc tggtttgggc ctgtgtaggt gttgaggtag gtcgtggtca gccattaggt   420
gtgggcatta gtggccatcc tttattaaat aaattggatg acacagaaaa tgctagtgct   480
tatgcagcaa atgcaggtgt ggataataga gaatgtatat ctatggatta caaacaaaca   540
caattgtgtt taattggttg caaaccacct ataggggaac actggggcaa aggatcccca   600
tgtaccaatg ttgcagtaaa tccaggtgat tgtccaccat tagagttaat aaacacagtt   660
attcaggatg tgatatggt tgatactggc tttggtgcta tggactttac tacattacag   720
gctaacaaaa gtgaagttcc actggatatt tgtacatcta tttgcaaata tccagattat   780
attaaaatgg tgtcagaacc atatggcgac agcttatttt tttatttacg aagggaacaa   840
atgtttgtta gacatttatt aataggggct ggtactgttg gtgaaaatgt accagacgat   900
ttatacatta aaggctctgg gtctactgca aattagcca gttcaaatta ttttcctaca    960
cctagtggtt ctatggttac ctctgatgcc caaatattca ataaacctta ttggttacaa   1020
cgagcacagg gccacaataa tggcatttgt tggggtaacc aactatttgt tactgttgtt   1080
gatactacac gcagtacaaa tatgtcatta tgtgctgcca tatctacttc agaaactaca   1140
tataaaaata ctaactttaa ggagtaccta cgacatgggg aggaatatga tttacagttt   1200
atttttcaac tgtgcaaaat aaccttaact gcagacgtta tgacatacat acattctatg   1260
aattccacta tttttggagga ctggaatttt ggtctacaac ctcccccagg aggcacacta   1320
gaagatactt ataggtttgt aacatcccag gcaattgctt gtcaaaaaca tacacctcca   1380
gcacctaaag aagatcccct taaaaaatac acttttggg aagtaaattt aaaggaaaag   1440
ttttctgcag acctagatca gtttcctta ggacgcaaat ttttactaca agcaggattg   1500
aaggccaaac caaaatttac attaggaaaa cgaaaagcta cacccaccac ctcatctacc   1560
tctacaactg ctaaacgcaa aaaacgtaag ctgtaa                              1596

<210> SEQ ID NO 28
<211> LENGTH: 531
<212> TYPE: PRT
<213> ORGANISM: Human papillomavirus type 16

<400> SEQUENCE: 28

Met Gln Val Thr Phe Ile Tyr Ile Leu Val Ile Thr Cys Tyr Glu Asn
1               5                   10                  15

Asp Val Asn Val Tyr His Ile Phe Phe Gln Met Ser Leu Trp Leu Pro
            20                  25                  30

Ser Glu Ala Thr Val Tyr Leu Pro Pro Val Pro Val Ser Lys Val Val
        35                  40                  45

Ser Thr Asp Glu Tyr Val Ala Arg Thr Asn Ile Tyr Tyr His Ala Gly
    50                  55                  60
```

Thr Ser Arg Leu Leu Ala Val Gly His Pro Tyr Phe Pro Ile Lys Lys
 65                  70                  75                  80

Pro Asn Asn Asn Lys Ile Leu Val Pro Lys Val Ser Gly Leu Gln Tyr
                 85                  90                  95

Arg Val Phe Arg Ile His Leu Pro Asp Pro Asn Lys Phe Gly Phe Pro
            100                 105                 110

Asp Thr Ser Phe Tyr Asn Pro Asp Thr Gln Arg Leu Val Trp Ala Cys
        115                 120                 125

Val Gly Val Glu Val Gly Arg Gly Gln Pro Leu Gly Val Gly Ile Ser
    130                 135                 140

Gly His Pro Leu Leu Asn Lys Leu Asp Asp Thr Glu Asn Ala Ser Ala
145                 150                 155                 160

Tyr Ala Ala Asn Ala Gly Val Asp Asn Arg Glu Cys Ile Ser Met Asp
                165                 170                 175

Tyr Lys Gln Thr Gln Leu Cys Leu Ile Gly Cys Lys Pro Pro Ile Gly
            180                 185                 190

Glu His Trp Gly Lys Gly Ser Pro Cys Thr Asn Val Ala Val Asn Pro
        195                 200                 205

Gly Asp Cys Pro Pro Leu Glu Leu Ile Asn Thr Val Ile Gln Asp Gly
    210                 215                 220

Asp Met Val Asp Thr Gly Phe Gly Ala Met Asp Phe Thr Thr Leu Gln
225                 230                 235                 240

Ala Asn Lys Ser Glu Val Pro Leu Asp Ile Cys Thr Ser Ile Cys Lys
                245                 250                 255

Tyr Pro Asp Tyr Ile Lys Met Val Ser Glu Pro Tyr Gly Asp Ser Leu
            260                 265                 270

Phe Phe Tyr Leu Arg Arg Glu Gln Met Phe Val Arg His Leu Phe Asn
        275                 280                 285

Arg Ala Gly Thr Val Gly Glu Asn Val Pro Asp Asp Leu Tyr Ile Lys
    290                 295                 300

Gly Ser Gly Ser Thr Ala Asn Leu Ala Ser Ser Asn Tyr Phe Pro Thr
305                 310                 315                 320

Pro Ser Gly Ser Met Val Thr Ser Asp Ala Gln Ile Phe Asn Lys Pro
                325                 330                 335

Tyr Trp Leu Gln Arg Ala Gln Gly His Asn Asn Gly Ile Cys Trp Gly
            340                 345                 350

Asn Gln Leu Phe Val Thr Val Val Asp Thr Thr Arg Ser Thr Asn Met
        355                 360                 365

Ser Leu Cys Ala Ala Ile Ser Thr Ser Glu Thr Thr Tyr Lys Asn Thr
    370                 375                 380

Asn Phe Lys Glu Tyr Leu Arg His Gly Glu Glu Tyr Asp Leu Gln Phe
385                 390                 395                 400

Ile Phe Gln Leu Cys Lys Ile Thr Leu Thr Ala Asp Val Met Thr Tyr
                405                 410                 415

Ile His Ser Met Asn Ser Thr Ile Leu Glu Asp Trp Asn Phe Gly Leu
            420                 425                 430

Gln Pro Pro Pro Gly Gly Thr Leu Glu Asp Thr Tyr Arg Phe Val Thr
        435                 440                 445

Ser Gln Ala Ile Ala Cys Gln Lys His Thr Pro Pro Ala Pro Lys Glu
    450                 455                 460

Asp Pro Leu Lys Lys Tyr Thr Phe Trp Glu Val Asn Leu Lys Glu Lys
465                 470                 475                 480

Phe Ser Ala Asp Leu Asp Gln Phe Pro Leu Gly Arg Lys Phe Leu Leu

```
                            485                 490                 495
Gln Ala Gly Leu Lys Ala Lys Pro Lys Phe Thr Leu Gly Lys Arg Lys
            500                 505                 510

Ala Thr Pro Thr Thr Ser Ser Thr Ser Thr Thr Ala Lys Arg Lys Lys
        515                 520                 525

Arg Lys Leu
    530
```

```
<210> SEQ ID NO 29
<211> LENGTH: 21
<212> TYPE: DNA
<213> ORGANISM: artificial
<220> FEATURE:
<223> OTHER INFORMATION: primer

<400> SEQUENCE: 29
catctgttct cagaaaccat a                                        21

<210> SEQ ID NO 30
<211> LENGTH: 24
<212> TYPE: DNA
<213> ORGANISM: artificial
<220> FEATURE:
<223> OTHER INFORMATION: primer

<400> SEQUENCE: 30
ggatttccgt tttcgtcaaa tgga                                     24

<210> SEQ ID NO 31
<211> LENGTH: 21
<212> TYPE: DNA
<213> ORGANISM: artificial
<220> FEATURE:
<223> OTHER INFORMATION: Oligonucleotide

<400> SEQUENCE: 31
aatagtaaca ctacacccat a                                        21

<210> SEQ ID NO 32
<211> LENGTH: 27
<212> TYPE: DNA
<213> ORGANISM: artificial
<220> FEATURE:
<223> OTHER INFORMATION: primer

<400> SEQUENCE: 32
catgataata tatgtttgtg cgtgcaa                                  27

<210> SEQ ID NO 33
<211> LENGTH: 20
<212> TYPE: DNA
<213> ORGANISM: artificial
<220> FEATURE:
<223> OTHER INFORMATION: primer

<400> SEQUENCE: 33
ctgtgtttct tyggtgccca                                          20

<210> SEQ ID NO 34
<211> LENGTH: 21
<212> TYPE: DNA
<213> ORGANISM: artificial
<220> FEATURE:
<223> OTHER INFORMATION: primer
```

```
<400> SEQUENCE: 34
gtgtactgca agcaacagtt a                                              21

<210> SEQ ID NO 35
<211> LENGTH: 24
<212> TYPE: DNA
<213> ORGANISM: artificial
<220> FEATURE:
<223> OTHER INFORMATION: primer

<400> SEQUENCE: 35
acaagacata catcgaccgg tcca                                           24

<210> SEQ ID NO 36
<211> LENGTH: 53
<212> TYPE: PRT
<213> ORGANISM: Human papillomavirus type 16

<400> SEQUENCE: 36

Met His Gln Lys Arg Thr Ala Met Phe Gln Asp Pro Gln Glu Arg Pro
1               5                   10                  15

Arg Lys Leu Pro Gln Leu Cys Thr Glu Leu Gln Thr Thr Ile His Asp
            20                  25                  30

Ile Ile Leu Glu Cys Val Tyr Cys Lys Gln Gln Leu Leu Arg Arg Glu
        35                  40                  45

Ile Ile Lys Asn Thr
    50

<210> SEQ ID NO 37
<211> LENGTH: 178
<212> TYPE: DNA
<213> ORGANISM: Human papillomavirus type 16

<400> SEQUENCE: 37
atgcaccaaa agagaactgc aatgtttcag gacccacagg agcgacccag aaagttacca     60
cagttatgca cagagctgca acaactata catgatataa tattagaatg tgtgtactgc    120
aagcaacagt tactgcgacg tgagatcatc aagaacacgt agagaaaccc agctgtaa     178

<210> SEQ ID NO 38
<211> LENGTH: 12
<212> TYPE: DNA
<213> ORGANISM: Human papillomavirus type 16

<400> SEQUENCE: 38
cgtgagatca tc                                                        12

<210> SEQ ID NO 39
<211> LENGTH: 6
<212> TYPE: PRT
<213> ORGANISM: Human papillomavirus type 16

<400> SEQUENCE: 39

Arg Arg Glu Ile Ile Lys
1               5

<210> SEQ ID NO 40
<211> LENGTH: 297
<212> TYPE: DNA
<213> ORGANISM: Human papillomavirus type 16

<400> SEQUENCE: 40
```

```
atgcatggag atacacctac attgcatgaa tatatgttag atttgcaacc agagacaact    60
gatctctact gttatgagca attaaatgac agctcagagg aggaggatga aatagatggt   120
ccagctggac aagcagaacc ggacagagcc cattacaata ttgtaacctt ttgttgcaag   180
tgtgactcta cgcttcggtt gtgcgtacaa agcacacacg tagacattcg tactttggaa   240
gacctgttaa tgggcacact aggaattgtg tgccccatct gttctcagaa accataa     297
```

<210> SEQ ID NO 41
<211> LENGTH: 97
<212> TYPE: PRT
<213> ORGANISM: Human papillomavirus type 16

<400> SEQUENCE: 41

```
Met His Gly Asp Thr Pro Thr Leu His Glu Tyr Met Leu Asp Leu Gln
1               5                   10                  15

Pro Glu Thr Thr Asp Leu Tyr Cys Tyr Glu Gln Leu Asn Asp Ser Ser
                20                  25                  30

Glu Glu Glu Asp Glu Ile Asp Gly Pro Ala Gly Gln Glu Pro Asp Arg
            35                  40                  45

Ala His Tyr Asn Ile Val Thr Phe Cys Cys Lys Cys Asp Ser Thr Leu
        50                  55                  60

Arg Leu Cys Val Gln Ser Thr His Val Asp Ile Arg Thr Leu Glu Asp
65                  70                  75                  80

Leu Leu Met Gly Thr Leu Gly Ile Val Cys Pro Ile Cys Ser Gln Lys
                85                  90                  95

Pro
```

<210> SEQ ID NO 42
<211> LENGTH: 21
<212> TYPE: DNA
<213> ORGANISM: artificial
<220> FEATURE:
<223> OTHER INFORMATION: primer

<400> SEQUENCE: 42

```
gatcagttgt ctctggttgc a                                              21
```

<210> SEQ ID NO 43
<211> LENGTH: 20
<212> TYPE: DNA
<213> ORGANISM: artificial
<220> FEATURE:
<223> OTHER INFORMATION: primer

<400> SEQUENCE: 43

```
gttctaawgt tgttccatac                                                20
```

<210> SEQ ID NO 44
<211> LENGTH: 21
<212> TYPE: DNA
<213> ORGANISM: artificial
<220> FEATURE:
<223> OTHER INFORMATION: primer

<400> SEQUENCE: 44

```
atagtatata gagatgggaa t                                              21
```

<210> SEQ ID NO 45
<211> LENGTH: 22
<212> TYPE: DNA
<213> ORGANISM: artificial

```
<220> FEATURE:
<223> OTHER INFORMATION: primer

<400> SEQUENCE: 45
gtcacacttg caacaraagg tt                                              22

<210> SEQ ID NO 46
<211> LENGTH: 22
<212> TYPE: DNA
<213> ORGANISM: artificial
<220> FEATURE:
<223> OTHER INFORMATION: primer

<400> SEQUENCE: 46
tttgcaacca gagacaactg at                                              22

<210> SEQ ID NO 47
<211> LENGTH: 21
<212> TYPE: DNA
<213> ORGANISM: artificial
<220> FEATURE:
<223> OTHER INFORMATION: primer

<400> SEQUENCE: 47
tccacaatas taataccaat a                                               21

<210> SEQ ID NO 48
<211> LENGTH: 21
<212> TYPE: DNA
<213> ORGANISM: artificial
<220> FEATURE:
<223> OTHER INFORMATION: primer

<400> SEQUENCE: 48
ccacaacatt actggcgtgc t                                               21

<210> SEQ ID NO 49
<211> LENGTH: 22
<212> TYPE: DNA
<213> ORGANISM: artificial
<220> FEATURE:
<223> OTHER INFORMATION: primer

<400> SEQUENCE: 49
ctactatgtc attatcgtag gc                                              22

<210> SEQ ID NO 50
<211> LENGTH: 20
<212> TYPE: DNA
<213> ORGANISM: artificial
<220> FEATURE:
<223> OTHER INFORMATION: primer

<400> SEQUENCE: 50
ggagacacgc cagaatggat                                                 20

<210> SEQ ID NO 51
<211> LENGTH: 26
<212> TYPE: DNA
<213> ORGANISM: artificial
<220> FEATURE:
<223> OTHER INFORMATION: primer

<400> SEQUENCE: 51
aggtaaccat agaaccacta ggtgta                                          26
```

<210> SEQ ID NO 52
<211> LENGTH: 23
<212> TYPE: DNA
<213> ORGANISM: artificial
<220> FEATURE:
<223> OTHER INFORMATION: primer

<400> SEQUENCE: 52
gacatttatt taatagggct ggt                                            23

<210> SEQ ID NO 53
<211> LENGTH: 26
<212> TYPE: DNA
<213> ORGANISM: artificial
<220> FEATURE:
<223> OTHER INFORMATION: primer

<400> SEQUENCE: 53
taggaccttc ggtgactgat gatcta                                         26

<210> SEQ ID NO 54
<211> LENGTH: 27
<212> TYPE: DNA
<213> ORGANISM: artificial
<220> FEATURE:
<223> OTHER INFORMATION: primer

<400> SEQUENCE: 54
gcaccagagg cagtaaccat gcccgca                                        27

<210> SEQ ID NO 55
<211> LENGTH: 21
<212> TYPE: DNA
<213> ORGANISM: artificial
<220> FEATURE:
<223> OTHER INFORMATION: primer

<400> SEQUENCE: 55
tcacgaagat ctgcattgtc a                                              21

<210> SEQ ID NO 56
<211> LENGTH: 20
<212> TYPE: DNA
<213> ORGANISM: artificial
<220> FEATURE:
<223> OTHER INFORMATION: primer

<400> SEQUENCE: 56
ggatctccgt ggggcggtga                                                20

<210> SEQ ID NO 57
<211> LENGTH: 23
<212> TYPE: DNA
<213> ORGANISM: artificial
<220> FEATURE:
<223> OTHER INFORMATION: primer

<400> SEQUENCE: 57
atgtggttct tgaggtcgta gtt                                            23

<210> SEQ ID NO 58
<211> LENGTH: 21
<212> TYPE: DNA
<213> ORGANISM: artificial
<220> FEATURE:
<223> OTHER INFORMATION: primer

<400> SEQUENCE: 58
atgtgcacca tctgcgaggt c                                                  21

<210> SEQ ID NO 59
<211> LENGTH: 21
<212> TYPE: DNA
<213> ORGANISM: artificial
<220> FEATURE:
<223> OTHER INFORMATION: primer

<400> SEQUENCE: 59
ggcccggcat gtggtgcata a                                                  21

<210> SEQ ID NO 60
<211> LENGTH: 23
<212> TYPE: DNA
<213> ORGANISM: artificial
<220> FEATURE:
<223> OTHER INFORMATION: primer

<400> SEQUENCE: 60
cagtatgcca agaccgactc aga                                                23

<210> SEQ ID NO 61
<211> LENGTH: 19
<212> TYPE: DNA
<213> ORGANISM: artificial
<220> FEATURE:
<223> OTHER INFORMATION: primer

<400> SEQUENCE: 61
cgacgtgagg tgtattaac                                                     19

<210> SEQ ID NO 62
<211> LENGTH: 19
<212> TYPE: DNA
<213> ORGANISM: artificial
<220> FEATURE:
<223> OTHER INFORMATION: primer

<400> SEQUENCE: 62
gcgacgtgag atcatcrag                                                     19

<210> SEQ ID NO 63
<211> LENGTH: 20
<212> TYPE: DNA
<213> ORGANISM: artificial
<220> FEATURE:
<223> OTHER INFORMATION: primer

<400> SEQUENCE: 63
tcctrcagat tcyaggtggc                                                    20

<210> SEQ ID NO 64
<211> LENGTH: 19
<212> TYPE: DNA
<213> ORGANISM: artificial
<220> FEATURE:
<223> OTHER INFORMATION: primer

<400> SEQUENCE: 64
tgatcctrca gcagcracg                                                     19

<210> SEQ ID NO 65

```
<211> LENGTH: 22
<212> TYPE: DNA
<213> ORGANISM: artificial
<220> FEATURE:
<223> OTHER INFORMATION: primer

<400> SEQUENCE: 65
tacatttaaa agatgtctct tt                                          22

<210> SEQ ID NO 66
<211> LENGTH: 21
<212> TYPE: DNA
<213> ORGANISM: artificial
<220> FEATURE:
<223> OTHER INFORMATION: primer

<400> SEQUENCE: 66
agayattatt gttatagtkt g                                           21

<210> SEQ ID NO 67
<211> LENGTH: 21
<212> TYPE: DNA
<213> ORGANISM: artificial
<220> FEATURE:
<223> OTHER INFORMATION: primer

<400> SEQUENCE: 67
agagcccatt acaatattgt a                                           21

<210> SEQ ID NO 68
<211> LENGTH: 20
<212> TYPE: DNA
<213> ORGANISM: artificial
<220> FEATURE:
<223> OTHER INFORMATION: primer

<400> SEQUENCE: 68
tgtctrcata cacatcatta                                             20

<210> SEQ ID NO 69
<211> LENGTH: 21
<212> TYPE: DNA
<213> ORGANISM: artificial
<220> FEATURE:
<223> OTHER INFORMATION: primer

<400> SEQUENCE: 69
gtacatttga mttatcacrg a                                           21

<210> SEQ ID NO 70
<211> LENGTH: 19
<212> TYPE: DNA
<213> ORGANISM: artificial
<220> FEATURE:
<223> OTHER INFORMATION: primer

<400> SEQUENCE: 70
aaggctctgg gyctactgc                                              19

<210> SEQ ID NO 71
<211> LENGTH: 19
<212> TYPE: DNA
<213> ORGANISM: artificial
<220> FEATURE:
<223> OTHER INFORMATION: primer

<400> SEQUENCE: 71
```

| | |
|---|---|
| atagatgccg cggaaggtc | 19 |

<210> SEQ ID NO 72
<211> LENGTH: 22
<212> TYPE: DNA
<213> ORGANISM: artificial
<220> FEATURE:
<223> OTHER INFORMATION: primer

<400> SEQUENCE: 72

| | |
|---|---|
| tcgcrgttct tgtttgtgga tc | 22 |

<210> SEQ ID NO 73
<211> LENGTH: 20
<212> TYPE: DNA
<213> ORGANISM: artificial
<220> FEATURE:
<223> OTHER INFORMATION: primer

<400> SEQUENCE: 73

| | |
|---|---|
| tccacatgcg gaagcacaca | 20 |

<210> SEQ ID NO 74
<211> LENGTH: 22
<212> TYPE: DNA
<213> ORGANISM: artificial
<220> FEATURE:
<223> OTHER INFORMATION: primer

<400> SEQUENCE: 74

| | |
|---|---|
| agaagaggaa gcccaagagc ca | 22 |

<210> SEQ ID NO 75
<211> LENGTH: 1163
<212> TYPE: DNA
<213> ORGANISM: Human papillomavirus type 16

<400> SEQUENCE: 75

| | |
|---|---|
| ctcctccgag cactcgctca cggcgtcccc ttgcctggaa agataccgcg gtccctccag | 60 |
| aggatttgag ggacagggtc ggaggggggct cttccgccag caccggagga agaaagagga | 120 |
| ggggctggct ggtcaccaga gggtggggcg gaccgcgtgc gctcggcggc tgcggagagg | 180 |
| gggagagcag gcagcgggcg gcggggagca gcatggagcc ggcggcgggg agcagcatgg | 240 |
| agccttcggc tgactggctg gccacggccg cggcccgggg tcgggtagag gaggtgcggg | 300 |
| cgctgctgga ggcgggggcg ctgcccaacg caccgaatag ttacggtcgg aggccgatcc | 360 |
| aggtcatgat gatgggcagc gcccgagtgg cggagctgct gctgctccac ggcgcggagc | 420 |
| ccaactgcgc cgaccccgcc actctcaccc gaccccgtgca cgacgctgcc cgggagggct | 480 |
| tcctggacac gctggtggtg ctgcaccggg ccggggcgcg gctggacgtg cgcgatgcct | 540 |
| ggggccgtct gcccgtggac ctggctgagg agctgggcca tcgcgatgtc gcacggtacc | 600 |
| tgcgcgcggc tgcgggggc accagaggca gtaaccatgc ccgcatagat gccgcggaag | 660 |
| gtccctcaga catccccgat tgaaagaacc agagaggctc tgagaaacct cgggaaactt | 720 |
| agatcatcag tcaccgaagg tcctacaggg ccacaactgc cccgccaca acccaccccg | 780 |
| ctttcgtagt tttcatttag aaaatagagc ttttaaaaat gtcctgcctt ttaacgtaga | 840 |
| tatatgcctt cccccactac cgtaaatgtc catttatatc attttttata tattcttata | 900 |
| aaaatgtaaa aagaaaaac accgcttctg ccttttcact gtgttggagt tttctggagt | 960 |

```
gagcactcac gccctaagcg cacattcatg tgggcatttc ttgcgagcct cgcagcctcc    1020
ggaagctgtc gacttcatga caagcatttt gtgaactagg gaagctcagg ggggttactg    1080
gcttctcttg agtcacactg ctagcaaatg gcagaaccaa agctcaaata aaataaaaat    1140
aattttcatt cattcactca aaa                                           1163
```

<210> SEQ ID NO 76
<211> LENGTH: 156
<212> TYPE: PRT
<213> ORGANISM: Human papillomavirus type 16

<400> SEQUENCE: 76

```
Met Glu Pro Ala Ala Gly Ser Ser Met Glu Pro Ser Ala Asp Trp Leu
1               5                   10                  15

Ala Thr Ala Ala Ala Arg Gly Arg Val Glu Val Arg Ala Leu Leu
            20                  25                  30

Glu Ala Gly Ala Leu Pro Asn Ala Pro Asn Ser Tyr Gly Arg Arg Pro
        35                  40                  45

Ile Gln Val Met Met Met Gly Ser Ala Arg Val Ala Glu Leu Leu Leu
    50                  55                  60

Leu His Gly Ala Glu Pro Asn Cys Ala Asp Pro Ala Thr Leu Thr Arg
65                  70                  75                  80

Pro Val His Asp Ala Ala Arg Glu Gly Phe Leu Asp Thr Leu Val Val
                85                  90                  95

Leu His Arg Ala Gly Ala Arg Leu Asp Val Arg Asp Ala Trp Gly Arg
            100                 105                 110

Leu Pro Val Asp Leu Ala Glu Glu Leu Gly His Arg Asp Val Ala Arg
        115                 120                 125

Tyr Leu Arg Ala Ala Ala Gly Gly Thr Arg Gly Ser Asn His Ala Arg
    130                 135                 140

Ile Asp Ala Ala Glu Gly Pro Ser Asp Ile Pro Asp
145                 150                 155
```

<210> SEQ ID NO 77
<211> LENGTH: 20
<212> TYPE: DNA
<213> ORGANISM: artificial
<220> FEATURE:
<223> OTHER INFORMATION: primer

<400> SEQUENCE: 77

```
tgatcctgca ggacgtggtc                                                 20
```

<210> SEQ ID NO 78
<211> LENGTH: 21
<212> TYPE: DNA
<213> ORGANISM: artificial
<220> FEATURE:
<223> OTHER INFORMATION: primer

<400> SEQUENCE: 78

```
ttagtatttt gtcctgacac a                                               21
```

<210> SEQ ID NO 79
<211> LENGTH: 365
<212> TYPE: PRT
<213> ORGANISM: Human papillomavirus type 16

<400> SEQUENCE: 79

```
Met Glu Thr Leu Cys Gln Arg Leu Asn Val Cys Gln Asp Lys Ile Leu
```

```
1               5                   10                  15
Thr His Tyr Glu Asn Asp Ser Thr Asp Leu Arg Asp His Ile Asp Tyr
                20                  25                  30

Trp Lys His Met Arg Leu Glu Cys Ala Ile Tyr Tyr Lys Ala Arg Glu
            35                  40              45

Met Gly Phe Lys His Ile Asn His Gln Val Val Pro Thr Leu Ala Val
        50                  55                  60

Ser Lys Asn Lys Ala Leu Gln Ala Ile Glu Leu Gln Leu Thr Leu Glu
65                  70                  75                  80

Thr Ile Tyr Asn Ser Gln Tyr Ser Asn Glu Lys Trp Thr Leu Gln Asp
                85                  90                  95

Val Ser Leu Glu Val Tyr Leu Thr Ala Pro Thr Gly Cys Ile Lys Lys
                100                 105                 110

His Gly Tyr Thr Val Glu Val Gln Phe Asp Gly Asp Ile Cys Asn Thr
            115                 120                 125

Met His Tyr Thr Asn Trp Thr His Ile Tyr Ile Cys Glu Glu Ala Ser
        130                 135                 140

Val Thr Val Val Glu Gly Gln Val Asp Tyr Tyr Gly Leu Tyr Tyr Val
145                 150                 155                 160

His Glu Gly Ile Arg Thr Tyr Phe Val Gln Phe Lys Asp Asp Ala Glu
                165                 170                 175

Lys Tyr Ser Lys Asn Lys Val Trp Glu Val His Ala Gly Gly Gln Val
            180                 185                 190

Ile Leu Cys Pro Thr Ser Val Phe Ser Ser Asn Glu Val Ser Ser Pro
        195                 200                 205

Glu Ile Ile Arg Gln His Leu Ala Asn His Pro Ala Ala Thr His Thr
210                 215                 220

Lys Ala Val Ala Leu Gly Thr Glu Glu Thr Gln Thr Thr Ile Gln Arg
225                 230                 235                 240

Pro Arg Ser Glu Pro Asp Thr Gly Asn Pro Cys His Thr Thr Lys Leu
                245                 250                 255

Leu His Arg Asp Ser Val Asp Ser Ala Pro Ile Leu Thr Ala Phe Asn
            260                 265                 270

Ser Ser His Lys Gly Arg Ile Asn Cys Asn Ser Asn Thr Thr Pro Ile
        275                 280                 285

Val His Leu Lys Gly Asp Ala Asn Thr Leu Lys Cys Leu Arg Tyr Arg
290                 295                 300

Phe Lys Lys His Cys Thr Leu Tyr Thr Ala Val Ser Ser Thr Trp His
305                 310                 315                 320

Trp Thr Gly His Asn Val Lys His Lys Ser Ala Ile Val Thr Leu Thr
                325                 330                 335

Tyr Asp Ser Glu Trp Gln Arg Asp Gln Phe Leu Ser Gln Val Lys Ile
            340                 345                 350

Pro Lys Thr Ile Thr Val Ser Thr Gly Phe Met Ser Ile
        355                 360                 365

<210> SEQ ID NO 80
<211> LENGTH: 1098
<212> TYPE: DNA
<213> ORGANISM: Human papillomavirus type 16

<400> SEQUENCE: 80
atggagactc tttgccaacg tttaaatgtg tgtcaggaca aaatactaac acattatgaa      60
aatgatagta cagacctacg tgaccatata gactattgga aacacatgcg cctagaatgt     120
```

```
gctatttatt acaaggccag agaaatggga tttaaacata ttaaccacca agtggtgcca      180
acactggctg tatcaaagaa taaagcatta caagcaattg aactgcaact aacgttagaa      240
acaatatata actcacaata tagtaatgaa aagtggacat tacaagacgt tagccttgaa      300
gtgtatttaa ctgcaccaac aggatgtata aaaaaacatg gatatacagt ggaagtgcag      360
tttgatggag acatatgcaa tacaatgcat tatacaaact ggacacatat atatatttgt      420
gaagaagcat cagtaactgt ggtagagggt caagttgact attatggttt atattatgtt      480
catgaaggaa tacgaacata ttttgtgcag tttaaagatg atgcagaaaa atatagtaaa      540
aataaagtat gggaagttca tgcgggtggt caggtaatat tatgtcctac atctgtgttt      600
agcagcaacg aagtatcctc tcctgaaatt attaggcagc acttggccaa ccacccgcc       660 gcgacccata ccaaagccgt cgccttgggc accgaagaaa cacagacgac tatccagcga      720
ccaagatcag agccagacac cggaaacccc tgccacacca ctaagttgtt gcacagagac      780
tcagtggaca gtgctccaat cctcactgca tttaacagct cacacaaagg acggattaac      840
tgtaatagta acactacacc catagtacat ttaaaaggtg atgctaatac tttaaaatgt      900
ttaagatata gatttaaaaa gcattgtaca ttgtatactg cagtgtcgtc tacatggcat      960
tggacaggac ataatgtaaa acataaaagt gcaattgtta cacttacata tgatagtgaa     1020
tggcaacgtg accaattttt gtctcaagtt aaaataccaa aaactattac agtgtctact     1080
ggatttatgt ctatatga                                                  1098

<210> SEQ ID NO 81
<211> LENGTH: 12
<212> TYPE: DNA
<213> ORGANISM: Human papillomavirus type 16

<400> SEQUENCE: 81
ctgcaggacg tg                                                          12

<210> SEQ ID NO 82
<211> LENGTH: 25
<212> TYPE: DNA
<213> ORGANISM: Artificial Sequence
<220> FEATURE:
<223> OTHER INFORMATION: Oligonucleotide

<400> SEQUENCE: 82
aattctaata cgactcacta taggg                                            25

<210> SEQ ID NO 83
<211> LENGTH: 19
<212> TYPE: DNA
<213> ORGANISM: Artificial Sequence
<220> FEATURE:
<223> OTHER INFORMATION: Oligonucleotide

<400> SEQUENCE: 83
atatactacg gatggcctg                                                   19
```

DIAGNOSTIC TRANSCRIPT AND SPLICE PATTERNS OF HPV16 IN DIFFERENT CERVICAL LESIONS

CROSS REFERENCE TO RELATED APPLICATIONS

This application is a 371 of PCT/EP2009/064811, filed Nov. 9, 2009 and claims the benefit of EP 08168608.1, filed Nov. 7, 2008, the contents of which is incorporated by reference herein in its entirety.

REFERENCE TO SEQUENCE LISTING

This application contains a Sequence Listing submitted as an electronic text file named "26784-US Sequence Listing.txt", having a size in bytes of 79 kb, and created on May 4, 2011. The information contained in this electronic file is hereby incorporated by reference in its entirety pursuant to 37 CFR §1.52(e)(5).

FILED OF INVENTION

The present invention relates to a method for differentiating in a subject with human papillomavirus 16 (HPV16) between (i) a severe form of HPV16 infection and (ii) a mild form of HPV16 infection based on determining the amount of a gene product (gene products) in a sample. Further envisaged by the present invention is a composition comprising an oligonucleotide mixture. Also envisaged by the present invention are kits and devices adapted to carry out the method of the present invention.

BACKGROUND OF THE INVENTION

Cancer of the uterine cervix (CxCa) is the second most common malignancy in women worldwide and is caused by high-risk human papillomaviruses with HPV16 being the most prevalent type. In developed countries, conventional cytological screening programs have substantially reduced the incidence of this kind of cancer. These cytological screening programs, however, have some drawbacks.

The Papanicolaou test, frequently also referred to as Pap test, is a diagnostic method designed for the detection of premalignant and malignant lesion in the uterine cervix. For the Papanicolaou test, samples are obtained from the cervix and screened by light microscopy for changes in cell morphology indicating malignant or premalignant cells. Then, samples are classified depending on the severity of the observed lesions. However, diagnosis by cervical cytology is a subjective method, and the quality depends on the standards of the laboratory that provides the service. As such, lesion categorization is only moderately reproducible and of poor sensitivity compared to colposcopy (Baldwin, P., R. Laskey, and N. Coleman. 2003. Translational approaches to improving cervical screening. Nat Rev Cancer 3:217-26). Moreover, false positive results lead to a high number of patients that are being over-treated.

Within the last two decades a variety of new diagnostic tests for HPV were developed. These methods are based on the detection of viral, molecular and biochemical markers, such as HPV proteins, DNA and RNA.

The FDA-approved Hybrid Capture II Test System (HC2) (formerly Digene Corp., USA, now Qiagen, Germany) is considered the gold standard for HPV DNA testing in clinical practice, however, it shows several disadvantages: a) no genotyping is performed, instead HPV infection is solely attributed to a "low-risk" or "high-risk" group, b) multiple infections cannot be identified, c) it is less sensitive for HPV detection than PCR-based methods (Birner et al. 2001. Mod. Pathol. 14:702-709), and d) it is modestly specific for predicting of cervical precancer and cancer risk. Some of its non-specificity for clinical end points can be ascribed to cross-reactivity with non-carcinogenic HPV genotypes (Castle, P. E., D. Solomon, C. M. Wheeler, P. E. Gravitt, S. Wacholder, and M. Schiffman. 2008. Human papillomavirus genotype specificity of hybrid capture 2. J Clin Microbiol 46:2595-604). Moreover, it only allows for the assessment whether a subject is infected with HPV or not. The test does not allow for assessing the severity of a HPV infection. Thus, once HPV has been diagnosed, further examinations are required.

Several PCR-based methods were developed within the last years, allowing a more precise detection of HPV infection. The majority of these PCR systems use consensus or general primers that bind to highly conserved regions of the HPV genome, e.g. in the L1 region.

The amplified PCR products are then subjected to further analysis (e.g. sequencing, restriction fragment length polymorphism (RFLP) analysis or hybridization) in order to identify specific mucosal HPV genotypes. Longitudinal cohort studies have shown that combined Pap and HPV testing exhibit better sensitivity and predict better long-term protection (among women with normal results of both tests) against CIN3 than cytological testing alone (Bulkmans, N. W., J. Berkhof, L. Rozendaal, F. J. van Kemenade, A. J. Boeke, S. Bulk, F. J. Voorhorst, R. H. Verheijen, K. van Groningen, M. E. Boon, W. Ruiting a, M. van Ballegooijen, P. J. Snijders, and C. J. Meijer. 2007. Human papillomavirus DNA testing for the detection of cervical intraepithelial neoplasia grade 3 and cancer: 5-year follow-up of a randomised controlled implementation trial. Lancet 370:1764-72, Hoyer, H., C. Scheungraber, R. Kuehne-Heid, K. Teller, C. Greinke, S. Leistritz, B. Ludwig, M. Durst, and A. Schneider. 2005. Cumulative 5-year diagnoses of CIN2, CIN3 or cervical cancer after concurrent high-risk HPV and cytology testing in a primary screening setting. Int J Cancer 116:136-43.). However, the high sensitivity of HPV PCR tests leads also to the identification of clinically not relevant infections or regressing lesions. Therefore, the positive predictive value (PPV) for the presence of an advanced lesion or the development of cervical cancer after an individual high-risk HPV DNA positive result is low. The resulting high proportion of test-positive but disease-negative diagnoses cause over-treatment, additional costs and considerable anxiety for women concerned (International Agency for Research on Cancer. 2005. Cervix Cancer Screening. IARC Press, Lyon).

Unlike HPV DNA testing, RNA detection allows the identification and analysis of transcriptionally active viruses. A recent introduction of preservation media for cervical smears that, apart from DNA and cell morphology, also conserves RNA, enhanced the development of RNA detection methods. To date, two commercial HPV RNA detection assays have been introduced: i) PreTect HPV Proofer® from BIOMERIEUX® (formerly NorChip) that detects early full-length mRNA targeting E6 and E7 sequences (E6/E7) from hrHPV types 16, 18, 31, 33 and 45, and ii) the Aptima® HPV test, a broad spectrum E6/E7 full-length mRNA amplification method from Gen-Probe®. Limited data from these tests indicate that testing for full-length HPV E6/E7 mRNA rather than HPV DNA alone only slightly increases the PPV for the development of cervical cancer and its precursors, while at the same time, sensitivity and thus the negative predictive value (NPV) is reduced (Cuschieri, K. S., M. J. Whitley, and H. A. Cubie. 2004. Human papillomavirus type specific DNA and RNA persistence—implications for cervical disease progression and monitoring. J Med Virol 73:65-70). The main disadvantage of these technologies refers to the fact that they cannot predict disease due to only qualitative measurement of a single full-length viral oncogene transcript. Moreover, cervical smears can comprise different amounts of HPV-infected cells that cannot be controlled for by these technologies.

The development of cervical cancer is closely linked to the integration of the HPV genome into the chromosome of the host cells. In low-grade lesions, the majority of HPV genomes are present in an episomal state, whereas in high-grade lesions and carcinoma, the HPV genome can be integrated into the host genome. However, it has been demonstrated that not in all cases of cervical carcinoma the HPV genome is present in an integrated form (Vinokurova, S., N. Wentzensen, I. Kraus, R. Klaes, C. Driesch, P. Melsheimer, F. Kisseljov, M. Durst, A. Schneider, and M. von Knebel Doeberitz. 2008. Type-dependent integration frequency of human papillomavirus genomes in cervical lesions. Cancer Res 68:307-13.). Integration of the HPV16 genome into the host genome is only found in app. 60% of cervical cancer cases. Thus, diagnostic means which determine only the integration status of the HPV genome are not reliable for risk stratification.

Colposcopy allows for examining the uterine cervix and vagina. By this visual examination, many premalignant lesions and malignant lesions in these areas can be detected. Due to its high reliability, colposcopy is regarded to be the goldstandard for diagnosing cervical diseases. This diagnostic procedure, however, is cost- and time-intensive. Colposcopy requires highly trained personnel and often involves an invasive procedure (biopsy with subsequent histologic analysis). Consequently, colposcopy cannot be used in cervical cancer precursor screening programs.

The technical problem underlying the present invention may be seen as the provision of means and methods for efficiently and reliably differentiating between mild and severe forms of HPV16 infection without the drawbacks as referred to above. Also, means and methods are required for a reliable risk stratification of subjects not having the HPV genome integrated into the genome. The technical problem is solved by the embodiments characterized in the claims and herein below.

BRIEF SUMMARY OF THE INVENTION

Accordingly, the present invention relates to a method for differentiating in a subject with HPV16 between (i) a severe form of HPV16 infection and (ii) a mild form of HPV16 infection, comprising the steps
a) determining the amount of a first gene product in a sample of said subject, said first gene product being a gene product of 880^2582,
b) determining the amount of a second gene product in a sample of said subject, said second gene product being selected from the group consisting of a gene product of 3632^5639, a gene product of 880^3358, a gene product of Apm1, a gene product of Ubc, a gene product of U1A, a gene product of E1, a gene product of E5, a gene product of L1 and a gene product of E6*I,
c) calculating a ratio of the amount of said first gene product as determined in step a) and the amount of said second gene product as determined in step b),
d) comparing the ratio as calculated in step c) to a reference ratio, and
e) differentiating between (i) a severe form of HPV16 infection and (ii) a mild form of HPV16 infection.

The method of the present invention, preferably, is an in vitro method. Moreover, it may comprise steps in addition to those explicitly mentioned above. For example, further steps may relate to sample pre-treatments or evaluation of the results obtained by the method. The method of the present invention preferably is used for differentiating between mild and severe form of HPV16 infection in subjects being infected with HPV16. However, the method of the present invention may also be used for monitoring, confirmation, and subclassification of said subject. The method may be carried out manually or assisted by automation. Preferably, steps (a), (b), (c), (d) and/or (e) may in total or in part be assisted by automation, e.g., by a suitable robotic and sensory equipment for the determination in steps (a) and (b), or a computer-implemented calculation step in step (e) or a computer-implemented comparison in step (d).

DETAILED DESCRIPTION OF THE INVENTION

The term "differentiating" as used herein means to distinguish between (i) a mild form of HPV16 infection and (ii) a severe form of HPV16 infection. The term as used herein, preferably, includes differentially diagnosing/detecting a mild and severe form of HPV16 infection.

As will be understood by those skilled in the art, the aforementioned differentiation is usually not intended to be correct for 100% of the subjects to be analyzed. The term, however, requires that the assessment will be valid for a statistically significant portion of the subjects to be analyzed. Whether a portion is statistically significant can be determined without further ado by the person skilled in the art using various well known statistic evaluation tools, e.g., determination of confidence intervals, p-value determination, Student's t-test, Mann-Whitney test, etc. Details are found in Dowdy and Wearden, Statistics for Research, John Wiley & Sons, New York 1983. Preferred confidence intervals are at least 90%, at least 95%, at least 97%, at least 98% or at least 99%. The p-values are, preferably, 0.1, 0.05, 0.01, 0.005, or 0.001. Preferably, the probability envisaged by the present invention allows that the differentiation will be correct for at least 60%, at least 70%, at least 80%, or at least 90% of the subjects of a given cohort.

The term "subject" as used herein relates to animals, preferably mammals, and, more preferably, humans. However, it is envisaged in accordance with the aforementioned method of the present invention that the subject shall be infected with HPV16. How to assess whether a subject is infected with HPV16 is well known in the art. E.g., HPV16 infection can be assessed by genotyping HPV16 DNA in a sample of a subject by Southern and dot blot hybridisation, in situ hybridisation, by signal amplification assays, or by various PCR methods (Molijn, A., B. Kleter, W. Quint, and L. J. van Doorn. 2005. Molecular diagnosis of human papillomavirus (HPV) infections. J Clin Virol 32 Suppl 1:S43-51).

The human papillomavirus is a DNA virus that infects the skin and mucous membranes. More than 100 HPV genotypes have been described (de Villiers, E. M., C. Fauquet, T. R. Broker, H. U. Bernard, and H. zur Hausen. 2004. Classification of papillomaviruses. Virology 324:17-27). HPV16 belongs to the high-risk HPV genotypes and is the main cause for the development of cervical cancer. It is also known that HPV16 can cause vulvar, anal, vaginal, penile and oropharyngeal cancer, as well as vaginal intraepithelial neoplasia, anal intraepithelial neoplasia, vulvar intraepithelial neoplasia, and penile intraepithelial neoplasia.

The HPV genome consists of a single molecule of double-stranded, circular closed DNA with approximately 7,906 base pairs (bp). The nucleic acid sequence of the HPV16 genome, HPV16R, is shown in SEQ ID NO: 1 (see. e.g. Myers, G., H. Delius, J. Icenogle, H. U. Bernard, M. Favre, M. van Ranst, and C. M. Wheeler. 1997. Human papillomaviruses 1997: a compilation and analysis of nucleic acid and amino acid sequences. Theoretical Biology and Biophysics, Los Alamos National Laboratory, Los Alamos, N. Mex.). Three open reading frames (ORF) are located on one strand. Three functional areas have been defined, the long control region (LCR), and the "early" and the "late" transcription regions. The LCR is an 850 bp long non-coding upstream region responsible for the regulation of DNA replication and transcription. It contains several binding sites for the viral E2 and other cellular transcription factors and a binding site for the viral E1 replication protein. Furthermore, it contains silencer as well as enhancer sequences and harbours the p97 core promoter close to the E6 ORF; it is the region of the highest degree of variation in the viral genome. The "early" region, consists of the ORF E1, E2, E4, E5, E6 and E7, which are involved in viral replication and cell transformation. The "late" region encodes the L1 and L2 structural proteins that form the viral capsid. Of the "early" proteins, the two most important HPV proteins for malignant diseases are E6 and E7, which act synergistically to transform cells from normal to immortal state. It is known in the art that the HPV16 transcriptom exhibits several splice donor (at nucleotide positions 226, 880, 1302 and 3632 of the HPV16R reference genome) and splice acceptor sites (at nucleotide positions 409, 526, 742, 2582, 2709, 3358 and 5639 of the HPV16R reference genome) resulting in at least 11 different splice junctions (Baker, C., and C. Calef. 1996. Maps of papillomavirus mRNA transcripts. Los Alamos National Laboratories, Los Alamos, N. Mex., USA.; Zheng, Z. M., and C. C. Baker. 2006. Papillomavirus genome structure, expression, and post-transcriptional regulation. Front Biosci 11:2286-302.). Splicing products are characterized herein based on the splice donor and acceptor sites used for generating the products. The respective splice donor and acceptor are separated by "^".

It is known in the art that infection with HPV16 can be subclassified in various manifestations. Cervical cancer develops from areas of persistent HPV infection through a series of well-defined stages that are histologically classified as cervical intraepithelial neoplasia 1 to 3 (CIN1 to CIN3). The stages of HPV progression are also cytologically known as low- and high-grade squamous intraepithelial lesions (LSIL and HSIL). LSIL is equivalent to CIN1, whereas CIN2 and CIN3, preferably, are equivalent to HSIL. Initial infection with HPV16 can lead to the development of CIN1 which is manifested by inhibition of normal differentiation in the lower third of the epithelium. The majority of these lesions regress spontaneously in immunocompetent individuals, probably mediated by cellular immunity. However, in some individuals there is a risk, e.g. due to inherited or induced immune deficiencies that the infection with HPV16 persists and that CIN1 lesions progress to a CIN2 lesion. A CIN2 lesion also shows a high regression rate, however, a CIN2 lesion may also progress to a high-grade disease (CIN3) which may progress to carcinoma (carcinoma in situ or even invasive) carcinoma.

The "mild form of HPV infection" as meant herein, preferably, refers to a form of HPV infection that is histologically classified as normal cervical tissue or as CIN1 (minimal or mild cervical dysplasia), or cytologically classified as NIL/M (negative for intraepithelial lesions or malignancy) or as LSIL (low-grade squamous intraepithelial lesions). Thus, the mild form of HPV infection, preferably, encompasses benign cervical lesions, and, thus, mild grade HPV lesions (for a review see Smith, J. H. 2002. Bethesda 2001. Cytopathology 13:4-10).

A "severe form of HPV infection" as meant herein, preferably, refers to a form of HPV infection that is histologically classified as CIN2 (moderate cervical epithelial dysplasia) or CIN3 (severe cervical dysplasia) or cancer (in situ or invasive). Accordingly, the term "severe form of HPV16 infection" preferably, refers to a form of HPV16 infection that is cytologically classified as HSIL or cancer. Thus, the severe form of HPV infection, preferably, encompasses malign cervical lesions, and, thus, high-grad HPV lesions (for a review see Smith, J. H. 2002. Bethesda 2001. Cytopathology 13:4-10).

A sample can be obtained by well known techniques and include samples from those cells, tissues or organs which express or produce the gene products referred to herein. Preferably, the samples scrapes or biopsies from the urogenital or the oropharyngeal tract. Such samples can be obtained by use of brushes, (cotton) swabs, spatula, rinse/wash fluids, punch biopsy devices, puncture of cavities with needles or surgical instrumentation. Preferably, the scrapes contain mucosal cells. More preferably, the sample is a cervical smear or Pap smear. Separated cells may be obtained from the body fluids or the tissues or organs by separating techniques such as filtration, centrifugation or cell sorting. Moreover, the sample may be further processed by well known methods in order to further enrich and/or purify the gene products as referred to herein. The further processing of a gene product, preferably, depends on the nature of the gene product, i.e. whether the gene product is a polypeptide or an RNA molecule. Preferably, if the gene product is a polypeptide, then polypeptides are enriched and/or purified by methods well known by the skilled person. Preferably, if the gene product is an mRNA molecule, then said RNA molecules may enriched and/or purified by methods well known in the art.

The term "gene product" as used herein, preferably, relates to a transcript, and thus to mRNA, or to a polypeptide.

The aforementioned method comprises the calculation of ratios of the amount of a first gene product and the amount of a second gene product. At least one amount that is used for the calculation of the ratio is the amount of a spliced mRNA of HPV16 (or a polypeptide encoded by the said spliced mRNA). As set forth herein below, the determination of the amount of spliced mRNAs of HPV16 (or a polypeptide encoded by the said spliced mRNA) is particularly advantageous for differentiating between mild and severe forms of HPV infection.

The aforementioned method, preferably, envisages the determination of the following ratios: the ratio of the amount of a gene product of 880^2582 (preferably, 880^2582 spliced mRNAs of HPV16R) and the amount of a gene product of 3632^5639, (preferably 3632^5639 spliced mRNAs of HPV16R), or the ratio of the amount of a gene product of 880^2582 (preferably, 880^2582 spliced mRNAs of HPV16R) and the amount of a gene product of 880^3358 (preferably, 880^3358 spliced mRNAs of HPV16R), or the ratio of the amount of a gene product of 880^2582 (preferably, 880^2582 spliced mRNAs of HPV16R) and the amount of a gene product of Apm1 (preferably, Apm1 mRNA), or the ratio of the amount of a gene product of 880^2582 (preferably, 880^2582 spliced mRNAs of HPV16R) and the amount of a gene product of Ubiquitin C (Ubc) (preferably Ubc mRNA), or the ratio of the amount of a gene product of 880^2582 (preferably, 880^2582 spliced mRNAs of HPV16R) and the amount of a gene product of U1A (preferably, U1A mRNA), or the ratio of the amount of a gene product of 880^2582 (preferably, 880^2582 spliced mRNAs of HPV16R) and the amount of a gene product of E1 (preferably E1 full-length mRNA of HPV16R), or the ratio of the amount of a gene product of 880^2582 (preferably, 880^2582 spliced mRNAs of HPV16R) and the amount of a gene product of E5 (preferably E5 full-length mRNA of HPV16R), or the ratio of the amount of a gene product of 880^2582 (preferably, 880^2582 spliced mRNAs of HPV16R) and the amount of a gene product of L1 (preferably L1 full-length mRNA of HPV16R), or the ratio of the amount of a gene product of 880^2582 (preferably, 880^2582 spliced mRNAs of HPV16R) and the amount of a gene product of 226^409 (preferably 226^409 spliced mRNAs (E6*I) of HPV16R).

The first gene product in the context of the aforementioned method of the present invention is, preferably, a gene product of 880^2582. Preferably, the term "gene product of 880^2582" refers to 880^2582 spliced mRNAs of HPV16R or to the E1C polypeptide. 880^2582 transcripts are alternatively spliced transcripts of HPV16R spliced at position 880 and 2582 (see below).

The E1C polypeptide is an N-terminally truncated variant of the E1 polypeptide of HPV and is thought to act as a trans-activator of LCR. The amino acid sequence of E1C of HPV16R is shown in SEQ ID NO: 2. The nucleic acid sequence encoding said E1C polypeptide of HPV16R is shown in SEQ ID NO: 3.

Preferably, 880^2582 spliced mRNAs are HPV mRNAs that comprise the 880^2582 splice junction. Thus, said mRNAs are mRNAs encoded by HPV16R that are the result of splicing the HPV16 transcript at nucleic acid position 880 (donor nucleotide) and 2582 (acceptor nucleotide) and connecting the donor nucleotide with the acceptor nucleotide. In the context of the present invention, the first number for spliced mRNAs, here 880, preferably, indicates the position of the donor nucleotide for splicing and thus the 5'-splice junction, whereas the second number, here 2582, indicates the position of the acceptor nucleotide for splicing, and, thus, the 3'-splice junction. The indicated positions are drawn to the 7906 bp genome of HPV16R as shown in SEQ ID NO: 1. It is known in the art that various mRNA species of HPV comprise 880^2582 spliced sequences such as species K-N, see FIG. 1. Accordingly, the determination of the amount of 880^2582 spliced mRNAs, preferably, encompasses the determination the cumulative amount of all 880^2582 containing mRNA species.

It is to be understood that the first gene product in the context of the present invention comprises the nucleic acid sequence that is generated by linking the 880 donor nucleotide to the 2582 acceptor nucleotide, and thus the sequence that comprises the splice junction after splicing. Accordingly, 880^2582 spliced mRNAs, preferably, comprise the said splice junction generated by splicing. Preferably, said spliced mRNAs comprise a nucleic acid sequence as shown in SEQ ID NO: 4.

Preferably, the E1C polypeptide is translated from/encoded by the polynucleotide that comprises the aforementioned splice junction. Accordingly, the E1C polypeptide of HPV16 preferably comprises an amino acid sequence as shown in SEQ ID NO: 5.

The second gene product in the context of the aforementioned method of the present invention, preferably, is selected from the group consisting of a gene product of 3632^5639, a gene product of 880^3358, a gene product of Apm1, a gene product of Ube, a gene product of U1A, a gene product of E1, a gene product of E5, a gene product of L1 and a gene product of E6*I.

The gene products of 3632^5639, of 880^3358 and of E6*1, preferably, are alternatively spliced mRNAs of HPV16 or polypeptides encoded by said alternatively spliced mRNA.

The term "gene product of 3632^5639" as used herein, preferably, refers to 3632^5639 spliced mRNAs of HPV16 or respective L1 polypeptide (encoded thereby), truncated by 26 amino acids, of HPV16 encoded by said 3632^5639 spliced mRNAs. The L1 polypeptide of HPV is a capsid protein. During late stages of the productive infection the major capsid protein, the L1 polypeptide is expressed in differentiated cells near the top of the epithelium and forms with L2 polypeptide of HPV16 the viral capsids in the granular layer. The amino acid sequence of the L1 polypeptide, truncated by 26 amino acids, encoded by said 3632^5639 spliced mRNAs is shown in SEQ ID NO: 6. The sequence of the polynucleotide encoding said L1 polypeptide is shown in SEQ ID NO: 7.

3632^5639 spliced mRNAs, preferably, comprise the nucleic acid sequence that is generated by linking the 3632 donor nucleotide to the 5639 acceptor nucleotide. Accordingly, 3632^5639 spliced mRNAs, preferably, comprise the said nucleic acid sequence with the splice junction. Preferably, said spliced mRNAs comprise a nucleic acid sequence as shown in SEQ ID NO: 8 (indicated are the corresponding DNA sequences).

The term "gene product of 880^3358" as used herein, preferably, refers to 880^3358 spliced mRNAs of HPV16 or the polypeptide of HPV encoded by said 880^3358 spliced mRNA, said polypeptide preferably being a fusion polypeptide of the N-terminus of the E1 polypeptide with the E4 polypeptide of HPV16. Said fusion polypeptide is frequently also referred to as E1^E4. Said polypeptide is expressed in the late phase of the viral life cycle. It is detected in the spinous and granular cell layers and has several functions late in infection of HPV16. The amino acid sequence of the fusion polypeptide is shown in SEQ ID NO:9. The nucleic acid sequence of encoding said fusion peptide is shown in SEQ ID NO: 10. The gene product of 880^3358 has been shown to be encoded by species A-D, and Q-S as shown in FIG. 1.

880^3358 spliced mRNAs, preferably, comprise the nucleic acid sequence that is generated by linking the 880 donor nucleotide to the 3358 acceptor nucleotide. Accordingly, 880^3358 spliced mRNAs, preferably, comprise the said nucleic acid sequence with the splice junction. Preferably, said spliced mRNAs comprise a nucleic acid sequence as shown in SEQ ID NO: 11. Accordingly, the E1^E4 fusion polypeptide of HPV16 preferably comprises an amino acid sequence as shown in SEQ ID NO: 12.

The term "gene product of E6*I" as used herein, preferably, refers to 226^409 spliced mRNAs of HPV16 or the E6*I polypeptide of HPV encoded by said 226^409 spliced mRNA. It has been suggested that E6*I polypeptide may transctivate the virus LCR (Alloul, N., and L. Sherman. 1999. Transcription-modulatory activities of differentially spliced cDNAs encoding the E2 protein of human papillomavirus type 16. J Gen Virol 80 (Pt 9):246'-70.). The amino acid sequence of the fusion polypeptide is shown in SEQ ID NO: 13. The nucleic acid sequence of encoding said fusion peptide is shown in SEQ ID NO: 14.

226^409 spliced mRNAs, preferably, comprise the nucleic acid sequence that is generated by linking the 226 donor nucleotide to the 409 acceptor nucleotide. Accordingly, 226^409 spliced mRNAs, preferably, comprise the said nucleic acid sequence. Preferably, said spliced mRNAs comprise a nucleic acid sequence as shown in SEQ ID NO: 15.

Accordingly, the E6*I polypeptide of HPV16 preferably comprises an amino acid sequence as shown in SEQ ID NO: 16.

Ubc, U1A, and Apm1 are genes that are comprised by the genome of the host cell. Thus, said genes are not encoded by the genome of HPV16. In the context of the present invention, the genes that are host-specific are also referred to as cellular genes. Gene products of Ubc, U1A and Apm1, preferably, are mRNAs and polypeptides encoded by the said genes. The method of the present invention, thus, contemplates the determination of the amount of the Ubc, U1A and Apm1 mRNAs or the Ubc, U1A and Apm1 polypeptides.

The term "Ubc" as meant herein, preferably, refers to ubiquitin C, preferably, human ubiquitin C. The nucleic acid sequence as well as the amino acid sequence of human Ubc1 are well known in the art and shown e.g. in GenBank Accession No: NM_021009.4 (nucleic acid sequence, SEQ ID NO: 17) and GenBank Accession No: NP_066289.2 (amino acid sequence, SEQ ID NO: 18).

The term U1A as meant herein, preferably, refers to U1 small nuclear ribonucleoprotein polypeptide A, preferably, human U1 small nuclear ribonucleoprotein polypeptide A. The nucleic acid sequence as well as the amino acid sequence of human U1A are well known in the art and shown e.g. in GenBank Accession No: NM_004596.3 (nucleic acid sequence, SEQ ID NO:19) and GenBank Accession No: NP_004587.1 (amino acid sequence, SEQ ID NO: 20).

The term Apm1 as meant herein, preferably, refers to "Affected by Papillomavirus DNA integration in ME180 cells" or "zinc finger and BTB domain containing 7C" (ZBTB7C). The nucleic acid sequence as well as the amino acid sequence of human Apm1 are well known in the art and shown e.g. in GenBank Accession No: NM_001039360.1 (nucleic acid sequence, SEQ ID NO: 21) and GenBank Accession No: NP_001034449.1 (amino acid sequence, SEQ ID NO: 22).

The method of the present invention also contemplates the determination of the amount of the polynucleotides comprising the E1 transcript or the determination of the amount of the E1 polypeptide. Said polynucleotides and said polypeptide are encoded by the HPV16 genome.

The E1 polypeptide is encoded by an unspliced E1 ORF (open reading frame)-containing transcript. E1 is essential for viral replication and shares structural similarities with the SV40 large tumour antigen. E1 exhibits ATPase, helicase and nucleotide-binding activities, interacts with the cellular DNA-polymerase a and recruits the cellular replication initiation machinery to the viral origin of replication in the LCR. The nucleic acid sequence of the E1 transcript is shown in SEQ ID NO: 23, the amino acid sequence of the E1 polypeptide is shown in SEQ ID NO: 24.

The method of the present invention also contemplates the determination of the amount of the polynucleotides comprising the E5 transcript or the determination of the amount of the E5 polypeptide. Said polynucleotides and said polypeptide are encoded by the HPV16 genome.

The E5 polypeptide is expressed from an unspliced E2/E5 transcript (particularly, species F-J, P, see FIG. 1), but not from the E1^E4/E5 transcript (species A-D, Q, R). Upon integration of the HPV16 genome into the host genome, E5 polypeptide and transcript expression ceases due to disruption of the E2 region. E5 is a hydrophobic membrane protein that is found in intracellular membranes and the plasma membrane. The E5 dimer is thought to be important in the early course of infection as it interacts with growth factor receptors, EGF- or PDGF-receptor, and causes their ligand-independent dimerisation followed by trans-phosphorylation of cytosolic tyrosine residues and recruitment of cellular signal transduction proteins. The nucleic acid sequence of the E5 transcript is shown in SEQ ID NO: 25, the amino acid sequence of the E5 polypeptide is shown in SEQ ID NO: 26.

The method of the present invention also contemplates the determination of the amount of the polynucleotides comprising the full length L1 transcript or the determination of the amount of the full-length L1 polypeptide. Said polynucleotides and said polypeptide are encoded by the HPV16 genome.

As set forth above, the L1 polypeptide of HPV is a capsid protein. During late stages of the productive infection the major capsid protein, the L1 polypeptide is expressed in differentiated cells near the top of the epithelium and forms with L2 polypeptide of HPV16 the viral capsids in the granular layer. The nucleic acid sequence of the full length L1 transcript is shown in SEQ ID NO: 27, the amino acid sequence of the full length L1 polypeptide is shown in SEQ ID NO: 28.

The determination of the amount of a gene product, preferably, depends on the nature of the gene product, i.e. whether the gene product is a transcript or a polypeptide.

Determining the amount of a transcript, and thus the amount of a mRNA, in a sample of a subject can be done by any method deemed appropriate.

Preferably, the amount of a transcript is determined by using a probe oligonucleotide that specifically detects the transcript to be analyzed.

The determination of the amount of a transcript or an amplification product thereof, by specific probe oligonucleotides, preferably, comprises the step of hybridizing a transcript or an amplification product (for an explanation of "amplification products", see below) thereof with probe oligonucleotides that specifically bind to the transcript or the amplification product thereof. A probe oligonucleotide in the context of the present invention, preferably, is a single-stranded nucleic acid molecule that is specific for said transcript or the amplification product thereof. The skilled person knows that a probe oligonucleotide comprises a stretch of nucleotides that specifically hybridizes with the target and, thus, is complementary to the target polynucleotide. Said stretch of nucleotides is, preferably, 85%, 90%, 95%, 99% or more preferably 100% identical to a sequence region comprised by a target polynucleotide.

In order to allow specific detection of a transcript or amplification product thereof, the probe oligonucleotide, preferably, specifically binds to the transcript or amplification product to be detected, but not to other polynucleotide comprised by said sample. How to choose suitable probe oligonucleotides is known in the art.

The probe oligonucleotides of the present invention may be labelled or contain other modifications including enzymes which allow a determination of the amount of a transcript or an amplification product thereof. Labelling can be done by various techniques well known in the art and depending of the label to be used. Preferred labels are described elsewhere in this specification.

The probe oligonucleotide may be bound to a solid surface or present in a liquid phase. As an example, the probe oligonucleotides are bound to a carrier providing a solid surface. Preferably, said carrier is a small particle or bead. The overall size of a small particle or bead, preferably, may be in the micrometer or nanometer range. Said beads and particles may be stained with a specific dye, more preferably with a specific fluorescent dye. Preferably, by staining various carriers with various dyes, the carries can be distinguished from each other. By using a carrier with a specific dye for a specific probe oligonucleotide (thus, a nucleic acid that targets the amplified polynucleotides of a specific sequence), said carrier is distinguishable from other carriers comprising different dyes. In one preferred embodiment commercially available LUMINEX® microspheres (LUMINEX® Corp., Austin, Tex., USA) are used. Thus, for detection of a transcript or amplification product thereof, the probes are coupled to fluorescence-labelled polystyrene beads (LUMINEX® suspension array technology) which are hybridized with the amplification products under suitable, preferably, stringent conditions. Moreover, the amplification products may be identified by use of microarrays, Reverse-Line Blots (RLB), Dot blots or similar technologies which contain specific oligonucleotides linked to a suitable carrier. Probe oligonucleotides present in a liquid phase may bind to immobilised target nucleic acid molecules or amplified polynucleotides. Specific labels or modifications known by persons skilled in the art may allow target detection or signal amplification. In addition, amplification products may be detected by size separation e.g. gel or capillary electrophoresis, by nucleotide composition, using e.g. Nuclear Magnetic Resonance, or by real-time and signal amplification methods as described elsewhere herein.

The person skilled in the art is able to select suitable probe oligonucleotides. For the determination of spliced transcripts, it is particularly contemplated to determine the amount of said alternatively spliced mRNAs by using probe oligonucleotides that specifically bind to the splice junction, and, thus bind the nucleic acid sequence that is generated by connecting the respective specific splice donor and splice acceptor nucleotide.

Accordingly, a probe oligonucleotide for the determination of 880^2582 spliced mRNAs, preferably, comprises a nucleic acid sequence as shown in SEQ ID NO: 4.

Moreover, a probe oligonucleotide for the determination of 3632^5639 spliced mRNAs, preferably, comprises a nucleic acid sequence as shown in SEQ ID NO: 8.

Also, a probe oligonucleotide for the determination of 880^3358 spliced mRNAs, preferably, comprises a nucleic acid sequence as shown in SEQ ID NO: 11.

Moreover, a probe oligonucleotide for the determination of E6*I transcripts, and thus of 226^409 spliced mRNAs, preferably, comprises a nucleic acid sequence as shown in SEQ ID NO: 15.

Preferred probe oligonucleotides for the determination of other transcripts as referred to herein are shown in Table 1.

Preferably, the determination of the amount of a transcript comprises the steps of amplifying the said transcript with oligonucleotides that specifically amplify said transcript and determining the amount of the, thus, amplified transcripts. Thus, for determination of the amount of a transcript, it is particularly preferred to amplify the transcript by suitable methods described elsewhere herein, and then to determine the amount of the amplification product. Alternatively, the determination of the amount of a transcript is achieved by signal amplification methods with oligonucleotide probes that specifically bind said transcript and allow linear signal amplification and subsequent determination of the amplified signal.

How to amplify a transcript is well known in the art. Amplification of a transcript, preferably, is a template-dependent process which results in an increase of the amount of a corresponding nucleic acid molecule relative to the initial amounts. The amplification product, preferably, is a nucleic acid, DNA or RNA. It is to be understood that amplification of a transcript may comprise additional steps such as reverse transcription of the transcript by well known methods.

How to amplify a target signal is well known in the art. Amplification of a signal, preferably, is a template-dependent process which results in an increase of the amount of a reporter signal relative to the initial amounts. The reporter signal, preferably, is a visible light, fluorescence, chemiluminescence, and luminescence. Methods for signal amplification are well-known in the art and may be based on tyramide signal amplification, branched DNA amplification, Dendrimer® amplification, padlock probes and rolling circle amplification, Invader® signal amplification and other signal amplification methods.

The amplification of a transcript of interest may be carried out by well-known methods, preferably by polymerase chain reaction (PCR), by reverse transcriptase PCR, real-time PCR, nucleic acid sequence-based amplification (NASBA), transcription-mediated amplification (TMA) and other isothermal amplification methods using polymerases and specific oligonucleotides as primers. PCR methods are well known in the art. Preferably, the amplification is by using suitable oligonucleotides pairs.

The current invention is not restricted to any of the aforementioned technologies. As an exemplary method for the amplification of transcripts, NASBA technology will be briefly summarised. NASBA is an oligonucleotide-dependent technology for the amplification of nucleic acids at one temperature. The sample comprising the transcript to be amplified is added to a reaction mixture comprising at least two transcript specific oligonucleotides for the amplification of said transcript. The first oligonucleotide, containing the T7 RNA promoter sequence, binds to its target site at the 3' end of the template. By reverse transcription a RNA/DNA hybrid is generated. The enzyme RNAse H degrades the RNA portion. After degradation of the RNA template, the second oligonucleotide binds to the 3'-end of the single-stranded cDNA and double-stranded DNA containing an intact T7 RNA promoter is generated. Then, the enzyme T7 RNA polymerase linearly generates antisense RNA. Each newly synthesized antisense RNA molecule can itself act as a template with the second primer and is converted to a DNA intermediate with a functional T7 promoter. However, in this case the oligonucleotide primers anneal in reverse order because the newly generated RNA molecules are opposite in orientation to the original target and the resulting DNA intermediate is only partly double-stranded. In this manner, many RNA copies are generated from each RNA target that re-enter the reaction resulting in the linear synthesis of RNA products under isothermal conditions. An approximately $10^6$- to $10^9$-fold amplification is obtained within 90 min (Compton, J. 1991. Nucleic acid sequence-based amplification. Nature 350:91-2).

In order to specifically amplify spliced mRNAs as referred to herein, the oligonucleotide pair for the amplification of the transcript, preferably, shall be capable to specifically amplify the nucleic acid region that comprises the respective splicing junction. Therefore, the oligonucleotides for the amplification shall specifically bind the transcript (or the complementary strand thereof, particularly a complementary DNA or RNA strand that is generated by approaches described elsewhere herein) 5' and 3' from the splicing junction (one primer 3', one primer 5'). An amplification product generated by using the aforementioned oligonucleotides will comprise the respective splice junction.

Accordingly, preferred oligonucleotides for the amplification of 880^2582 spliced mRNAs, preferably, comprise a nucleic acid sequence as shown in SEQ ID NO: 29 and in SEQ ID NO: 30.

Preferred oligonucleotides for the amplification of 3632^5639 spliced mRNAs, preferably, comprise a nucleic acid sequence as shown in SEQ ID NO: 31 and in SEQ ID NO: 32.

Preferred oligonucleotides for the amplification of 880'1358 spliced mRNAs, preferably, comprise a nucleic acid sequence as shown in SEQ ID NO: 29 and in SEQ ID NO: 33.

Preferred oligonucleotides for the amplification of E6*I transcripts, and thus of 226^409 spliced mRNAs, preferably, comprise a nucleic acid sequence as shown in SEQ ID NO: 34 and in SEQ ID NO: 34.

Preferred oligonucleotides for the amplification of other mRNAs as referred to herein are shown in Table 3.

Determining the amount of polynucleotides or amplification products referred to in this invention relates to measuring the amount or concentration, preferably semi-quantitatively or quantitatively. Preferably, the determination includes a normalization step for the quantification of transcripts. Exemplarily, this normalization process will be briefly described for NASBA target amplification method. Normalization and thus quantification is preferably achieved by adding a predefined amount of calibrator RNA (Q-RNA) to the amplification mixture. Said calibrator RNA, preferably, shall be in vitro-transcribed RNA that can be amplified by the same oligonucleotides that are capable of specifically amplifying the transcripts to be analyzed. However, said Q-RNAs shall comprise a specific target region for a probe oligonucleotide (i.e. a target region not comprised by the transcript to be analyzed). Said specific target region shall allow for differentiating between the amplification product of the transcript to be analyzed and the amplification product of the Q-RNA. The principle of the normalization is the competitive co-amplification of Q-RNA and the mRNA to be analyzed with the same oligonucleotide pair (van Gemen et al. 1993: Quantification of HIV-1 RNA in plasma using NASBA during HIV-1 primary infection. J Virol Methods 43:177-87). It is to be understood that Q-RNA amounts, preferably, need to be titrated for each mRNA to be analyzed in the context of the present invention. For quantification expression levels can be compared to a standard curve using in vitro transcribed mRNA or to suitable reference material. This can be done by the skilled person without further ado.

An oligonucleotide for the amplification of transcripts in the context of the present invention shall comprise a number of nucleotides being sufficient for specific binding to a sequence stretch of a target polynucleotide. Preferably, an oligonucleotide as meant herein has between 15 and 35 nucleotides in length, more preferably between 18 and 30 nucleotides in length, and most preferably between 20-27 nucleotides in length. A probe oligonucleotide in the context of the present invention allows detection of a transcript as referred to herein and/or amplification products of said transcript (see elsewhere herein). By detecting a transcript or an amplification product thereof, the amount of a specific transcript can be assessed in a sample of a subject with HPV16. In order to allow specific detection of a transcript or an amplification product thereof, the probe oligonucleotide has to be sufficiently complementary to the transcript or amplification product thereof, or to parts of said transcript or said amplification product. Particularly preferred oligonucleotides have the specific sequences and/or properties referred to herein.

Particularly, the oligonucleotides may be biotinylated in order to enable the binding of the amplification products to a streptavidin surface or fluorescent conjugate. Moreover, labels to be used in the context of the present invention may be, but are not limited to, fluorescent labels comprising, inter alia, fluorochromes such as R-phycoerythrin, Cy3, Cy5, fluorescein, rhodamin, Alexa, or Texas Red. However, the label may also be an enzyme or an antibody. It is envisaged that an enzyme to be used as a label will generate a detectable signal by reacting with a substrate. Suitable enzymes, substrates and techniques are well known in the art. An antibody to be used as label may specifically recognize a target molecule which can be detected directly (e.g., a target molecule which is itself fluorescent) or indirectly (e.g., a target molecule which generates a detectable signal, such as an enzyme). Moreover, the oligonucleotides may contain generic sequences that allow detection by hybridisation to complementary detector probes that may contain any of the aforementioned labels or modifications. The oligonucleotides of the present invention may also contain 5'-restriction sites, locked nucleic acid molecules (LNA) or be part of a peptide nucleic acid molecule (PNA). Such PNA can be, in principle, detected via the peptide part by, e.g., antibodies.

Also contemplated for the determination of the amount of a transcript (or an amplification product thereof) is the use of array-based techniques for determining the amount of transcripts in accordance with the present invention. An array as referred to herein is a system that comprises a solid support, e.g. a microarray with e.g. a small membrane, a nylon membrane, or glass slide, containing samples of various immobilized polynucleotides arranged in a regular pattern. Alternatively, a bead-array may consist of distinctly fluorescence-labelled microspheres or beads that allow multiplexing of probe oligonucleotides. The oligonucleotides probes, preferably represent genes, i.e. they consist of or comprise a nucleic acid sequence of the gene to be represented. By using an array many transcripts or genes can be determined, preferably, in a single experiment. With the aid of a suitable analyzer, such as an automatic reader device, the amount of target bound to the probes in the array can be precisely measured.

Determining the amount of peptides or polypeptides referred to in this specification relates to measuring the amount or concentration, preferably semi-quantitatively or quantitatively. Measuring can be done directly or indirectly. Direct measuring relates to measuring the amount or concentration of the peptide or polypeptide based on a signal which is obtained from the peptide or polypeptide itself and the intensity of which directly correlates with the number of molecules of the peptide present in the sample. Such a signal—sometimes referred to herein as intensity signal—may be obtained, e.g., by measuring an intensity value of a specific physical or chemical property of the peptide or polypeptide. Indirect measuring includes measuring of a signal obtained from a secondary component (i.e. a component not being the peptide or polypeptide itself) or a biological read out system, e.g., measurable cellular responses, ligands, labels, or enzymatic reaction products.

In accordance with the present invention, determining the amount of a peptide or polypeptide can be achieved by all known means for determining the amount of a peptide in a sample. Said means comprise immunoassay devices and methods which may utilize labelled molecules in various sandwich, competition, or other assay formats. Said assays will develop a signal which is indicative for the presence or absence of the peptide or polypeptide. Moreover, the signal strength can, preferably, be correlated directly or indirectly (e.g. reverse-proportional) to the amount of polypeptide present in a sample. Further suitable methods comprise measuring a physical or chemical property specific for the peptide or polypeptide such as its precise molecular mass or NMR spectrum. Said methods comprise, preferably, biosensors, optical devices coupled to immunoassays, biochips, analytical devices such as mass-spectrometers, NMR-analyzers, or chromatography devices. Further, methods include micro-plate ELISA-based methods, fully-automated or robotic immunoassays (available for example on Elecsys™ analyzers), CBA (an enzymatic Cobalt Binding Assay, available for example on Roche-Hitachi™ analyzers), and latex agglutination assays (available for example on Roche-Hitachi™ analyzers).

Determination of the amount of a polypeptide, preferably, comprises the use of antibodies that specifically bind to the polypeptide to be determined. Preferably, if the polypeptide to be determined is derived from the translation of a specifically spliced HPV transcript, than the antibody specifically shall bind to the region of the polypeptide that is encoded by the nucleic acids flanking the splice junction.

Preferably, for the determination of the amount of the E1C polypeptide (encoded by 880^2582 spliced mRNAs), the antibody shall specifically bind to a peptide having an amino acid sequence as shown in SEQ ID NO: 5.

Preferably, for the determination of the amount of the E6*I polypeptide (encoded by 226^409 spliced mRNAs), the antibody shall specifically bind to a peptide having an amino acid sequence as shown in SEQ ID NO: 16.

Preferably, for the determination of the amount of the E1^E4 fusion polypeptide (encoded by 880^3358 spliced mRNAs), the antibody shall specifically bind to a peptide having an amino acid sequence as shown in SEQ ID NO: 12.

The term "amount" as used herein encompasses the absolute amount of a gene product, the relative amount or concentration of the said gene product as well as any value or parameter which correlates thereto or can be derived therefrom. Such values or parameters comprise intensity signal values from all specific physical or chemical properties obtained from the said gene product by direct measurements. Moreover, encompassed are all values or parameters which are obtained by indirect measurements specified elsewhere in this description. E.g. for polypeptides response levels can be determined from biological read out systems in response to the peptides or intensity signals obtained from specifically bound ligands. It is to be understood that values correlating to the aforementioned amounts or parameters can also be obtained by all standard mathematical operations.

The term "comparing" as used herein encompasses comparing the value determined by calculating a ratio of the amount of a first gene product as determined in step a) of the methods of the present invention and the amount of said second gene product as determined in step b) of the methods of the present invention to a suitable reference source specified elsewhere in this description. It is to be understood that comparing as used herein refers to a comparison of values. The comparison referred to in step d) of the methods of the present invention may be carried out manually or computer-assisted. For a computer-assisted comparison, the value of the determined amount may be compared to values corresponding to suitable references which are stored in a database by a computer program. The computer program may further evaluate the result of the comparison, i.e. automatically provide the desired assessment in a suitable output format. Based on the comparison of the ratio calculated in step c) of the methods of the present invention to a reference ratio it is possible to differentiate, in a subject with HPV16, between a mild form of infection with HPV16 and a severe form of infection with HPV16. Therefore, the reference is to be chosen so that either a difference or a similarity in the compared values allows for differentiating between a mild form of infection with HPV16 and a severe form of infection with HPV16.

Accordingly, the term "reference" or "reference ratio" as used herein, preferably, refers to a value which allows differentiation between a mild form and a severe form of HPV16 infection. Accordingly, the reference may be derived from carrying out steps a) and b) of the methods of the present invention and calculating a ratio of the amount of a first gene product, in a sample of a subject with HPV16 infection, as determined in step a) of the method of the present invention, and the amount of said second gene product as determined in step b) of the method of the present invention, said subject being known to suffer from a severe form of HPV16 infection such as HSIL or cervical cancer. Also, the reference may be derived from carrying out steps a) and b) of the methods of the present invention and calculating a ratio of the amount of a first gene product, in a sample of a subject with HPV16 infection, as determined in step a) of the methods of the present invention and the amount of said second gene product, in a sample of a subject with HPV16 in a subject, as determined in step b) of the methods of the present invention, said subject being known to show exhibit a mild form of HPV16 infection (e.g. a form classified as LSIL). Moreover, the reference amounts, preferably, define thresholds. Suitable reference ratios or thresholds may be determined by the method of the present invention from a reference sample to be analyzed. together, i.e. simultaneously or subsequently, with the test sample. It is to be understood that the value of the reference or threshold may vary depending on the nature of the gene product (transcript or polypeptide) and depending on how the amount of a gene product is determined in the sample. For example, if the determination of the amount of the first and the second gene product includes amplification of the gene product by PCR (polymerase chain reaction), the determined amount of a gene product may depend, e.g., on the oligonucleotides used for the PCR reaction since the amplification efficiency of various oligonucleotide pairs for the amplification of a specific gene product varies. However, the person skilled in the art considers this when calculating the reference ratio. Particularly, the person skilled knows that, preferably, the same means and methods have to be used for determining the amounts of a specific gene product in a reference sample and in a test sample.

A preferred reference ratio serving as a threshold may be derived from the upper limit of normal (ULN), i.e. the upper limit of the physiological amount to be found in a population of subjects (e.g. patients enrolled for a clinical trial). The ULN for a given population of subjects can be determined by various well known techniques.

Preferably, the ratio calculated in the context of the present invention is the ratio of the amount of the first gene product to the amount of the second gene product. It is to be understood, that also the ratio of the amount of the second gene product to the first gene product can be calculated.

If the ratio of the amount of the first gene product to the amount of the second gene product is calculated, preferably, the following applies:

Preferably, a calculated ratio in the test sample larger than the reference ratio indicates a severe form of HPV infection. More preferably, a calculated ratio in the test sample significantly larger than the reference ratio indicates a severe form of HPV infection. Most preferably, a calculated ratio in the test sample that is statistically significantly larger than the reference ratio indicates a severe form of HPV infection. Preferred ratios indicating a severe form of HPV infection are shown in Table 5.

Preferably, a calculated ratio in the test sample lower than the reference ratio indicates a mild form of HPV infection. More preferably, a calculated ratio in the test sample significantly lower than the reference ratio indicates a mild form of HPV infection. Most preferably, said calculated ratio is statistically significantly lower than the reference ratio. Preferred ratios indicating a mild form of HPV infection are shown in Table 5.

Particularly, a ratio significantly larger (or lower) or statistically significantly larger (or lower) than a reference ratio is a ratio of a size which is considered to be significant for the differentiation referred to herein. The terms "larger", "significantly larger", and "statistically significantly larger", "lower", "significantly lower", and "statistically significantly lower" are known by the person skilled in the art. Thus, whether a ratio is larger (or lower), significantly larger (or lower) or statistically significantly larger (or lower) can be determined without further ado by the person skilled in the art using various well known statistic evaluation tools.

Preferably, a ratio of the amount of a first gene product to the amount of the second gene product in a test sample larger than the reference ratio indicates a severe form of HPV infection. Preferably, said first gene product is a gene product of 880^2582, preferably, 880^2582 spliced mRNA, preferably said second gene product is a gene product of 3632^5639, preferably, 3632^5639 spliced mRNA.

Preferably, a ratio of the amount of a first gene product to the amount of the second gene product in a test sample lower than the reference ratio indicates a mild form of HPV infection. Preferably, said first gene product is a gene product of 880^2582, preferably, 880^2582, preferably said second gene product is a gene product of 3632^5639, preferably, 3632^5639 spliced mRNA.

Preferred reference ratios with 880^2582 being the first gene product to the amount of other second gene products are summarised in Table 5.

Advantageously, it was shown that determining, in a sample of a subject with HPV16, the amount of a first gene product as indicated herein, and determining, in a sample of a subject the amount of a second gene product as indicated herein, calculating a ratio of said amount of said first gene product and said amount of said second gene product, and comparing said ratio to a reference is required for reliably differentiating between mild and severe forms of HPV16 infection. Particularly, the following ratios were calculated in a total of 80 samples of subjects with HPV suffering from mild forms or severe forms of HPV infection (see also Examples): the ratio of the amount of 880^2582 spliced mRNAs of HPV16 to the amount of 3632^5639 spliced mRNAs of HPV16, the ratio of the amount of 880^2582 spliced mRNAs of HPV16 to the amount of 880^3358 spliced mRNAs of HPV16, the ratio of the amount of 880^2582 spliced mRNAs of HPV16 to the amount of Apm1 mRNAs, the ratio of the amount of 880^2582 spliced mRNAs of HPV16 to the amount of Ubc mRNA, the ratio of the amount of 880^2582 spliced mRNAs of HPV16 to the amount of U1A mRNA, the ratio of the amount of 880^2582 spliced mRNAs of HPV16 to the amount of 3632^5639 spliced mRNAs of HPV16, the ratio of the amount of 880^2582 spliced mRNAs of HPV16 to the amount of E1 mRNA of HPV16, the ratio of the amount of 880^2582 spliced mRNAs of HPV16 to the amount of E1 mRNA of HPV16, the ratio of the amount of 880^2582 spliced mRNAs of HPV16 to the amount of E5 mRNA of HPV16, the ratio of the amount of 880^2582 spliced mRNAs of HPV16 to the amount of L1 mRNA of HPV16, the ratio of the amount of 880^2582 spliced mRNAs of HPV16 to the amount of 226^409 spliced mRNAs of HPV16. It was shown that the calculated ratios showed highly significant differences in progression from mild forms of HPV16 infection (particularly NIL/M) to severe forms of infection with HPV16, particularly cervical cancer. Particularly, it was observed that determining the expression level of spliced transcripts rather than determination of the amount of full-length ORF containing transcripts was indicative of the stage of HPV-associated disease (as indicated by the p-value). Moreover, the method of the present invention allows for differentiating between mild and severe forms of HPV infection with an increased specificity and sensitivity than those in the prior art.

In US20070154884, the expression level of E6 and/or E7 and expression level of E2 and/or L1 and a ratio of E6 and/or E7 to L1 and/or E2 were determined, wherein a ratio of greater than 2 is indicative of HPV-induced cell transformation and risk of neoplasia. Similarly, WO/2001/073135 and WO/2003/057914 describe methods for determining the progression of human papillomavirus infection by detecting the presence or absence of transcripts of the E6, E7 or E6/E7 region and the presence or absence of transcripts of the L1, L2 or L1/L2 region of the human papillomavirus wherein the absence of transcripts of the E6, E7 or E6/E7 region and the absence of transcripts of the L1, L2 or L1/L2 region signifies no human papillomavirus infection; the presence of transcripts of the E6, E7 or E6/E7 region and the presence of transcripts of the L1, L2 or L1/L2 region signifies an early stage human papillomavirus infection and the presence of transcripts of the E6, E7 or E6/E7 region and the absence of transcripts of the L1, L2 or L1/L2 region signifies a late stage human papillomavirus infection.

According to the data presented in the present invention, it is possible to make a clinically useful assessment of HPV-associated disease based on determining the expression level of spliced transcripts rather than determination of the amount of full-length ORF containing transcripts being more indicative of the stage of HPV-associated disease (table 6, as indicated by the p-value). Preferably, in an indicative ratio of two gene products at least one is the spliced transcript 880^2582; and most preferably both gene products are derived from spliced transcripts. This method is technically simple and, in a preferred embodiment, is amenable to automation in a high-throughput format. Furthermore, on the basis of results obtained using the method of the present invention a novel scheme for classification of patients was defined on the basis of risk of developing high-grade lesions or cervical carcinoma which is related to disease-relevant molecular changes in the pattern of HPV gene expression (FIG. 8, Example 8).

Thus, the method of the present invention is particularly advantageous since it allows for rapid, reliable, inexpensive differentiation between mild and severe forms of HPV infection. Particularly, the method allows for identifying those subjects which are at elevated risk and, thus, which are in need for a cancer therapy and/or being susceptible to a cancer examination, particularly colposopic and histological examination and potentially therapy. Moreover, the method allows for identifying those subject suffering only from mild forms of HPV infection, and which are not in need for additional intensive examination and therapy. Without applying the method of the present invention, the said subjects might have been examined and treated too much (resulting in an increased risk of adverse side effects and increased health care cost).

The definitions made with regard to the aforementioned method apply mutatis mutandis to the following, unless stated otherwise.

Moreover, the present invention relates to a method for differentiating in a subject with HPV16 between (i) a severe form of HPV16 infection and (ii) a mild form of HPV16 infection, comprising the steps
   a) determining the amount of a first gene product in a sample of said subject, said first gene product being a gene product of E6*II,
   b) determining the amount of a second gene product in a sample of said subject, said second gene product being selected from the group consisting of a gene product of Apm1, a gene product of Ubc, a gene product of U1A, a gene product of 880^1358, and a gene product of E5,
   c) calculating a ratio of the amount of said first gene product as determined in step a) and the amount of said second gene product as determined in step b),
   d) comparing the ratio as calculated in step c) with a reference ratio, and
   e) differentiating between (i) a severe form of HPV16 infection and (ii) a mild form of HPV16 infection.

The aforementioned method, preferably, envisages the calculation of the following ratios: the ratio of the amount of a gene product of E6*II (preferably, 226^526 spliced mRNAs of HPV16) and the amount of a gene product of Apm1 (preferably, Amp1 mRNA), or the ratio of the amount of a gene product of E6*II (preferably, 226^526 spliced mRNAs of HPV16) and the amount of a gene product of Ubc (preferably, Ubc mRNA), or the ratio of the amount of a gene product of E6*II (preferably, 226^526 spliced mRNAs of HPV16) and the amount of a gene product of E5 (preferably, unspliced E5 mRNA), or the ratio of the amount of a gene product of E6*II (preferably, 226^526 spliced mRNAs of HPV16) and the amount of a gene product of 880^2709 (preferably, 880^2709 spliced mRNAs), or the ratio of a gene product of E6*II (preferably, 226^526 spliced mRNAs of HPV16) and the amount of a gene product of 880^3358 (preferably, 880^3358 spliced mRNAs).

The term "gene product of E6*II" as used herein, preferably, refers to 226^526 spliced mRNAs of HPV16 or the E6*II polypeptide of HPV16 encoded by said 226^526 spliced mRNAs. Preferably, mRNA species C, H, M (please see FIG. 1) comprised the 226^526 splice junction.

The amino acid sequence of the E6*II polypeptide is shown in SEQ ID NO: 36. The nucleic acid sequence encoding said E6*II polypeptide is shown in SEQ ID NO: 37.

226^526 spliced mRNAs, preferably, comprise the nucleic acid that is generated by linking the 226 donor nucleotide to the 526 acceptor nucleotide. Accordingly, 226^526 spliced mRNAs, preferably, comprise the said nucleic acid sequence. Accordingly, said spliced mRNAs comprise a nucleic acid sequence as shown in SEQ ID NO: 38. Accordingly, the E6*II polypeptide of HPV16 preferably comprises an amino acid sequence as shown in SEQ ID NO: 39.

Using target amplification methods, e.g. PCR or NASBA, the amount of a gene product of E6*I can be detected simultaneously to the detection of a gene product of E6*II by using E6*II specific oligonucleotide primers binding 5' of the 226 donor nucleotide and 3' of the 526 acceptor nucleotide (compare FIG. 1). Thus, E6*II oligonucleotide primers, described in the present invention are also able to anneal to and amplify the resulting 263 nucleotide long fragment of the E6*I transcript. E6*I transcript fragments amplified by E6*II primers can be detected by E6*I specific oligonucleotide probes.

The polypeptide E7 is translated from alternatively spliced E6*I mRNA (species B, G, L, see FIG. 1) and probably from alternatively spliced E6*II mRNA (species C, H, M, see FIG. 1) that all use the splice donor site at nt 226 and the splice acceptor site at nt 409 or nt 526, respectively. It is also thought that E7 is translated from full-length E6/E7 mRNA by leaky scanning. E7 is a nuclear protein and promotes the $G_1$-to-S phase progression in infected cells. It acts by binding to the retinoblastoma tumour suppressor protein (pRB) and supports its ubiquitination followed by degradation. Upon E7 binding, the pRB-mediated inhibition of E2F transcription factor is ceased and released E2F induces the expression of several proteins that stimulate entry in the S-phase of the cell cycle and lead to cell replication. In addition, E7 inhibits the function of cyclin-dependent kinase inhibitors, p21 and p27 and stimulates the S-phase genes cyclin A, and cyclin E. The nucleic acid sequence of the polynucleotide encoding the E7 polypeptide is shown in SEQ ID NO: 40. The amino acid sequence of the E7 polypeptide is shown in SEQ ID NO: 41.

The polypeptide E6*I can be translated from alternatively spliced E6*I mRNA (species B, G, L, see FIG. 1), while the polypeptide E6*II can be translated from alternatively spliced E6*II mRNA (species C, H, M, see FIG. 1). It is thought that the E6*I polypeptide may act as a trans-activator of the HPV LCR. No function has been assigned to the E6*II polypeptide so far. The amino acid sequence of the E6*I polypeptide is shown in SEQ ID NO: 13. The amino acid sequence of the E6*II polypeptide is shown in SEQ ID NO: 36.

Preferably, for the determination of the amount of the E6*II polypeptide (encoded by 226^526) spliced mRNAs, the antibody shall specifically bind a peptide having an amino acid sequence as shown in SEQ ID NO: 39.

Moreover, a probe oligonucleotide for the determination of the amount of 226^526 spliced mRNAs, and thus E6*II mRNA, preferably, comprises a nucleic acid sequence as shown in SEQ ID NO: 38.

Preferred oligonucleotides for the amplification of 226^526 spliced mRNAs, preferably, comprise a nucleic acid sequence as shown in SEQ ID NO: 34 and in SEQ ID NO: 42.

Preferred antibodies for the determination of the amount of the other polypeptides referred to in the context of the aforementioned method, preferred probe oligonucleotides for the determination of the amount of other mRNAs, and preferred oligonucleotides for the amplification of other mRNAs are described elsewhere herein (Table 1, Table 3, Table 7).

The term "gene product of 880ˆ2709" as used herein, preferably, encompasses 880ˆ2709 spliced mRNAs of HPV16 and the E2 polypeptide of HPV16 encoded by said 880ˆ2709 spliced mRNAs.

The amino acid sequence of the E2 polypeptide is shown in SEQ ID NO: 79. The nucleic acid sequence encoding said E2 polypeptide is shown in SEQ ID NO: 80.

880ˆ2709 spliced mRNAs, preferably, comprise the nucleic acid sequence that is generated by linking the 880 donor nucleotide to the 2709 acceptor nucleotide. Accordingly, 880ˆ2709 spliced mRNAs, preferably, comprise the said nucleic acid sequence with the splice junction. Preferably, said spliced mRNAs comprise a nucleic acid sequence as shown in SEQ ID NO: 81.

Preferably, the ratio of the amount of the first gene product to the amount of the second gene product is determined. For said ratio a calculated ratio in the test sample larger than the reference ratio, preferably, indicates a severe form of HPV infection. More preferably, a calculated ratio in the test sample significantly larger than the reference ratio indicates a severe form of HPV infection. Most preferably, said calculated ratio is statistically significantly larger than the reference ratio. Preferred ratios indicating a severe form of HPV infection are shown in Table 5.

Preferably, a calculated ratio (of the amount of the first gene product to the amount of the second gene product) in the test sample lower than the reference ratio indicates a mild form of HPV infection. More preferably, a calculated ratio in the test sample significantly lower than the reference ratio indicates a mild form of HPV infection. Most preferably, said calculated ratio is statistically significantly lower than the reference ratio. Preferred ratios indicating a mild form of HPV infection are shown in Table 5.

Advantageously, it was shown that determining, in a sample of a subject with HPV16, the amount of a first gene product as indicated herein, and determining, in a sample of a subject the amount of a second gene product as indicated herein, calculating a ratio of said amount of said first gene product and said amount of said second gene product, and comparing said ratio to a reference is required for reliably differentiating between mild and severe forms of HPV16 infection. Particularly, the following ratios were calculated in a total of 80 samples of subjects with HPV suffering from mild forms or severe forms of HPV infection (see also Examples): the ratio of the amount of 226ˆ526 spliced mRNAs of HPV16 to the amount of Apm1 mRNAs, the ratio of the amount of 226ˆ526 spliced mRNAs of HPV16 to the amount of Ubc mRNAs, the ratio of the amount of 226ˆ526 spliced mRNAs of HPV16 to the amount of U1A mRNAs, the ratio of the amount of 226ˆ526 spliced mRNAs of HPV16 to the amount of 880ˆ3358 spliced mRNA of HPV16, the ratio of the amount of 226ˆ526 spliced mRNAs of HPV16 to the amount of 880ˆ2709 spliced mRNA of HPV16, and the ratio of the amount of 226ˆ526 spliced mRNAs of HPV16 to the amount of E5 mRNA of HPV16. It was shown that the calculated ratios showed highly significant differences in progression from mild forms of HPV16 infection to severe forms of infection with HPV16. Moreover, the method of the present invention allows for differentiating between mild and severe forms of HPV infection with an increased specificity and sensitivity than those in the prior art.

In US20070154884, the expression level of E6 and/or E7 and expression level of E2 and/or L1 and a ratio of E6 and/or E7 to L1 and/or E2 were determined, wherein a ratio of greater than 2 is indicative of HPV-induced cell transformation and risk of neoplasia.

According to the data presented in the method of the present invention, determining the expression level of 226ˆ526 spliced transcripts rather than determination of the amount of E6 or E7 full-length ORF containing transcripts in comparison to a second gene product, e.g. Ubc transcripts, is more indicative of the stage of HPV-based disease (Table 6, as indicated by the p-value). Surprisingly, it was found that the expression of the 226ˆ526 (E6*II) spliced transcript is stronger upregulated during cancer progression, than E6*I and E6 or E7 full-length ORF containing transcripts (FIG. 4). Consequently, the determination of the gene expression of 226ˆ526 spliced transcript is more advantageous for differentiating between mild and severe forms of HPV16 infection. Preferably, determination of E6*II expression is compared to a second gene product as aforementioned. Moreover, the present invention describes the suitability of E6*II in combination with a second gene product such as 880ˆ3358, 880ˆ2709 or E5 full-length ORF containing transcripts for analysis of the integration status of HPV (FIG. 6). In particular, these combinations were more reliable in detecting the integration status than other combinations known in the art.

Moreover, the present invention relates to a method for differentiating in a subject with HPV16 between (i) a severe form of HPV16 infection and (ii) a mild form of HPV16 infection, comprising the steps a) calculating a first ratio, said calculation comprising the steps of
  a1) determining the amount of a first gene product in a sample of said subject, said first gene product being a gene product of 880ˆ2582,
  a2) determining the amount of a second gene product in a sample of said subject, said second gene product being selected from the group consisting of a gene product of 3632ˆ5639, a gene product of 880ˆ3358, a gene product of Apm1, a gene, product of Ubc, a gene product of U1A, a gene product of E1, a gene product of E5, a gene product of L1 and a gene product of E6*I, and
  a3) calculating a first ratio of the amount of said first gene product as determined in step a1) and the amount of said second gene product as determined in step a2),
b) calculating a second ratio, said calculation comprising the steps of
  b1) determining the amount of a third gene product in a sample of said subject, said first gene product being a gene product of E6*II,
  b2) determining the amount of a fourth gene product in a sample of said subject, said fourth gene product being selected from the group consisting of a gene product of Apm1, a gene product of Ubc, a gene product of U1A, a gene product of 880ˆ9358, a gene product of 880ˆ2709, and a gene product of E5, and
  b3) calculating a second ratio of the amount of said third gene product as determined in step b1) and the amount of said fourth gene product as determined in step b2), and
c) comparing said first ratio as determined in step a) with a first reference ratio, and comparing said second ratio as determined in step b) with a second reference ratio, and
d) differentiating between (i) a severe form of HPV16 infection and (ii) a mild form of HPV16 infection.

Preferably, said second gene product is a gene product of 3632ˆ5639, preferably said fourth gene product is a gene product of 880ˆ3358.

Preferred reference ratios of the various gene products in the context of the present invention are set forth elsewhere herein (Table 5).

Preferably, the ratio of the amount of the first gene product to the second gene product as well as the ratio of the amount of the third gene product to the fourth gene product are calculated.

Preferably, (i) a first ratio larger that said first reference ratio and/or (ii) and a second ratio larger than the second reference ratio is indicative for a severe form of HPV16 infection. Thus, a severe form of HPV16 is, preferably, indicated if either said first or said second ratio or both is/are larger than the corresponding reference ratio.

Preferably, (i) a first ratio lower that said first reference ratio and (ii) and a second ratio lower than the second reference ratio are indicative for a mild form of HPV16 infection. Thus, a mild form of HPV16 infection is, preferably, indicated if both said first ratio and said second ratio are lower than the corresponding reference ratio.

It was found in the context of the present invention that calculating a first ratio (as in step a) of the aforementioned method) and a second ratio (as in step b) of the aforementioned method, and comparing said first and said second ratio with a reference ratio allows reliably differentiating between severe and mild forms of HPV16 infection. Particularly, it has been found that calculating said first ratio and comparing said first ratio with a reference ratio allows identifying subjects which comprise the HPV16 genome in an episomal form (see below), but which suffer from a severe form of HPV infection (or are at risk thereof). Generally, subjects comprising the HPV16 genome in an episomal form only are considered to be at a lower risk for suffering from HSIL or cancer than subjects with the HPV16 genome in an integrated form (for an explanation of the terms "episomal form" and "integrated forms" see herein below). However, there is evidence that some subjects comprising the HPV16 genome only in an episomal form suffer from severe forms of HPV16 infection or are at elevated risk of suffering thereof (Vinokurova, S., N. Wentzensen, I. Kraus, R. Klaes, C. Driesch, P. Melsheimer, F. Kisseljov, M. Durst, A. Schneider, and M. von Knebel Doeberitz. 2008. Type-dependent integration frequency of human papillomavirus genomes in cervical lesions. Cancer Res 68:307-13, Pett, M., and N. Coleman. 2007. Integration of high-risk human papillomavirus: a key event in cervical carcinogenesis? J Pathol 212:356-67). By calculating a first ratio as said forth above, those subjects which have the HPV16 genome in an episomal form and which suffer from severe forms of HPV16 infection (or are at risk thereof) can be reliably identified. Preferably, subjects with a first ratio larger than the corresponding first reference ratio comprise the HPV16 genome in an episomal form, but suffer from severe forms of HPV16 infection (or are at risk thereof). Preferably, a first ratio lower than the reference ratio indicates that said suffers does not suffer from a severe form of HPV16 infection (if also the second ratio is lower than the corresponding reference ratio and, thus, if said subject does not comprise the HPV16 genome in an integrated form, see below).

Moreover, it was found that calculating a second ratio and comparing said second ratio with a second reference ratio allows reliably identifying those subjects which comprise the HPV16 genome in an integrated form. Particularly, a second ratio larger than the second reference ratio indicates that the subject comprises the HPV16 genome in an integrated form, whereas a second ratio lower that the second reference ratio indicates that said subject does not comprise the HPV16 genome in an integrated form.

Thus, a first ratio and/or a second reference ratio larger than the corresponding reference ratio, preferably, indicates that the subject suffers from a severe form of HPV16 infection (or is at risk thereof), whereas, a first ratio and a second reference ratio lower than the corresponding reference ratio, preferably, indicates that the subject suffers from a mild form of HPV16 infection. Thus, the calculation of a first ratio and a second ratio significantly increases the specificity and the sensitivity of the diagnosis.

Moreover, it was shown in the context of the present invention, that the determination of a gene product of 880^2582 alone allows identifying those subjects which comprise the HPV16 in an episomal form and which suffer from severe forms of HPV16 infection (or are at risk of suffering thereof). This clinically useful assessment of HPV-associated disease is based only on a simple positive/negative determination of expression of HPV 880^2582 containing RNA transcripts, with no requirement for accurate quantitative measurements of expression levels or for determination of differences in the levels of expression of the two transcripts (see below).

Thus, the present invention relates to a method for differentiating in a subject with HPV16 between (i) a severe form of HPV16 infection and (ii) a mild form of HPV16 infection, comprising the steps a1) determining, in a sample of said subject, the amount of a gene product of 880^2582, a2) comparing the amount as determined in step a1) with a reference, b) assessing, in a sample of said subject, the integration status of the HPV16 genome, and c) differentiating between (i) a severe form of HPV16 infection and (ii) a mild form of HPV16 infection.

Preferably, steps a1) and a2) of the aforementioned method allow identifying a subject comprising the genome of HPV16 in an episomal form, but suffering from a severe form of HPV16 infection (or being at risk thereof). Preferably, the assessment in step b) of the aforementioned method allows identifying subjects comprising the HPV16 genome in an integrated form or not. Subjects comprising the HPV16 genome in an integrated form, preferably, suffer from severe forms of HPV16 infection (or are at elevated risk thereof) (Vinokurova, S., N. Wentzensen, I. Kraus, R. Klaes, C. Driesch, P. Melsheimer, F. Kisseljov, M. Durst, A. Schneider, and M. von Knebel Doeberitz. 2008. Type-dependent integration frequency of human papillomavirus genomes in cervical lesions. Cancer Res 68:307-13, Pett, M., and N. Coleman. 2007. Integration of high-risk human papillomavirus: a key event in cervical carcinogenesis? J Pathol 212:356-67). Subjects not comprising the HPV16 genome in an integrated form, preferably, are not suffering from severe forms of HPV16 infection (and are not at elevated risk thereof), if also the amount of a gene product of 880^2582 is lower than the reference.

The aforementioned method comprises the step of assessing, in a sample of the subject, integration status of the HPV16 genome. It is known in the art that the HPV16 genome can be present in a host cell in an integrated form, in an episomal form, or both. The terms "integrated" and "episomal" are understood by the skilled person. The HPV16 genome is, preferably, present in an integrated form in a host cell, if said HPV16 genome is stably comprised by chromosomal DNA of the host cell. The HPV16 genome is, preferably, present in an episomal form in a host cell, if said genome replicates in said host cell without being integrated into the chromosomal DNA of the host cell (Vinokurova, S., N. Wentzensen, I. Kraus, R. Klaes, C. Driesch, P. Melsheimer, F. Kisseljov, M. Durst, A. Schneider, and M. von Knebel Doeberitz. 2008. Type-dependent integration frequency of human papillomavirus genomes in cervical lesions. Cancer Res 68:307-13).

The phrase "assessing the integration status of the HPV16 genome", as used herein, preferably, means assessing whether the genome of HPV16 is present in an integrated form or not, and thus, whether said genome is integrated into the chromosomal DNA of a host cell or not. It is to be understood that, if the HPV16 genome is integrated into the genome of a subject, not the entire cells of said subject will have the HPV16 genome integrated into its genome. Preferably, only cells that are affected by HPV16 infection may comprise the HPV16 genome in an integrated form. Preferably, said cells are present in the urogenital or oropharyngeal tract of said subject. It is to be understood that the term "integrated form" also encompasses the integration of parts of the HPV16 into chromosomal DNA of the host cell. Preferably, the early region of the HPV16 genome, including genes for E6, E7 and parts of the E1 N-terminus, is integrated into the host genome. It is to be understood that also the late region, including the E4, E5 and L1 genes, of the HPV16 genome might be integrated into the host genome, however, most preferably, are transcriptionally inactive due to genomic rearrangements. Moreover, it is known that the E2 gene is usually lost during integration or transcriptionally inactivated (Pett, M., and N. Coleman. 2007. Integration of high-risk human papillomavirus: a key event in cervical carcinogenesis? J Pathol 212:356-67).

How to assess the integration status of the HPV16 genome is well known in the art. Preferably, the integration status is determined in a sample of the subject. Preferred methods for determining the integration status are (i) methods that detect virus-host fusion transcripts, particularly transcriptionally active viral integrants, e.g. by amplification of papillomavirus oncogene transcripts (APOT-assay) and RNA in situ hybridisation (ISH); and (ii) methods that detect integrated viral DNA regardless of its transcriptional status, e.g. Southern blotting, quantitative real-time PCR, restriction-site PCR, and DNA ISH (Pett, M., and N. Coleman. 2007. Integration of high-risk human papillomavirus: a key event in cervical carcinogenesis? J Pathol 212:356-67).

Accordingly, the term "reference amount" as used herein refers to an amount which allows for differentiating between a mild and severe form of HPV infection in a subject with HPV16. Accordingly, the reference may either be derived from (i) a subject known to suffer from a mild form of HPV infection (ii) known to suffer from a severe form of HPV infection. For (i) and (ii), the reference is, preferably, derived from a subject who comprises the HPV only in an episomal form. Moreover, the reference amount for a gene product of 880^2582 may define a threshold amount, whereby an amount of a gene product of 880^2582 lower than the respective threshold shall be indicative for a subject suffering from a mild form of HPV infection (if said subject does not comprise the HPV16 genome in an integrated from, see elsewhere), while an amount of a gene product of 880^2582 larger than the threshold amount shall be an indicator for a subject suffering from a severe form of HPV16 infection. The reference amount applicable for an individual subject may vary depending on various physiological parameters such as age, gender, or subpopulation, as well as on the means used for the determination of the transcript or polypeptide referred to herein. A suitable reference amount may be determined by the method of the present invention from a reference sample to be analyzed together, i.e. simultaneously or subsequently, with the test sample.

Preferably, an amount of a gene product of 880^2582 larger than the reference amount and/or the presence of the HPV16 genome in an integrated form indicates a severe form of HPV16 infection.

Preferably, an amount of a gene product of 880^2582 lower than the reference amount and the absence of an integrated form of the HPV16 genome (thus, the HPV16 genome is not integrated into the chromosomal DNA) indicates a mild form of HPV16 infection.

In the context of the present invention it was shown that the presence of gene products of 880^2582 indicates a severe form of HPV16 infection, wherein the absence of gene products of 880^2582, together with the absence of integrated forms of the HPV16 genome, indicates a mild form of HPV16 infection (see also next paragraph). Thus, the reference amount, preferably, is the detection limit. Accordingly, an amount of a gene product of 880^2582 larger than the detection limit and/or the presence of the HPV16 genome in an integrated form, preferably, indicates a severe form of HPV16 infection. Preferably, an amount of a gene product of 880^2582 lower than the detection limit and the absence of an integrated form of the HPV16 genome (thus, the HPV16 genome is not integrated into the chromosomal DNA) indicates a mild form of HPV16 infection. The person skilled in the art knows how to determine a detection limit. The term "detection limit" as used herein, preferably, refers to the detection limit of the assay for the determination 880^2582 as described in the Examples.

Advantageously, it was shown that determining the amount of a gene product of 880^2582, comparing said amount with a reference amount, and assessing the integration status of the HPV16 genome, is required in order to reliably differentiate between a mild and a more severe form of HPV16 infection in a subject being infected with HPV16. Specifically, the amount of the 880^2582 spliced mRNAs was determined in samples comprising cervical exfoliated cells of patients with cytologically defined lesions (LSIL to HSIL, cervical cancer). Additionally, 880^2582 spliced mRNA was found in various cervical cancer cell lines, including SiHa, CasK1, MRI-H196, and MRI-H186. Moreover, the integration status was assessed by determining the amount of the transcripts that are usually absent in cells with integrated HPV genome (e.g. absence of 880^3358 indicates that the HPV genome is chromosomally integrated and that E1^E4 expression is absent). It was shown that the detection of E6*II encoding transcripts relative to the detection of E1^E4 encoding 880^3358 transcripts, E2 encoding 880^2709 transcripts or E5 encoding E5 full-length transcripts is indicative for the integration status. Thus, by determining the ratio of E6*II encoding transcripts with e.g. E1^E4, E2 or E5 encoding transcripts the integration status could be predicted more precisely than by using known transcript combinations such as E6 and/or E7 compared to E2 and/or E5 and/or L1 (FIG. 6, Table 5).

The method of the present invention, if applied, is beneficial since the method allows for assessing the severity of a HPV infection in patients in which the HPV genome is not integrated into the chromosomal DNA of cells affected by HPV. In the prior art, integration of the HPV genome into the chromosomal DNA of the host, is known to be associated with a worse prognosis and is thought to play a key role in the development of cervical cancer. However, there are several reports that cervical cancer can also develop if the HPV genome is not integrated into the chromosomal DNA of the host. Reliable HPV marker-based methods for differentiating between mild forms and severe forms of HPV16 infection in subjects that do not comprise the HPV genome in an integrated form are not described in the art.

In a preferred embodiment of the method of the present invention, the assessment of the integration status comprises the steps b1) determining, in a sample of the subject, the amounts of a first gene product of E6*II and a second gene product being selected from the group consisting of a gene product of 880^1358, a gene product of 880^2709, and a gene product of E5, b2) calculating a ratio of the amount of a the first gene product and the amount of second gene product (preferably, the ratio of the amount of the first gene product to the amount of the second gene product), and b3) comparing said ratio to a reference ratio.

Preferred methods for the determination of the amounts of a gene product and for the calculation of reference ratios, as well as preferred reference ratios are described elsewhere herein (Table 5).

Preferably, the ratio to be determined for assessing the integration status is the ratio of the amount of a gene product of E6*II to the amount of a gene product of 880^3358.

Preferably, a ratio of the amount of a first gene product of E6*II to the amount of a second gene product, preferably, of 880^1358 larger than the reference ratio, indicates that the genome of HPV is present in an integrated form.

Preferably, a ratio of the amount of a first gene product of E6*II to the amount of a second gene product, preferably of 880^3358, lower than the reference ratio, indicates that the genome of HPV is not present in an integrated form.

Accordingly, (i) an amount of a gene product of 880^2582 larger than the reference amount and/or (ii) a ratio of the amount of a gene product of E6*II to the amount of a gene product of 880^3358 larger than the reference ratio indicates a severe form of HPV16 infection.

Preferably, (i) an amount of a gene product of 880^2582 lower than the reference amount and (ii) a ratio of the amount of a gene product of E6*II to the amount of a gene product of 880^9358 lower than the reference ratio (indicating the absence of an integrated form of the HPV16 genome) indicates a mild form of HPV16 infection.

Advantageously, it was show in the studies of the present invention that the integration status of the HPV16 genome can be assessed by b1) determining, in a sample of the subject, the amounts of a gene product of E6*II and a second gene product (preferably 880^3358), b2) calculating a ratio of the amount of a gene product of E6*II and the amount of a second gene product (preferably, the ratio of the amount of a gene product of E6*II to the amount of a second gene product), and b3) comparing said ratio to a reference ratio. The assessment of the integration status by carrying out the aforementioned steps is advantageous since the determination of the amount of a gene product of 880^2582 (see step a1) and the assessment of the integration status can be done simultaneously by quantifying the gene products of 880^2582, 3632^5639, E6*II and 880^3358 in a single reaction.

In an even more preferred embodiment of the aforementioned method of the present invention, step a1) further comprises determining the amount of a further gene product, said further gene product being selected from the group consisting of a gene product 3632^5639, a gene product of 880^3358, a gene product of Apm1, a gene product of Ubc, a gene product of U1A, a gene product of E1, a gene product of E5, a gene product of L1 and a gene product of E6*I and calculating a ratio of the amount of a gene product of 880^2582 and the amount of said further gene product. In step a2) the, thus, determined ratio is compared with a reference ratio (instead comparing the amount of 880^2582 with a reference amount). Preferred reference ratios are described elsewhere herein.

Preferably, said further gene product is a gene product of 3632^5639.

Preferably, the calculated ratio of the amount of a gene product of 880^2582 and the amount of said further gene product is the ratio of the amount of a gene product of 880^2582 to the amount of said further gene product.

Preferably, a ratio of the amount of said gene product of 880^2582 to the amount of said further gene product larger than the reference ratio and/or the presence of the HPV16 genome in an integrated form indicates a severe form of HPV16 infection.

More preferably, a ratio of the amount of said gene product of 880^2582 to the amount of said further gene product larger than the reference ratio and/or the presence of the HPV16 genome in an integrated form indicates a severe form of HPV16 infection.

Most preferably, a (i) ratio of the amount of said gene product of 880^2582 to the amount of said further gene product larger than the reference ratio and/or (ii) a ratio of the amount of a gene product of E6*II to the amount of a gene product of 880^3358 lower than the reference ratio (indicating the absence of an integrated form of the HPV16 genome) indicates a mild form of HPV16 infection.

Preferably, a ratio of the amount of a gene product of 880^2582 to the amount of said further gene product lower than the reference ratio and the absence of an integrated form of the HPV16 genome (thus, the HPV16 genome is not integrated into the chromosomal DNA) indicates a mild form of HPV16 infection.

More preferably, a ratio of the amount of a gene product of 880^2582 to the amount of said further gene product lower than the reference ratio and a ratio of the amount of a gene product of E6*II to the amount of a gene product of 880^3358 lower than the reference ratio (indicating the absence of an integrated form of the HPV16 genome) indicates a mild form of HPV16 infection.

It is also contemplated to carry out the method of the present invention for other HPV genotypes (instead of HPV16, and thus for subjects infected with other HPV genotypes), particularly for HPV18, HPV31, HPV33, HPV35, HPV45. It is to be understood that amount of those gene products are determined that correspond to the gene products of HPV16 as described herein.

High-risk HPV types, apart from HPV16 are well known contributing to ~45% of all cervical cancers. It has been demonstrated that integration plays an important role in the carcinogenesis of all high-risk HPV types. However, for high-risk HPV types 16 and phylogenetically related types 31 and 33, integration occurs less frequently, suggesting a second mode of progression such as the E1C-mediated upregulation of the LCR. But still for a large proportion cervical cancer caused by these HPV types and for a very high proportion of cervical cancers caused by other types, including HPV18, and 45, integration is the key event in the development of cervical cancer (Vinokurova, S., N. Wentzensen, I. Kraus, R. Klaes, C. Driesch, P. Melsheimer, F. Kisseljov, M. Durst, A. Schneider, and M. von Knebel Doeberitz. 2008. Type-dependent integration frequency of human papillomavirus genomes in cervical lesions. Cancer Res 68:307-13). The measurement of integration by transcript analyses as described herein, thus, allows easily identifying those women with integrated HPV genomes. In a preferred embodiment, integration is measured by quantifying the gene product of E6*I of HPV types 18, 31, 33, 35, and 45, and comparing it to a second gene product of E1^E4. The respective splice donor sites of E6*I encoding transcripts are located at nt 233, 210, 231, 232, and 230 for HPV types 18, 31, 33, 35, 45, respectively, and the splice acceptor sites are located at nt 416, 413, 509, 415, and 413 for PV types 18, 31, 33, 35 and 45, respectively. The respective splice donor sites of E1^E4 encoding transcripts are located at nt 929, 877, 894, and 929 for HPV types 18, 31, 33, and 45, respectively, and the splice acceptor sites are located at nt 3432, 3295, 3351, and 3421 for HPV types 18, 31, 33 and 45, respectively. Persons skilled in the art know how to determine the splice junction of the E1^E4 encoding transcript of HPV35 e.g. by amplifying cDNA by PCR and subsequent sequencing.

The sequence of the genomes of the various HPV genotypes referred to above have the following GenBank Accession-Numbers:

| HPV31 | J04353.1    | GI: 333048  |
| HPV33 | M12732.1    | GI: 333049  |
| HPV35 | M74117.1    | GI: 333050  |
| HPV18 | NC_001357.1 | GI: 9626069 |
| HPV45 | X74479.1    | GI: 397022  |

Moreover, the present invention relates to a method for differentiating in a subject with HPV16, between (i) a severe form of HPV16 infection and (ii) a mild form of HPV16 infection, comprising the steps
  a) determining, in a sample of said subject, the amount of a gene product of 880^2582,
  b) comparing the amount as determined in step a1) with a reference amount,
  c) differentiating between (i) a severe form of HPV16 infection and (ii) a mild form of HPV16 infection,
wherein the subject does not comprise the HPV16 genome in an integrated form.

Preferably, an amount of a gene product of 880^2582 larger than the reference amount indicates a severe form of HPV16 infection in said subject.

Preferably, an amount of a gene product of 880^2582 lower than the reference amount indicates a mild form of HPV16 infection in said subject.

In a preferred embodiment step a) further comprises determining the amount of a further gene product, said further gene product being selected from the group consisting of a gene product of 3632^5639, a gene product of 880^3358, a gene product of Apm1, a gene product of Ubc, a gene product of U1A, a gene product of E1, a gene product of E5, a gene product of L1 and a gene product of E6*I (see also above) and calculating a ratio of the amount of a gene product of 880^2582 and the amount of the further gene product, preferably of 3632^5639. In step b) the, thus, determined ratio is compared with a reference ratio (instead comparing the amount of the gene product of 880^2582 with a reference amount).

Preferably, the calculated ratio of the amount of a gene product of 880^2582 and the amount of a further gene product is the ratio of the amount of a gene product of 880^2582 to the amount of a further gene product.

Preferably, a ratio of the amount of a gene product of 880^2582 to the amount of a further gene product larger than the reference ratio indicates a severe form of HPV16 infection in said subject.

Preferably, a ratio of the amount of a gene product of 880^2582 to the amount of a further gene product lower than the reference ratio indicates a mild form of HPV16 infection in said subject.

Preferred reference ratios are described elsewhere herein.

Besides HPV16, other high-risk HPV types are known to cause cervcial cancer (Munoz, N., F. X. Bosch, S. de Sanjose, R. Herrero, X. Castellsague, K. V. Shah, P. J. Snijders, and C. J. Meijer. 2003. Epidemiologic classification of human papillomavirus types associated with cervical cancer. N. Engl. J. Med. 348:518-527). Among those, strongest evidence of their oncogenic potential is known for HPV types 18, 31, 33, 35, and 45. As for HPV16, integration is not found in all cases of cervical carcinomas caused by these types (Vinokurova, S., N. Wentzensen, I. Kraus, R. Klaes, C. Driesch, P. Melsheimer, F. Kisseljov, M. Durst, A. Schneider, and M. von Knebel Doeberitz. 2008. Type-dependent integration frequency of human papillomavirus genomes in cervical lesions. Cancer Res 68:307-13), indicating that HPV16-like 880^2582 transcripts or the respective HPV16-like E1C (C-terminal part of the viral E1 protein) polypeptide exist in these HPV types as well. Persons skilled in the art know how to determine the splice junction of the other high-risk HPV types, e.g. by amplifying cDNA by PCR and subsequent sequencing. Accordingly, determining the amounts of the respective E1C transcripts, and, optionally, assessing the integration status, allows for differentiating between mild and severe forms of hrHPV infection with the respective hrHPV genotype, particularly HPV 18, 31, 33, 35 and 45.

Also, the present invention relates to a method for differentiating in a subject with HPV16 between (i) a severe form of HPV16 infection and (ii) a mild form of HPV16 infection, comprising the steps
  a) determining the amount of a first gene product in a sample of said subject, said first gene product being a gene product of p16$^{INK4A}$,
  b) determining the amount of a second gene product in a sample of said subject, said second gene product being a gene product of 880^3358,
  c) calculating a ratio of the amount of said first gene product as determined in step a) and the amount of said second gene product as determined in step b),
  d) comparing the ratio as calculated in step c) to a reference ratio, and
  e) differentiating between (i) a severe form of HPV16 infection and (ii) a mild form of HPV16 infection.

p16$^{INK4A}$ is a gene that is comprised by the genome of the host cell. Thus, said gene is not encoded by the genome of HPV16. The method of the present invention, thus, contemplates the determination of the amount of the p16$^{INK4A}$ mRNA or the p16$^{INK4A}$ polypeptide.

The term "p16$^{INK4A}$" as meant herein, preferably, refers to cyclin-dependent kinase inhibitor 2A isoform 1. The nucleic acid sequence as well as the amino acid sequence of human p16$^{INK4A}$ are well known in the art and shown e.g. in GenBank Accession No: NM_000077.3 (nucleic acid sequence, SEQ ID NO: 75 and GenBank Accession No: NP_000068.1 (amino acid sequence, SEQ ID NO: 76.

p16$^{INK4A}$ overexpression mediated by E7 is considered a valuable marker for transforming hrHPV infections. Immunostaining for p16$^{INK4A}$ has been found to be associated with intraepithelial or invasive neoplasia in cervical cytology and histology specimens (Dallenbach-Hellweg, G., M. J. Trunk, and M. von Knebel Doeberitz. 2004. Traditional and new molecular methods for early detection of cervical cancer. Arkh Patol 66:35-9).

Once a severe form of HPV16 infection is diagnosed in a subject by carrying out any of the aforementioned methods, a cancer therapy or an additional cancer examination can be initiated.

Accordingly, the present invention relates to a method for identifying a subject with HPV16 being susceptible to a cancer therapy and/or being susceptible to a cancer examination, comprising the steps,
- a) determining the amount of a first gene product in a sample of said subject, said first gene product being a gene product of 880^2582,
- b) determining the amount of a second gene product in a sample of said subject, said second gene product being selected from the group consisting of a gene product of 3632^5639, a gene product of 880^3358, a gene product of Apm1, a gene product of Ubc, a gene product of U1A, a gene product of E1, a gene product of E5, a gene product of L1 and a gene product of E6*I,
- c) calculating a ratio of the amount of said first gene product as determined in step a) and the amount of said second gene product as determined in step b),
- d) comparing the ratio as calculated in step c) to a reference ratio, and
- e) identifying a subject being susceptible to cancer therapy and/or being susceptible to a cancer examination.

Moreover, the present invention relates to a method for identifying a subject with HPV16 being susceptible to a cancer therapy and/or being susceptible to a cancer examination, comprising the steps,
- a) determining the amount of a first gene product in a sample of said subject, said first gene product being a gene product of E6*II,
- b) determining the amount of a second gene product in a sample of said subject, said second gene product being selected from the group consisting of a gene product of Apm1, a gene product of Ubc, a gene product of U1A, a gene product of 880^3358, a gene product of 880^2709, and a gene product of E5,
- c) calculating a ratio of the amount of said first gene product as determined in step a) and the amount of said second gene product as determined in step b),
- d) comparing the ratio as calculated in step c) with a reference ratio, and
- e) identifying a subject being susceptible to cancer therapy.

Moreover, the present invention relates to a method for identifying a subject with HPV16 being susceptible to a cancer therapy and/or being susceptible to a cancer examination, comprising the steps,
- a1) determining, in a sample of said subject, the amount of a gene product of 880^2582,
- a2) comparing the amount as determined in step a1) with a reference amount,
- b) assessing, in a sample of said subject, the integration status of the HPV16 genome and
- c) identifying a subject being susceptible to cancer therapy and/or being susceptible to a cancer examination.

Moreover, the present invention relates to a method for identifying a subject with HPV16 being susceptible to a cancer therapy and/or being susceptible to a cancer examination, comprising the steps,
- a) determining, in a sample of said subject, the amount of a gene product of 880^2582,
- b) comparing the amount as determined in step a1) with a reference amount,
- c) identifying a subject being susceptible to cancer therapy and/or being susceptible to a cancer examination, wherein the subject does not comprise the HPV16 genome in an integrated form.

Moreover, the present invention relates to a method for identifying a subject with HPV16 being susceptible to a cancer therapy and/or being susceptible to a cancer examination,
- a) calculating a first ratio, said calculating of said first ratio comprising the steps of
  - a1) determining the amount of a first gene product in a sample of said subject, said first gene product being a gene product of 880^2582,
  - a2) determining the amount of a second gene product in a sample of said subject, said second gene product being selected from the group consisting of a gene product of 3632^5639, a gene product of 880%3358, a gene product of Apm1, a gene product of Ubc, a gene product of U1A, a gene product of E1, a gene product of E5, a gene product of L1 and a gene product of E6*I, and
  - a3) calculating a first ratio of the amount of said first gene product as determined in step a1) and the amount of said second gene product as determined in step a2),
- b) calculating a second ratio, said calculation comprising the steps of
  - b1) determining the amount of a third gene product in a sample of said subject, said first gene product being a gene product of E6*II,
  - b2) determining the amount of a fourth gene product in a sample of said subject, said fourth gene product being selected from the group consisting of a gene product of Apm1, a gene product of Ubc, a gene product of U1A, a gene product of 880^3358, a gene product of 880^2709, and a gene product of E5, and
  - b3) calculating a second ratio of the amount of said third gene product as determined in step b1) and the amount of said fourth gene product as determined in step b2), and
- c) comparing said first ratio as determined in step a) with a first reference ratio, and comparing said second ratio as determined in step b) with a second reference ratio, and
- d) identifying a subject being susceptible to cancer therapy and/or being susceptible to a cancer examination.

The term "identifying" as used herein means assessing whether a subject will be susceptible for cancer therapy or not, or assessing whether a subject is susceptible to a cancer examination or not. As will be understood by those skilled in the art, such an assessment is usually not intended to be correct for all (i.e. 100%) of the subjects to be identified. The term, however, requires that a statistically significant portion of subjects can be identified (e.g. in a cohort study). Whether a portion is statistically significant can be determined without further ado by the person skilled in the art using various well known statistic evaluation tools, e.g., determination of confidence intervals, p-value determination, Student's t-test, Mann-Whitney test etc. Details are found in Dowdy and Wearden, Statistics for Research, John Wiley & Sons, New York 1983. Preferred confidence intervals are at least 90%, at least 95%, at least 97%, at least 98% or at least 99%. The p-values are, preferably, 0.1, 0.05, 0.01, 0.005, or 0.001. More preferably, at least 60%, at least 70%, at least 80% or at least 90% of the subjects of a population can be properly identified by the method of the present invention.

Suitable cancer therapies are well known in the art. Preferably, the term "cancer therapy" includes any therapy that aims to treat the severe forms of HPV16 infection, preferably HSIL, CIN2/3 and cervical cancer. Preferably, said cancer therapy is selected from conisation, loop electrosurgical excision procedure (LEEP), surgery including trachelectomy and hysterectomy and chemotherapy and radiochemotherapy. Preferably, the term "cancer examination" is selected from colposcopy examination and colposcopy-directed biopsy with subsequent histochemical analysis.

Moreover, the present invention relates to a composition comprising a probe oligonucleotide mixture, wherein said probe oligonucleotide mixture comprises a probe oligonucleotide that specifically detects the first transcript as defined herein, and a probe oligonucleotide that specifically detects the second transcript as defined herein. Preferably, said composition comprises two probe oligonucleotides. Preferred nucleic acid sequences of preferred probe oligonucleotides are described elsewhere herein (Table 1).

Moreover, the present invention relates to a composition comprising an oligonucleotide mixture, said oligonucleotide mixture comprising oligonucleotides that specifically amplify the first gene product, preferably a transcript, of the method of the present invention, and oligonucleotides that specifically amplify at least one second gene product of the method of the present invention, preferably a transcript (Table 3).

Moreover, the present invention relates to a composition comprising a first composition comprising a probe oligonucleotide mixture, and a second composition comprising an oligonucleotide mixture, said oligonucleotide mixture comprising oligonucleotides that specifically amplify the first gene product, preferably a transcript, of the method of the present invention, and oligonucleotides that specifically amplify at least one second gene product of the method of the present invention, preferably a transcript (Table 1, 3).

Moreover, the present invention relates to a composition comprising (i) an antibody that specifically binds to a peptide comprised by the first polypeptide (preferably, an antibody that binds to the region of the first polypeptide that is encoded by the nucleic acids flanking the splice junction referred to herein), (ii) an antibody that specifically binds to a peptide comprised by the second polypeptide (preferably, an antibody that bind to the region of the first polypeptide that is encoded by the nucleic acids flanking the splice junction referred to herein)

Moreover, the present invention relates to a device for differentiating in a subject with HPV16 between (i) a severe form of HPV16 infection and (ii) a mild form of HPV16 infection or for identifying a subject being susceptible to cancer therapy and/or being susceptible to a cancer examination,
  a) a composition comprising an oligonucleotide mixture, said oligonucleotide mixture comprising oligonucleotides that specifically amplify the first gene product, preferably a transcript, of the method of the present invention, and oligonucleotides that specifically amplify at least one second gene product of the method of the present invention, preferably a transcript,
  b) a composition comprising a probe oligonucleotide mixture, or
  c) a composition comprising a probe oligonucleotide mixture, and a composition comprising an oligonucleotide mixture, said oligonucleotide mixture comprising oligonucleotides that specifically amplify the first gene product, preferably a transcript, of the method of the present invention, and oligonucleotides that specifically amplify at least one second gene product of the method of the present invention, preferably a transcript.

Moreover, the present invention relates to a device for differentiating in a subject with HPV16 between (i) a severe form of HPV16 infection and (ii) a mild form of HPV16 infection or for identifying a subject being susceptible to cancer therapy and/or being susceptible to a cancer examination, comprising means for determining the amount of a first gene product in a sample of subject, means for determining the amount of a second gene product in a sample of a subject, means for calculating the ratio of the amount of said first gene product and the amount of the second gene product, and means for comparing the calculated ratio with a reference ratio, whereby it is differentiated between (i) a severe form of HPV16 infection and (ii) a mild form of HPV16 infection, or whereby a subject being susceptible to cancer therapy and/or being susceptible to a cancer examination is identified.

Moreover, the present invention relates to a device for differentiating in a subject with HPV16 between (i) a severe form of HPV16 infection and (ii) a mild form of HPV16 infection or for identifying a subject being susceptible to cancer therapy and/or being susceptible to a cancer examination, comprising means for determining the amount of a gene product of 880^2582 in a sample of subject, means for comparing amount determined by said means with a reference amount, and means for assessing the integration status of the HPV16 genome in a sample of said subject, whereby it is differentiated between (i) a severe form of HPV16 infection and (ii) a mild form of HPV16 infection, or whereby a subject being susceptible to cancer therapy and/or being susceptible to a cancer examination is identified.

Moreover, the present invention relates to a device for differentiating in a subject with HPV16 between (i) a severe form of HPV16 infection and (ii) a mild form of HPV16 infection or for identifying a subject being susceptible to cancer therapy and/or being susceptible to a cancer examination, comprising means for determining the amount of a gene product of 880^2582 in a sample of subject, means for comparing amount determined by said means with a reference amount, and means for assessing the integration status of the HPV16 genome in a sample of said subject, whereby it is differentiated between (i) a severe form of HPV16 infection and (ii) a mild form of HPV16 infection, or whereby a subject being susceptible to cancer therapy and/or being susceptible to a cancer examination is identified.

Moreover, the present invention relates to a device for differentiating in a subject with HPV16 between (i) a severe form of HPV16 infection and (ii) a mild form of HPV16 infection or for identifying a subject being susceptible to cancer therapy and/or being susceptible to a cancer examination, said subject not comprising the HPV16 genome in an integrated form, wherein said device comprises means for determining the amount of a gene product of 880^2582 in a sample of subject, and means for comparing amount determined by said means with a reference amount, whereby it is differentiated between (i) a severe form of HPV16 infection and (ii) a mild form of HPV16 infection, or whereby a subject being susceptible to cancer therapy and/or being susceptible to a cancer examination is identified.

The term "device" as used herein relates to a system of means comprising at least the aforementioned means operatively linked to each other as to allow for differentiating between a mild and a severe form of HPV16 infection of for identifying a subject being susceptible to cancer therapy and/or being susceptible to a cancer examination. Preferred means for determining the amount of a gene product, means for calculating a ratio and means for carrying out the comparison are disclosed above in connection with the method of the invention. How to link the means in an operating manner will depend on the type of means included into the device. For example, where means for automatically determining the amount of the gene products are applied, the data obtained by said automatically operating means can be processed by, e.g., a computer program in order to obtain the desired results. Preferably, the means are comprised by a single device in such a case. Said device may accordingly include an analyzing unit for the measurement of the amount of the gene products in an applied sample and a computer unit for processing the resulting data for the evaluation. Preferred means for detection are disclosed in connection with embodiments relating to the method of the invention above. In such a case, the means are operatively linked in that the user of the system brings together the result of the determination of the amount and the diagnostic or prognostic value thereof due to the instructions and interpretations given in a manual. The means may appear as separate devices in such an embodiment and are, preferably, packaged together as a kit. The person skilled in the art will realize how to link the means without further ado. Preferred devices are those which can be applied without the particular knowledge of a specialized clinician, e.g., test stripes or electronic devices which merely require loading with a sample. The results may be given as output of raw data which need interpretation by the clinician. Preferably, the output of the device is, however, processed, i.e. evaluated, raw data the interpretation of which does not require a clinician. Further preferred devices comprise the analyzing units/devices (e.g., biosensors, arrays, solid supports coupled to ligands specifically recognizing the polypeptide, mRNAs, amplified gene products whose amount shall be determined, Plasmon surface resonance devices, NMR spectrometers, mass-spectrometers, etc.) or evaluation units/devices referred to above in accordance with the method of the invention.

Moreover, the present invention relates to a kit adapted to carry out the method of the present invention, said kit comprising instruction to carry out the said method, and
a) a composition comprising an oligonucleotide mixture, said oligonucleotide mixture comprising oligonucleotides that specifically amplify the first gene product, preferably a transcript, of the method of the present invention, and oligonucleotides that specifically amplify at least one second gene product of the method of the present invention, preferably a transcript,
b) a composition comprising a probe oligonucleotide mixture, or
c) a composition comprising a probe oligonucleotide mixture, and a composition comprising an oligonucleotide mixture, said oligonucleotide mixture comprising oligonucleotides that specifically amplify the first gene product, preferably a transcript, of the method of the present invention, and oligonucleotides that specifically amplify at least one second gene product of the method of the present invention, preferably a transcript.

Moreover, the present invention relates to a kit adapted to carry out the method of the present invention, said kit comprising instruction to carry out the said method, and means for determining the amount of a first gene product in a sample of subject, means for determining the amount of a second gene product in a sample of a subject, means for calculating the ratio of the amount of said first gene product and the amount of the second gene product, and means for comparing the calculated ratio with a reference ratio, whereby it is differentiated between (i) a severe form of HPV16 infection and (ii) a mild form of HPV16 infection, or whereby a subject being susceptible to cancer therapy and/or being susceptible to a cancer examination is identified.

Moreover, the present invention relates to a kit adapted to carry out the method of the present invention, said kit comprising instruction to carry out the said method, and means for determining the amount of a gene product of 880^2582 in a sample of subject, means for comparing amount determined by said means with a reference amount, and means for assessing the integration status of the HPV16 genome in a sample of said subject, whereby it is differentiated between (i) a severe form of HPV16 infection and (ii) a mild form of HPV16 infection, or whereby a subject being susceptible to cancer therapy and/or being susceptible to a cancer examination is identified.

Moreover, the present invention relates to a kit adapted to carry out the method of the present invention, said kit comprising instruction to carry out the said method, and means for determining the amount of a gene product of 880^2582 in a sample of subject, means for comparing amount determined by said means with a reference amount, and means for assessing the integration status of the HPV16 genome in a sample of said subject, whereby it is differentiated between (i) a severe form of HPV16 infection and (ii) a mild form of HPV16 infection, or whereby a subject being susceptible to cancer therapy and/or being susceptible to a cancer examination is identified.

Moreover, the present invention relates to a kit adapted to carry out the method of the present invention, said subject not comprising the HPV16 genome in an integrated form, said kit comprising instructions for carrying out the said method, and means for determining the amount of a gene product of 880^2582 in a sample of subject, and means for comparing amount determined by said means with a reference amount, whereby it is differentiated between (i) a severe form of HPV16 infection and (ii) a mild form of HPV16 infection, or whereby a subject being susceptible to cancer therapy and/or being susceptible to a cancer examination is identified.

The term "kit" as used herein refers to a collection of the aforementioned compounds, means or reagents of the present invention which may or may not be packaged together. The components of the kit may be comprised by separate vials (i.e. as a kit of separate parts) or provided in a single vial. Moreover, it is to be understood that the kit of the present invention is to be used for practising the methods referred to herein above. It is, preferably, envisaged that all components are provided in a ready-to-use manner for practising the methods referred to above. Further, the kit preferably contains instructions for carrying out the said methods. The instructions can be provided by a user's manual in paper- or electronic form. For example, the manual may comprise instructions for interpreting the results obtained when carrying out the aforementioned methods using the kit of the present invention.

All references cited in this specification are herewith incorporated by reference with respect to their entire disclosure content and the disclosure content specifically mentioned in this specification.

BRIEF DESCRIPTION OF THE DRAWING

FIG. 6: Pattern of E6*I versus 880^3358 and E6 fl versus E5 fl expression. Ratios of E6*II versus 880^3358 (left) and E6 fl versus E5 fl (right) are plotted on the y-axis and cytological lesion grades as well as groups of lesions are shown on the x-axis. Dotted lines represent median values.

FIG. 7: Performance of the BIOMERIEUX® HPV kit and the DKFZ NASBA-LUMINEX® Assay compared to cytology as gold standard.

EXAMPLES

The following Examples shall merely illustrate the invention. They shall not be construed, whatsoever, to limit the scope of the invention.

Example 1: Assay Design

Figure 1:
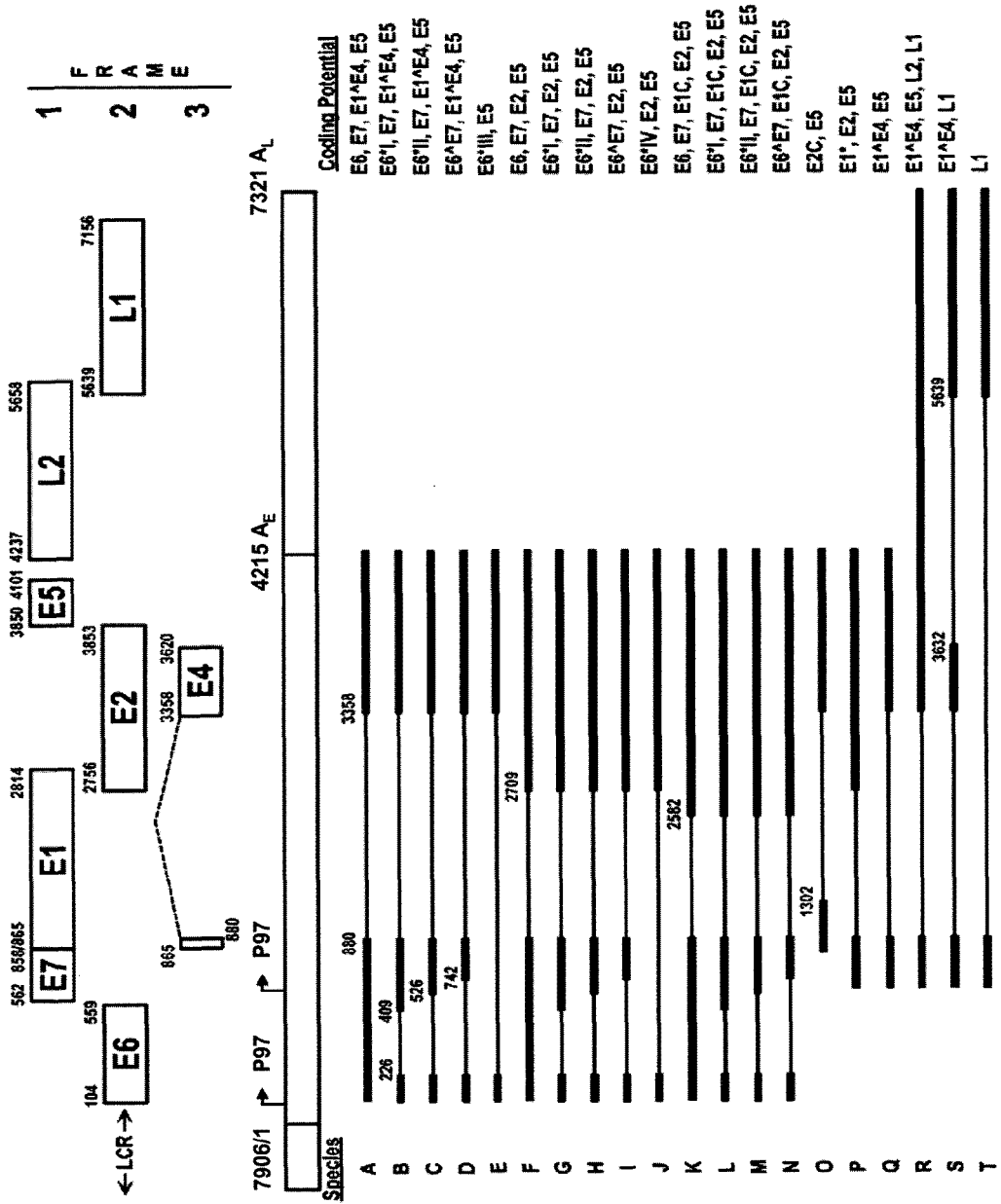
FIG. 1: Genome organisation, open reading frames and transcript species of HPV 16. ORFs are shown in their proper reading frames as rectangles (top of figure). The first number at the upper left end of the rectangles corresponds to the nucleotide (nt) position of the first ATG. The position of the last nt in the stop codon of each ORF is printed at the upper right corner of the rectangles. Located below the genome scale are diagrams of spliced mRNA species. The exons are illustrated by black rectangles, while the introns are indicated by black hairlines between. The numbers printed below the lines indicate the 5' and 3' splice junction positions. The promoter for transcript species O has not been mapped. Transcripts encoding full-length E1 protein are not depicted. Potential, truncated gene products of E6 and E1 are indicated by asterisks (*), the fusion product of the E1 and E4 protein is indicated as E1^E4. Modified from Zheng, Z. M., and C. C. Baker. 2006. Papillomavirus genome structure, expression, and post-transcriptional regulation. Front Biosci 11:2286-302.

In the current study, a novel procedure for the detection and quantification of spliced and unspliced RNA sequences in the uterine cervix was developed. These RNA patterns were characterised with respect to their diagnostic potential in cervical lesions of different grade. As such, novel assays for detection of 10 spliced (226^409 (E6*I), 226^526 (E6*II), 226^1358 (E6*III), 226^2709 (E6*IV), 880^2582, 880^2709, 880^1358, 1302^1358, 1302^5639, 3632^5639) (reviewed in Zheng, Z. M., and C. C. Baker. 2006. Papillomavirus genome structure, expression, and post-transcriptional regulation. Front Biosci 11:2286-302, FIG. 1) and 5 full-length ORF HPV16 RNA sequences (E6, E7, E1, E5, L1) as well as 2 cellular housekeeping (Ubiquitin C, U1A) transcripts were developed.

NASBA uses isothermal target amplification with the simultaneous reaction of three enzymes, avian myeloblastosis virus reverse transcriptase (AMV-RT), RNase H, and T7 RNA polymerase. The steps take place in one reaction tube at a particular temperature (41° C.). A feature of the test is that the first oligonucleotide primer (P1) contains a T7 RNA polymerase promoter sequence. During the reaction, AMV-RT generates a single DNA copy of the target RNA. The RNase H degrades the RNA portion of the DNA/RNA hybrid, and the second primer (P2) anneals to the remaining DNA strand. For later detection using LUMINEX®, the second primer contains a 5' generic sequence. The DNA-dependent DNA polymerase activity of AMV-RT extends P2 and produces a dsDNA copy of the original target RNA with an intact T7 RNA polymerase promoter. This T7 promoter is recognised by the T7 RNA polymerase which initiates transcription of large amounts of anti-sense RNA amplimers.

The NUCLISENS® Basic Kit (Nucleic Acid Sequence-Based Amplification) (BIOMERIEUX® Ltd., France) was used according to the manufacturer's instructions. Briefly, 2.5 µL RNA template was added to 5 µl of reaction mixtures containing 80 mM of KCl, 0.2 µmoles of each primer and 1× of Reagent Sphere without enzymes, and the mixtures were heated to 65° C. for 2 minutes before placing at 41° C. for an additional 2 minutes. Then, 2.5 µL of pooled enzymes were added to each reaction, and amplification reactions were incubated at 41° C. for 90 min.

Anti-sense RNA can be specifically detected by hybridisation to oligonucleotide probes coupled to LUMINEX® beads (Table 1). Upon annealing of a biotin-labelled detector probe to the generic part of P2, which was incorporated into the anti-sense RNA, staining by Strep-PE and measurement in the LUMINEX® analyser takes place. RNA amplicons generated by NASBA were detected using bead-coupled oligonucleotide probes (Table 1). RNA specific probes were coupled as described recently (Schmitt, M., I. G. Bravo, P. J. Snijders, L. Gissmann, M. Pawlita, and T. Waterboer. 2006. Bead-based multiplex genotyping of human papillomaviruses. J Clin Microbiol 44:504-12). All solutions and buffers were certified DNase/RNase free. Of the NASBA reactions, 1 to 0.1 µl were transferred to PCR plates. Using a multi-channel pipette, 49 µl hybridisation solution composed of 33 µl 1.5 M TMAC, 75 mM Tris-HCl, pH 8.0, 6 mM EDTA, pH 8.0, 1.5 g/L sarkosyl, 16 µl TE buffer, 0.2 µmolar 5'-biotinylated decorator probe, and a mixture of 2,000 hybridisation probe-coupled beads per sort were added. The whole mixture was denatured at 95° C. for 5 min and immediately placed on ice for 1 minute. The hybridisation plate was transferred to a heated block shaker and the hybridisation was performed at 41° C. for 30 min. The content of each well was transferred to a wash plate by using a multi-channel pipette. Subsequently, the wells were washed with 100 µlof washing buffer (1×PBS, 0.02% Tween) on a wash station. Beads were resuspended for 20 min on a shaker at RT in 50 µl of detection solution (2 M TMAC, 75 mM Tris-HCl, pH 8.0, 6 mM EDTA, pH 8.0, 1.5 g/L sarkosyl) containing 1/1000 diluted Strep-PE. Beads were washed twice with 100 µl washing buffer and resuspended in 100 µl washing buffer for 2 min on a shaker. Analysis was performed with a LUMINEX® 100 analyser.

To discriminate spliced from full-length RNA sequences, splice site specific LUMINEX® probes rather than specific primers were used. Due to the high degree of homology between splice sites of different HPV types, additional type specific downstream probes were employed.

Table 1. Overview of oligonucleotide hybridisation probes used in the NASBA-LUMINEX® experiments.

TABLE 1

Overview of oligonucleotide hybridisation probes used in the NASBA-Luminex experiments.

| Transcript target | splice site/ full-length probe | SEQ. ID. |
|---|---|---|
| 226^409 | CGACGTGAGGTGTATTAAC | 61 |
| 226^526 | GCGACGTGAGATCATCRAG | 62 |
| 880^2582 | TCCTRCAGATTCYAGGTGGC | 63 |
| 880^2709 | TGATCCTRCAGGACGTGGTC | 77 |
| 880^3358 | TGATCCTRCAGCAGCRACG | 64 |
| 3632^5639 | TACATTTAAAAGATGTCTCTTT | 65 |
| E6 fl$^a$ | AGAYATTATTGTTATAGTKTG | 66 |
| E7 fl | AGAGCCCATTACAATATTGTA | 67 |
| E5 fl | TGTCTRCATACACATCATTA | 68 |
| E1 fl | GTACATTTGAMTTATCACRGA | 69 |
| L1 fl | AAGGCTCTGGGYCTACTGC | 70 |
| p16 | ATAGATGCCGCGGAAGGTC | 71 |
| ubc | TCGCRGTTCTTGTTTGTGGATC | 72 |
| apm1 | TCCACATGCGGAAGCACACA | 73 |
| U1A | AGAAGAGGAAGCCCAAGAGCCA | 74 |

$^a$fl, full-length ORF containing RNA sequence

Example 2: Development of Quantitative NASBA

Quantification and internal performance control in the NASBA assays required addition of in vitro-transcribed calibrator RNA (Q-RNA) of known concentration to the NASBA mix. The only difference between wild-type (wt-) and Q-RNA, the hybridisation probe binding region, allowed the discrimination and quantification of the amplimers using LUMINEX® technology. Wt- and Q-RNA were converted into cDNA and coamplified with the same primers allowing competitive amplification of both RNA. The ratio of the two amplimers at the end of amplification reflected the ratio of the two targets, wt and Q, present at the beginning of amplification. The wt-mRNA present in the unknown sample was quantified using an external standard curve. This standard curve was formed by 10-fold dilution series of in vitro-transcribed RNA in a constant amount of Q-RNA. The in vitro-transcribed wt-RNA was expected to exhibit NASBA-properties similar to wt-mRNA.

Figure 2:
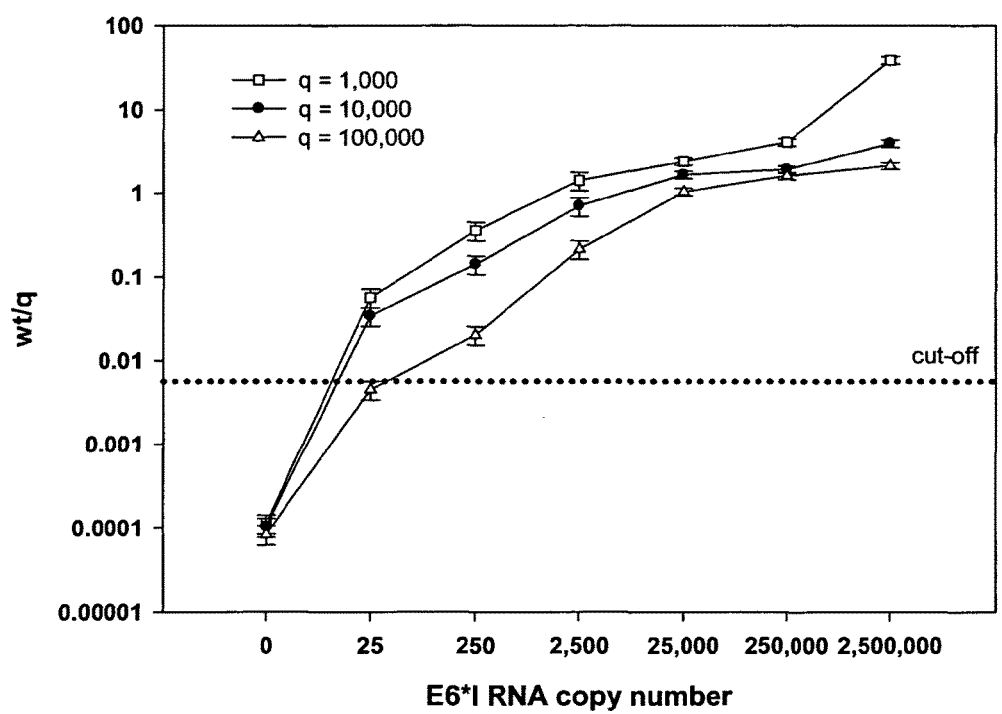
FIG. 2: Dependence of the wt/q-RNA ratio on Q-RNA quantity. Q-RNA, ranging from 1,000 to 100,000 copy numbers per NASBA reaction, was spiked into E6*I wt-RNA dilution series, amplified by NASBA and detected using LUMINEX® hybridisation. The cutoff, displayed as dotted line, was calculated as follows: For each probe, MFI values in reactions with no amplimer added to the hybridisation mixture were considered background values. Net MFI values of hybridised amplimers were computed by subtraction of 1.1 times the median background value from the gross MFI value. Net MFI values above 3 MFI were defined as positive reactions. Standard error of two hybridisation reactions is indicated. Lines between data points are added for better visualisation of the curve slope.

Q-RNA templates were generated by fusion-PCR, cloned into Bluescript M13-KS vector and linearised with an appropriate restriction enzyme. Using T3 RNA polymerase, Q-RNA was in vitro-transcribed and treated with DNaseI to remove plasmid DNA. The input level of calibrator RNA molecules per NASBA reaction was optimised for accurate quantification of the wt-RNA by spiking defined quantities of Q-RNA into serial dilution series of wt-RNA followed by NASBA LUMINEX® analysis. To obtain the standard curve, wt-versus Q-RNA ratios were computed and plotted against the wt-RNA copy number. Input amounts higher than 10$^6$ copies of wt-RNA per assay were not tested, as they were considered clinically irrelevant. This development is exemplarily shown for the E6*I NASBA-LUMINEX® assay (FIG. 2).

Optimal Q-RNA concentrations were determined for every NASBA target and are summarised in Table 2. In general, all NASBA standard curves showed a wide dynamic range of 4 to 5 logs, and were of polynomial rather than linear shape. Due to a flat middle part of the polynomial curve, interpolation of RNA concentrations in unknown samples is imprecise in this part. Nevertheless, all NASBA assays allowed faithful discrimination of 10-fold RNA copy number differences. In addition to quantification, a partial or complete failure of the Q-RNA NASBA, with a simultaneous negative result in the wt-NASBA, indicated the presence of NASBA inhibitors, such as ethanol (data not shown).

Taken together, quantitative NASBA LUMINEX® assays were able to quantify over 4 to 5 orders of magnitude 10-fold differences in wt-RNA quantities present in the sample.

TABLE 2

Detection limits (DL) and Q-RNA amounts of quantitative NASBA-LUMINEX® assays

| | Transcript/ splice site | Coding potential | Quantitative DL [copy # in vitro transcripts] | Q-RNA [copy # per reaction] | Length amplimer [nt] |
|---|---|---|---|---|---|
| viral | 226^409 | E6*I, E7 | 250 | 1,000 | 146 |
| | 226^526 | E6*II, E7 | 25 | 10,000 | 133 |
| | 880^2582 | E1C, E2, E5 | 25 | 1,000 | 106 |
| | 880^2708 | E2, E5 | 250 | 500 | 140 |
| | 880^3358 | E1^E4, E5 | 25 | 5,000 | 147 |
| | 3632^5639 | L1 | 25 | 50,000 | 157 |
| | E6 fl | E6 | 25 | 1,000 | 115 |
| | E7 fl | E7 | 250 | 10,000 | 145 |
| | E1 fl | E1 | 250 | 1,000 | 112 |
| | E5 fl | E5 | 25 | 2,000 | 128 |
| | L1 fl | L1 | 250 | 10,000 | 132 |
| cellular | Apm1 | | 250 | 1,000 | 116 |
| | U1A | | 25 | 1,000 | 226 |
| | Ubc | | 25 | 1,000 | 145 |
| | p16$^{INK4A}$ | | 25,000 | 10,000,000 | 127 |

Example 3: Sensitivity of NASBA Reactions

The detection of various spliced and full-length RNA from HPV16 as well as cellular transcripts required the design of splice site specific hybridisation probes and transcript specific primers annealing up- and downstream of the splice site (Table 1 and Table 3). Careful design of NASBA primers appeared to be crucial for optimal sensitivity. For detection of U1A housekeeping transcripts, validated sensitive primer sequences have been described (U.S. Pat. No. 5,876,937).

Oligonucleotide primers were tested in NASBA-LUMINEX® reactions using serially diluted in vitro-transcribed wt-RNA from RNA targets from HPV16, and cellular transcripts with optimised Q-RNA quantity input (refer to Table 2). The detection limit was defined as the lowest RNA amount revealing a positive result. Of three independent assays performed on different days the highest detection limit is indicated (Table 2).

Figure 3:
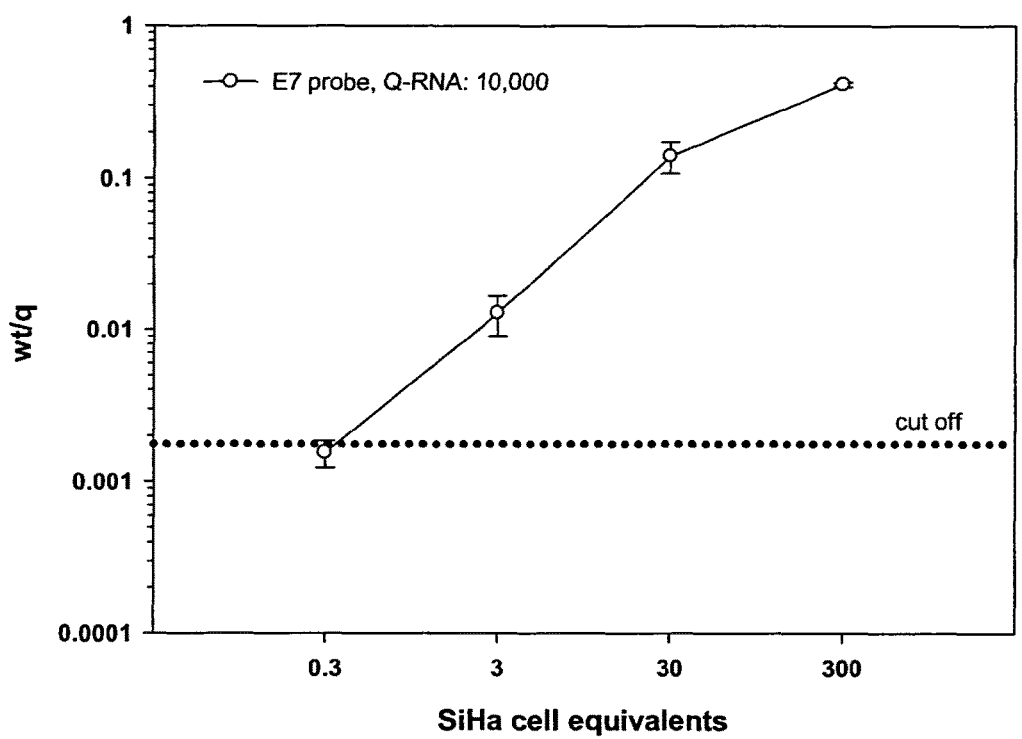
FIG. 3: Detection limits of E7 NASBA using SiHa total RNA. Dilution series of SiHa total RNA were subjected to E7 NASBA-LUMINEX® analysis using 10,000 Q-RNA molecules per NASBA reaction. Mean and standard error of two hybridisation reactions are indicated. Lines between data points are added for better visualisation of curve slopes.

Detection limits for all NASBA targets ranged from 25 to 2,500 copy numbers per NASBA reactions. The only exception was the detection of the cellular p16$^{INK4A}$ requiring 25,000 RNA copies. Moreover, SiHa total RNA was purified, serially diluted and tested by E6*I, E6*II, E7 fl, U1A and Ubc NASBA followed by LUMINEX® hybridisation. As little as 0.3 SiHa cell equivalents could be detected using E6*I and E7 specific NASBA primers while E6*II, Ubc and U1A NASBA primers detected 3 cells (FIG. 3, exemplarily shown for E7 fl). Overall, the quantitative NASBA reactions appeared to be highly sensitive for detection of viral and cellular transcripts.

Table 3. Oligonucleotide primers used in the NASBA-LUMINEX® experiments positive smears with normal (NIL/M, n=25), LSIL (n=24), HSIL (n=24) and CxCa (n=7) cytology. This cross-sectional study aimed at identifying transcripts or transcript patterns being predictive for the presence of low- or high-grade cervical lesions.

Prevalence of Single Transcripts in Different Lesion Types

The spliced transcript 880^2582 was almost exclusively detected in lesions and its prevalence gradually increased from LSIL (30%) to CxCa (57%).

E6*I was detected in 70% of NIL/M, 75% of LSIL, 83% of HSIL and 100% of CxCa cases and, thus, was more often detected than E6*II in all groups (57% of NIL/M, 55% of LSIL, 75% of HSIL and 86% of CxCa cases). The E6*II NASBA primers were also able to anneal to and amplify a 263 nucleotide long E6*I transcript generating a larger RNA amplimer. Despite of the larger size, E6*II primers were even more efficient in amplifying E6*I (this combination was abbreviated with *I(*II)) and identifying a slightly higher prevalence of E6*I in LSIL and HSIL.

TABLE 3

Oligonucleotide primers used in the NASBA-Luminex experiments

| RNA target | P1 sequence[a] | SEQ.ID. | P2 sequence[b] | SEQ.ID. |
|---|---|---|---|---|
| 226^409 | ACAAGACATACATCGACCGGTCCA | 35 | GTGTACTGCAAGCAACAGTTA | 34 |
| 226^526 | GATCAGTTGTCTCTGGTTGCA | 42 | GTGTACTGCAAGCAACAGTTA | 34 |
| 880^2582 | GGATTTCCGTTTTCGTCAAATGGA | 30 | CATCTGTTCTCAGAAACCATA | 29 |
| 880^2709 | TTAGTATTTTGTCCTGACACA | 78 | CATCTGTTCTCAGAAACCATA | 29 |
| 880^3358 | CTGTGTTTCTTYGGTGCCCA | 33 | CATCTGTTCTCAGAAACCATA | 29 |
| 3632^5639 | CATGATAATATATGTTTGTGCGTGCAA | 32 | AATAGTAACACTACACCCATA | 31 |
| E6 fl | GTTCTAAWGTTGTTCCATAC | 43 | ATAGTATATAGAGATGGGAAT | 44 |
| E7 fl | GTCACACTTGCAACARAAGGTT | 45 | TTTGCAACCAGAGACAACTGAT | 46 |
| E5 fl | TCCACAATASTAATACCAATA | 47 | CCACAACATTACTGGCGTGCT | 48 |
| E1 fl | CTACTATGTCATTATCGTAGGC | 49 | GGAGACACGCCAGAATGGAT | 50 |
| L1 fl | AGGTAACCATAGAACCACTAGGTGTA | 51 | GACATTTATTTAATAGGGCTGGT | 52 |
| p16 | TAGGACCTTCGGTGACTGATGATCTA | 53 | GCACCAGAGGCAGTAACCATGCCCGCA | 54 |
| UBC | TCACGAAGATCTGCATTGTCA | 55 | GGATCTCCGTGGGGCGGTGA | 56 |
| APM1 | ATGTGGTTCTTGAGGTCGTAGTT | 57 | ATGTGCACCATCTGCGAGGTC | 58 |
| U1A[c] | GGCCCGGCATGTGGTGCATAA | 59 | CAGTATGCCAAGACCGACTCAGA | 60 |

[a]The 5'-end of the P1 primer contained a T7 RNA polymerase promoter sequence consisting of the following 25 nucleotides: 5'-AAT TCT AAT ACG ACT CAC TAT AGG G-3' (SEQ ID NO: 82).
[b]P2 primer contained a 5'-generic sequence (5'-ata tac tac gga tgg cct g-3') (SEQ ID NO: 83) which was required for the hybridisation with the decorator probe and a 3'-stretch of nucleotides that was identical to the target RNA sequence.
[c]P1 and P2 U1A primers have been published (Greijer, A. E., C. A. Dekkers, and J. M. Middeldorp. 2000. Human cytomegalovirus virions differentially incorporate viral and host cell RNA during the assembly process. J Virol 74: 9078-82.).

Example 4: HPV16 RNA Patterns in Lesions of Different Grade

The expression of HPV16 full-length and spliced as well as cellular p16INK4A, Apm1 and housekeeping RNA sequences in cervical lesions of different grades was analysed by singleplex quantitative NASBA-LUMINEX® assays for targets listed in Table 2. In collaboration with Dr. C. Clavel (Reims, France), RNA samples purified from cervical exfoliated cells stored in PreservCyt™ medium were obtained. The groups consisted of HPV16 DNA- In contrast to L1 full-length containing transcripts which were highly prevalent in all lesion types, the spliced transcript 3632^5639, encoding L1 protein, was most abundant in LSIL (60%), and less frequent in CxCa and also NIL/M (42 and 39%, respectively).

Although E7 full-length containing transcripts were already present in almost all of the NIL/M cases, p16$^{INK4A}$ transcripts were rather rare in this stage but highly prevalent in HSIL to CxCa.

TABLE 4

Prevalence (%) of transcripts in different cytological groups.

| | HPV16 transcript | | | | | | | | | | | | cellular transcript | |
|---|---|---|---|---|---|---|---|---|---|---|---|---|---|---|
| | spliced | | | | | | | full-length | | | | | | |
| N | *I | *I(*II)[1] | *II | 3632^5639 | 880^2582 | 880^2709 | 880^3358 | E1 | E5 | E6 | E7 | L1 | p16 | apm1 |
| 7 | 100 | 100 | 86 | 43 | 57 | 43 | 71 | 100 | 86 | 100 | 100 | 100 | 71 | 86 |
| 24 | 83 | 92 | 75 | 54 | 42 | 67 | 92 | 96 | 92 | 88 | 96 | 96 | 58 | 75 |
| 20 | 75 | 85 | 55 | 60 | 30 | 70 | 90 | 95 | 100 | 90 | 95 | 90 | 40 | 75 |
| 23 | 70 | 65 | 57 | 39 | 4 | 61 | 70 | 96 | 91 | 87 | 96 | 87 | 30 | 91 |

Figure 4:
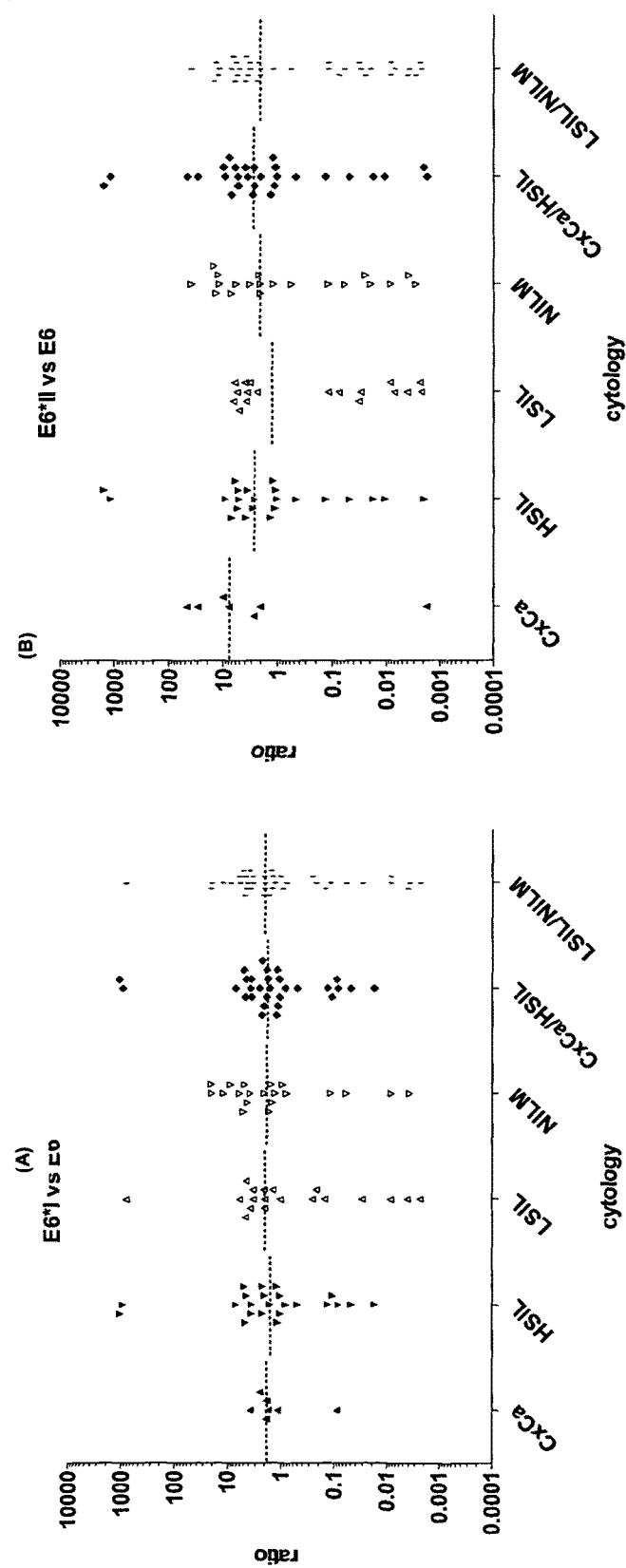
FIG. 4: Pattern of E6*I and *II versus E6 fl expression. Ratios of transcripts E6*I (A) and *II (B) versus E6 fl are plotted on the y-axis and cytological lesion grades as well as groups of lesions are shown on the x-axis. Dotted lines represent median values.

[1]*I(*II), E6*I transcripts amplified by E6*II primers and detected by E6*I probe Expression Levels of Single Transcripts Among the upregulated transcripts, the early oncogene transcripts E6*I, *I(*II), E6*II, E6 full-length and E7 full-length showed a highly significant upregulation in their expression between NIL/M and CxCa (data not shown). To analyse whether the ratio of spliced versus full-length E6 transcripts changed relatively during carcinogenesis, E6*I and E6*II expression was correlated to E6 full-length expression. In contrast to E6*I, only the median of E6*II versus E6 full-length ratios was increased during progression from LSIL towards CxCa (FIG. 4).

In addition, the transcript 880^2582, encoding a potential LCR transactivator, was highly significantly more often expressed in high-grade lesions (HSIL, CxCa) than in NIL/M.

The cellular marker transcripts p16$^{INK4A}$ showed a significant upregulation (p<0.05) in high-grade versus low-grade lesions.

Conversely, expression of transcripts, such as 880^3358, 3632^5639 and L1 encoding proteins required for virus capsid formation and release, although frequently present, was downregulated during progression from LSIL to CxCa (data not shown). This downregulation was particularly strong for the 880^1358 expression that was highly significantly reduced from LSIL to CxCa lesions. L1 full-length expression was highly significantly upregulated (p<0.01) from NIL/M to LSIL indicating low viral activity in infections with normal cytology. L1 full-length sequences, which were detectable in all CxCa, tended to be downregulated in their expression in high-grade lesions compared to LSIL (p>0.05).

The quantitative expression data confirmed the already known upregulation of early oncogene transcripts during cancer progression. In contrast to oncogene transcripts, L1 full-length and 880^3358 (E1^E4) RNA were downregulated during progression. In addition, the 880^2582 transcript was almost exclusively detected in cervical lesions.

Example 5: Transcript Pair Patterns

A limitation of the quantitative transcript analysis in cervical smears (Example 4) is the fact that these samples are likely to contain variable amounts of HPV-infected cells. Normalisation for total RNA corrects for variation in the total amount of cells and RNA quality but not for fractions of HPV-infected cells. The number of HPV-infected cells, however, can have a strong influence on the overall HPV RNA concentrations. To normalise for different amounts of HPV infected cells, pairwise pattern analyses of HPV transcripts were undertaken. Assuming that patterns of two or more transcripts are similar in the majority of HPV-positive cells of a given lesion group, this would be irrespective of whether 100 or 1,000 cells are analysed.

Ratios of expression levels of transcript pairs were correlated to lesion groups: high-grade versus low-grade lesions (CxCa/HSIL versus LSIL/NTL/M). Samples, double negative for both transcripts of interest, were excluded from the analysis. Correlations were evaluated using Wilcoxon rank sum test. Significance of differences of transcript pair expression level ratios between groups was sorted and summarised in Table 5.

TABLE 5

HPV transcript marker combinations from the present invention, their significance and respective cutoffs to discriminate between high-and low-grade lesions

| | Ratio | Reference ratio[a] | Result | Discrimination of high- and low-grade lesions (p-value)[b] |
|---|---|---|---|---|
| high-grade marker | 880^2582 versus 3632^5639 | >0.003 | high-grade lesion | <0.01 |
| | 880^2582 versus 880^3358 | >0.002 | high-grade lesion | <0.01 |
| | 880^2582 versus U1A | >0.005 | high-grade lesion | <0.01 |
| | 880^2582 versus Apm1 | >0.3 | high-grade lesion | <0.01 |
| | 880^2582 versus Ubc | >0.03 | high-grade lesion | <0.01 |
| | 880^2582 versus E1 | >0.02 | high-grade lesion | <0.05 |
| | 880^2582 versus E5 | >0.01 | high-grade lesion | <0.05 |
| | 880^2582 versus L1 | >0.1 | high-grade lesion | <0.05 |
| | 880^2582 versus E6*I | >0.01 | high-grade lesion | <0.05 |
| | E6*II versus U1A | >0.7 | high-grade lesion | <0.01 |
| | E6*II versus Ubc | >1 | high-grade lesion | <0.01 |
| | E6*II versus Apm1 | >6 | high-grade lesion | <0.01 |
| | p16 vs 880^3358 | >0.006 | high-grade lesion | <0.01 |

TABLE 5-continued

HPV transcript marker combinations from the present invention, their significance and respective cutoffs to discriminate between high-and low-grade lesions

|  | Ratio | Reference ratio[a] | Result |  | Discrimination of high- and low-grade lesions (p-value)[b] |
|---|---|---|---|---|---|
| high-grade and integration-marker | E6*II vs 880^3358 | >1.5 | high-grade lesion | integrated | 0.02 |
|  | E6*II vs E5 | >0.6 | high-grade lesion | integrated | 0.02 |
|  | E6*II vs 880^2709 | >100 | high-grade lesion | integrated | >0.05 |
|  | E6 vs E5 | >0.3 | high-grade lesion | integrated | 0.03 |
|  | E1 vs E5 | >0.7 | high-grade lesion | integrated | 0.03 |
| high-grade marker | 880^2582 versus 3632^5639 | <0.003 | low-grade lesion |  | <0.01 |
|  | 880^2582 versus 880^3358 | <0.002 | low-grade lesion |  | <0.01 |
|  | 880^2582 versus U1A | <0.005 | low-grade lesion |  | <0.01 |
|  | 880^2582 versus Apm1 | <0.3 | low-grade lesion |  | <0.01 |
|  | 880^2582 versus Ubc | <0.03 | low-grade lesion |  | <0.01 |
|  | 880^2582 versus E1 | <0.02 | low-grade lesion |  | <0.05 |
|  | 880^2582 versus E5 | <0.01 | low-grade lesion |  | <0.05 |
|  | 880^2582 versus L1 | <0.1 | low-grade lesion |  | <0.05 |
|  | 880^2582 versus E6*I | <0.01 | low-grade lesion |  | <0.05 |
|  | E6*II versus U1A | <0.7 | low-grade lesion |  | <0.01 |
|  | E6*II versus Ubc | <1 | low-grade lesion |  | <0.01 |
|  | E6*II versus Apm1 | <6 | low-grade lesion |  | <0.01 |
|  | p16 vs 880^3358 | <0.006 | low-grade lesion |  | <0.01 |
| high-grade and integration marker | E6*II vs 880^3358 | <1.5 | low-grade lesion | not integrated | 0.02 |
|  | E6*II vs E5 | <0.6 | low-grade lesion | not integrated | 0.02 |
|  | E6*II vs 880^2709 | <100 | low-grade lesion | not integrated | >0.05 |
|  | E6 vs E5 | <0.3 | low-grade lesion | not integrated | 0.03 |
|  | E1 vs E5 | <0.7 | low-grade lesion | not integrated | 0.03 |

[a] cutoff used for discrimination of high- and low-grade lesions; unit, signals of the expression of transcript 1 divided by transcript 2
[b] Wilcoxon rank sum test, p-values below 0.05 were considered statistically significant and p-values below 0.01 were considered highly significant Transcript-to-transcript ratios showing statistically significant and statistically highly significant differences during progression from normal (NIL/M) to CxCa are presented in Table 5. In general, ratios containing at least one spliced transcript were always more significant than ratios utilising full-length transcripts only (state of the art) as determined by NASBA-LUMINEX® tests (Table 6).

TABLE 6

HPV transcript marker combinations known in the art and from the present invention and their significance as analysed by NASBA-LUMINEX® assays.

|  | Transcript combination | Discrimination of high- and low-grade lesions (p-value)[a] |
|---|---|---|
| State of the art | E7 vs E5 | p > 0.05 |
|  | E6 vs E5 | p < 0.05 |
|  | E7 vs L1 | p > 0.05 |
|  | E6 vs L1 | p > 0.05 |
|  | E7 vs Ubc | p > 0.05 |
|  | E6 vs Ubc | p > 0.05 |
| Present invention | 880^2582 versus 3632^5639 | p < 0.01 |
|  | E6*II versus Ubc | p < 0.01 |
|  | p16 vs 880^3358 | p < 0.01 |

[a] wilcoxon rank sum test, p-values below 0.05 were considered statistically significant and p-values below 0.01 were considered highly significant.

A limited number of viral transcripts, such as E6*II, *I(*II) and 880^2582, normalised with either cellular transcripts (Apm1, U1A, Ubc) or with spliced viral transcripts (880^3358, 3632^5639) allowed highly significant discrimination (p<0.01) of high-grade CxCa/HSIL lesions versus either low-grade lesions, LSIL alone, or NIL/M alone. These ratios were driven by the marked upregulation of 880^2582 and E6*II in high-grade lesions. In comparison to HSIL/CxCa, LSIL showed a highly significantly lower expression of E6*II versus 880^3358.

In accordance with the literature, p16$^{INK4A}$ expression appeared to be upregulated in CxCa and HSIL, and when normalised to 880^1358 allowed a highly significant discrimination between CxCa/HSIL and LSIL/NIL/M.

Figure 5:
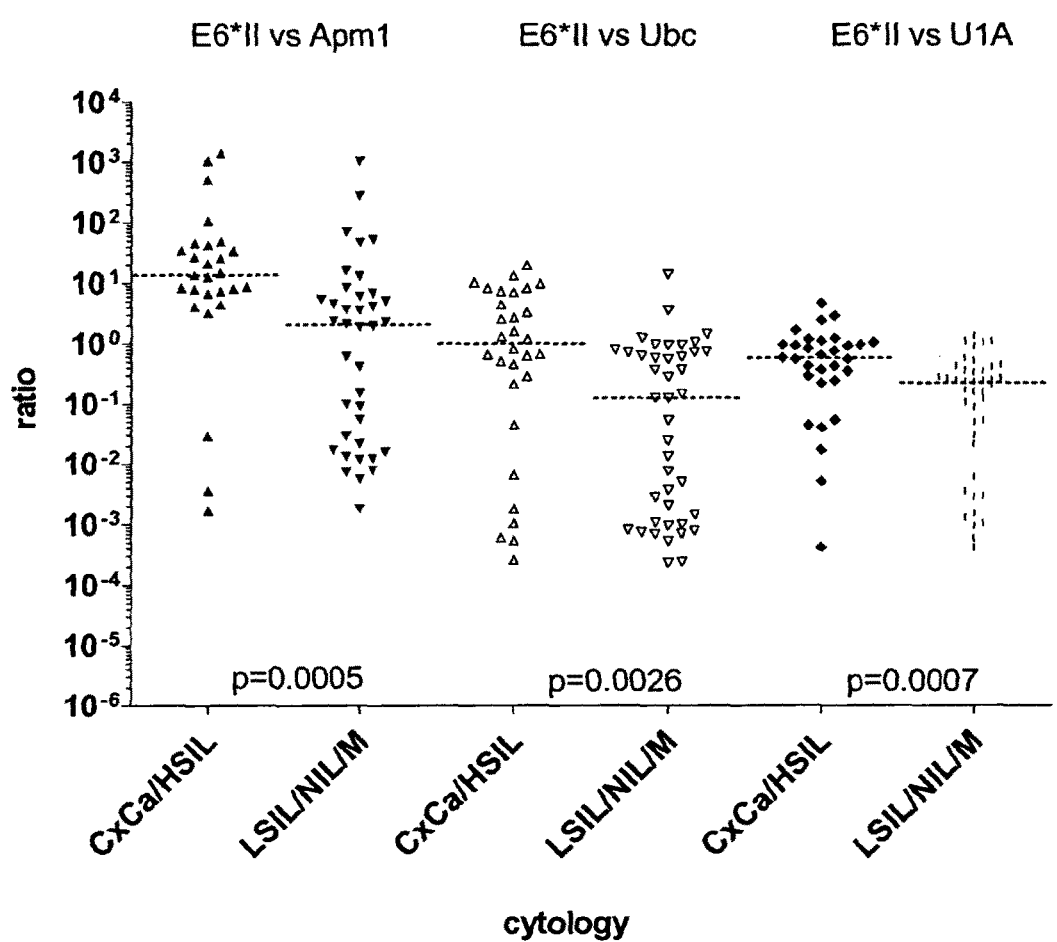
FIG. 5: Normalisation of E6*II expression with cellular transcripts. Ratios of E6*II versus cellular transcripts are plotted on the y-axis and cytological lesion grades as well as groups of lesions are shown on the x-axis. Dotted lines represent median values.

Cellular transcripts, including Apm1, and housekeeping transcripts U1A and Ubc, proved valuable in normalising especially E6*I expression. The resulting normalisations were highly significantly different between high- and low-grade lesions, and independent of the cellular transcript used (FIG. 5).

Taken together, the analyses of spliced transcripts rather than analyses of full-length transcripts provided more significant differences between cytological groups. Among the spliced transcripts E6*II and 880^2582 exhibited strongest differences between groups and could be normalised by a variety of cellular and viral transcripts. Moreover, the expression of 880^2582 strongly correlated with the presence of especially high-grade lesions. Thus, 880^2582 may play a so far unknown role during cancer development, making it a novel HPV marker candidate for high-grade and cancerous lesions.

Example 6: Analysis of the Integration Status

Integration of HPV16 is known to be an important factor during carcinogenesis. In most cases integrations present in tumor cells occurred within the E1/E2/E5 region and lead to the disruption of the viral DNA. Early sequences within E6/E7/E1 are probably not destroyed during integration, and therefore the ratio of early transcripts versus 880^3358, 880^2709 or E5 fl could be used to assess the viral integration event.

The median expression of E6*II versus 880^3358 was most significantly increased in high-grade compared to low-grade lesions. This finding is in good agreement with the known high HPV16 integration prevalence in high-grade lesions (FIG. 6). Using a cutoff of 1.5 with E6*II versus 880^3358, a total of 6 CxCa and 5 HSIL cases could be predicted to contain integrated HPV16 genomes. At least three of these (27%) may contain integrates only as 880^3358 expression was absent in these cases while the other 8 may also contain episomal DNA. Other early transcripts, such as E6*I, but also E6 fl, E7 fl and E1 fl compared to either 880^3358, 880^2709 or E5 fl allowed to predict the presence of transcriptionally active integrates to a lower extent (exemplarily depicted for E6*II versus 880^3358 and E6 fl versus E5, FIG. 6).

In conclusion, the detection and quantification of E6*II RNA sequences in comparison to either 880^3358 or 880^2709 containing RNA sequences appeared to be highly suitable for the assessment of the HPV16 integration status, especially when only integrated genomes are involved. In addition, the E6*II versus 880^3358 ratio or the E6*II versus 880^2709 ratio was superior compared to other ratios containing full-length transcripts.

Example 7: Combination of Different HPV Transcript Markers for Sophisticated Molecular Diagnostics of HPV-Associated Lesions Data from Example 5 and 6 suggested that cervical high-grade lesions may exist with distinct but characteristic transcription patterns.

As such, it was found that compared to the commercially available BIOMERIEUX® HPV kit, a combination of (i) 880^2582 versus 3632^5639 and (ii) E6*II versus 880^3358 markedly increased the sensitivity and specificity of predicting the presence of high-grade or low-grade lesions. Using this combination, a total of 7 CxCa cases (100%), 15 HSIL (63%) were correctly identified as high-grade (CxCa/HSIL), and 14 LSIL (70%) and 21 (91%) normal samples were correctly identified as low-grade (LSIL/NIL/M). In comparison to the PreTect HPV Proofer®, the specificity of NASBA-LUMINEX® assay for discriminating high-grade and low-grade lesions strongly increased from 23% to 83% (FIG. 7). The HPV Proofer® data obtained was in line with previous reports, confirming that a majority of NIL/M samples were positive for E6/E7 mRNA, potentially leading to overtreatment of healthy individuals.

In total, this study provided evidence for the existence of diagnostic HPV16 RNA patterns for grading of cervical lesions. Of the 20 analysed transcripts, only 4 viral splice-site containing transcripts and 1 housekeeping transcript (for RNA quality control) may be sufficient for diagnostic application. Alternatively, shorter oligonucleotides or splice site specific antibodies detecting specific epitopes could be used to detect the respective gene products (Table 7).

TABLE 7

Splice site specific peptides and antibodies

| Splice site | Peptide sequence | SEQ. ID. | Splice site specific nucleotide sequence | SEQ. ID. |
|---|---|---|---|---|
| 226^409 | LLRREVY | 16 | CGTGAGGTGTAT | 15 |
| 226^526 | RREIIK | 39 | CGTGAGATCATC | 38 |
| 880^2582 | DPADSRW | 5 | CTRCAGATTCYA | 4 |
| 880^3358 | DPAAATK | 12 | CTRCAGCAGCRA | 12 |
| 880^2709 | — | — | CTRCAGGACGTG | 82 |

Example 8: Management of Patients Using the Current Invention

A woman, 35 years-old, consults her gynaecologist during the routine cervical cancer precursor screening program. The Pap-test indicates presence of low-grade lesion (LSIL), while a subsequent HPV genotyping assay reveals the presence of HPV16. The cautious physician suggests an RNA profiling test as described above. The result indicates the presence of 880^2582 containing mRNA and thus a high-grade lesion. The physician proposes a follow-up after 1 year. After one year, the woman is tested again by the Pap-test that, this time, indicates the presence of high-grade lesion (HSIL) and the woman is referred to therapy.

Another woman, 37 years-old, consults her gynaecologist during the routine cervical cancer precursor screening program. The Pap-test indicates presence of high-grade lesion (HSIL), and a subsequent HPV genotyping assay reveals the presence of HPV16. The physician suggests an RNA profiling test as described above. The result indicates the presence of a low-grade lesion or normal cytology. The physician proposes a referral to colposcopy that confirms low-grade lesion.

The example from the 35 years-old woman describes that the RNA profiling test as described above, could predict the future development of high-grade lesions. The examples of the 37 years-old woman describes the fact that the Pap-test is often inaccurate and leads to overtreatment of woman diagnosed HSIL positive. Using the RNA profiling test as described above, could reduce unnecessary referrals to colposcopy and therapy.

Figure 8:
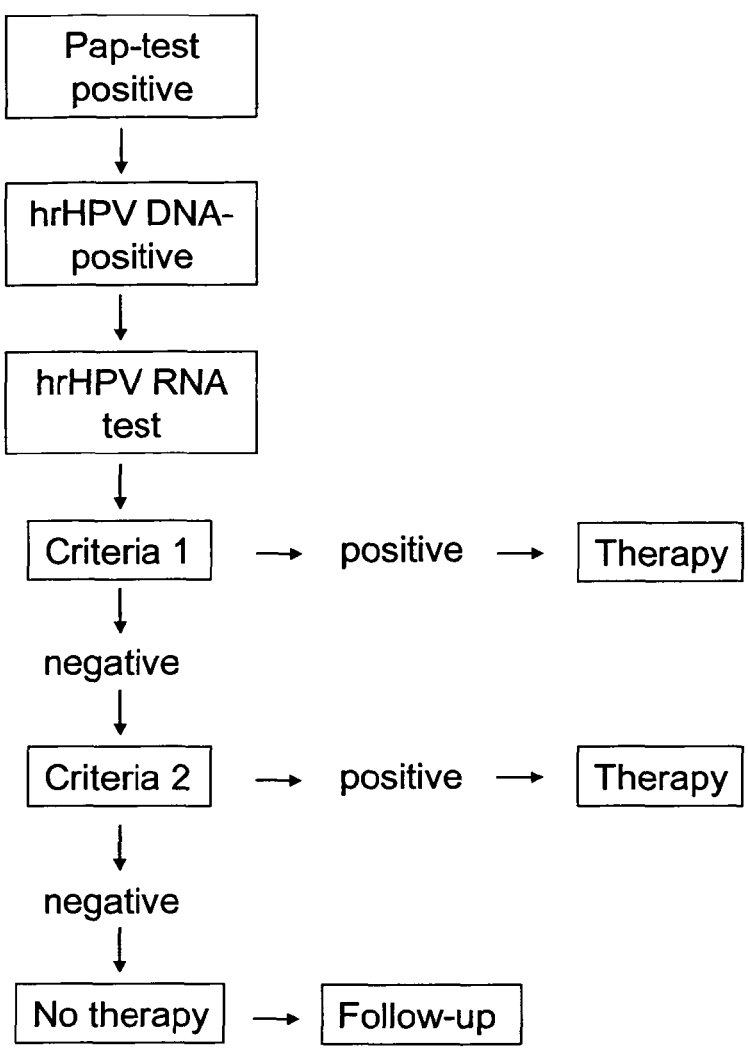
FIG. 8: Scheme for classification of patients.

In a preferred embodiment, primary screening of women is conducted by a Pap-test and/or a hrHPV DNA genotyping assay. HrHPV-positive women are subsequently analysed by the hrHPV RNA test quantifying the gene products from the present invention. In a first step, E1C and the gene product from a second gene e.g. 3632^5639 are evaluated (criterion 1, according to Example 7). Patients with a high-grade result are referred to therapy. Patients being negative for criterion 1, are analysed for integration of HPV, e.g. by assessing the expression of the gene product from E6*II versus e.g. 880^3358 (criterion 2 according to Example 7). Women being positive for criteria 2 are referred to therapy. Patients negative for criteria 1 and 2, are followed up (FIG. 8).

The invention claimed is:

1. A method for differentiating in a human subject with HPV16 between (i) a severe form of HPV16 infection and (ii) a mild form of HPV16 infection, said human subject not comprising the HPV16 genome in an integrated form, and for treating said human subject having said severe form infection comprising the steps of:

a) determining, in a sample of said human subject, the presence or absence of a gene product of 880^2582, said sample selected form the group consisting of a scrape, a biopsy, or a wash/rinse fluid from urogenital tract, a cervical smear, and a Pap smear, and b) differentiating between (i) a severe form of HPV16 infection and (ii) a mild form of HPV16 infection based on the determination performed in step a), wherein the presence of the gene product of 880^2582 indicates the severe form of HPV16 infection, and wherein the absence of the gene product of 880^2582 indicates a mild form of HPV16 infection, wherein the determination of the presence or absence of the gene product comprises the steps of amplifying the gene product with primer oligonucleotides that specifically amplify the gene product and determining the presence or absence of the amplified gene product, wherein the amplification step comprises generation of a cDNA, wherein the determining step is performed by a probe oligonucleotide having a nucleic acid sequence that comprises SEQ ID NO: 4, and c) treating said human subject having said severe form infection comprising a treatment step selected from the group consisting of conisation, loop electrosurgical excision procedure (LEEP), trachelectomy, hysterectomy, chemotherapy, and radiochemotherapy.

2. The method of claim 1, wherein the gene product of 880^2582 are spliced transcripts comprising the 880^2582 junction.

3. The method of claim 1, wherein the probe oligonucleotide has a nucleic acid sequence that comprises SEQ ID NO: 63.

4. A method for differentiating in a human subject with HPV16 between (i) a severe form of HPV16 infection and (ii) a mild form of HPV16 infection, and for treating said human subject having said severe form infection comprising the steps of:

a) determining, in a sample of said human subject, the presence or absence of a gene product of 880^2582, said sample selected form the group consisting of a scrape, a biopsy, or a wash/rinse fluid from urogenital tract, a cervical smear, and a Pap smear, b) assessing in the sample of said human subject the integration status of the HPV16 genome and c) differentiating between (i) a severe form of HPV16 infection and (ii) a mild form of HPV16 infection based on the determination performed in step a), wherein the presence of the gene product of 880^2582 indicates the severe form of HPV16 infection, and wherein the absence of the gene product of 880^2582 indicates a mild form of HPV16 infection, wherein the determination of the presence or absence of the gene product comprises the steps of amplifying the gene product with primer oligonucleotides primers that specifically amplify the gene product and determining the presence or absence of the amplified gene product, wherein the amplification step comprises generation of a cDNA, wherein the determining step is performed by a probe oligonucleotide having a nucleic acid sequence that comprises SEQ ID NO: 4, and treating said human subject having said severe form infection comprising a treatment step selected from the group consisting of conisation, loop electrosurgical excision procedure (LEEP), trachelectomy, hysterectomy, chemotherapy, and radiochemotherapy.

5. A method for differentiating in a human subject with HPV16, between (i) a low-grade squamous intraepithelial lesions (LSIL), high-grade squamous intraepithelial lesions (HSIL), or cervix carcinoma and (ii) a negative for intraepithelial lesions or malignancy (NIL/M), said human subject not comprising the HPV16 genome in an integrated form, and for treating said human subject in category (i) comprising the steps of:

a) determining, in a sample of said human subject, the presence or absence of a gene product of 880^2582, said sample selected form the group consisting of a scrape, a biopsy, or a wash/rinse fluid from urogenital tract, a cervical smear, and a Pap smear, and b) differentiating between (i) a LSIL, HSIL, or cervix carcinoma and (ii) a NIL/M based on the determination performed in step a), wherein the presence of the gene product of 880^2582 indicates the severe form of HPV16 infection, and wherein the absence of the gene product of 880^2582 indicates a mild form of HPV16 infection, wherein the determination of the presence or absence of the gene product comprises the steps of amplifying the gene product with primer oligonucleotides that specifically amplify the gene product and determining the presence or absence of the amplified gene product, wherein the amplification step comprises generation of a cDNA, wherein the determining step is performed by a probe oligonucleotide having a nucleic acid sequence that comprises SEQ ID NO: 4, and treating said human subject in category (i) comprising a treatment step selected from the group consisting of conisation, loop electrosurgical excision procedure (LEEP), trachelectomy, hysterectomy, chemotherapy, and radiochemotherapy.

6. A method for diagnosing in a human subject with HPV16 a severe form of HPV16 infection, said human subject not comprising the HPV16 genome in an integrated form, and for treating said human subject having said severe form infection comprising the steps of:

a) determining, in a sample of said human subject, the presence or absence of a gene product of 880^2582, said sample selected form the group consisting of a scrape, a biopsy, or a wash/rinse fluid from urogenital tract, a cervical smear, and a Pap smear, and b) diagnosing a severe form of HPV16 infection based on the determination performed in step a), wherein the presence of the gene product of 880^2582 indicates the severe form of HPV16 infection, and wherein the absence of the gene product of 880^2582 indicates a mild form of HPV16 infection, wherein the determination of the presence or absence of the gene product comprises the steps of amplifying the gene product with primer oligonucleotides that specifically amplify the gene product and determining the presence or absence of the amplified gene product, wherein the amplification step comprises generation of a cDNA, wherein the determining step is performed by a probe oligonucleotide having a nucleic acid sequence that comprises SEQ ID NO: 4, and treating said human subject having said severe form infection comprising a treatment step selected from the group consisting of conisation, loop electrosurgical excision procedure (LEEP), trachelectomy, hysterectomy, chemotherapy, and radiochemotherapy.

* * * * *